US008394376B2

(12) United States Patent
Iwatsubo et al.

(10) Patent No.: US 8,394,376 B2
(45) Date of Patent: Mar. 12, 2013

(54) THERAPEUTIC AGENTS FOR ALZHEIMER'S DISEASE AND CANCER

(75) Inventors: Takeshi Iwatsubo, Bunkyo-ku (JP); Tatsuhiko Kodama, Bunkyo-ku (JP); Takao Hamakubo, Bunkyo-ku (JP); Taisuke Tomita, Bunkyo-ku (JP); Ikuo Hayashi, Bunkyo-ku (JP); Yasuomi Urano, Bunkyo-ku (JP); Hiroko Iwanari, Shimotuke (JP); Masao Ohkuchi, Tokorozawa (JP)

(73) Assignees: The University of Tokyo, Tokyo (JP); Perseus Proteomics Inc., Tokyo (JP)

( * ) Notice: Subject to any disclaimer, the term of this patent is extended or adjusted under 35 U.S.C. 154(b) by 0 days.

(21) Appl. No.: 12/962,019

(22) Filed: Dec. 7, 2010

(65) Prior Publication Data

US 2011/0165179 A1 Jul. 7, 2011

Related U.S. Application Data

(62) Division of application No. 12/298,151, filed as application No. PCT/JP2007/000438 on Apr. 23, 2007, now abandoned.

(30) Foreign Application Priority Data

Apr. 25, 2006 (JP) .................................. 2006-120875
Jul. 21, 2006 (JP) .................................. 2006-199489

(51) Int. Cl.
*A61K 39/395* (2006.01)

(52) U.S. Cl. ..................... 424/130.1; 435/330; 530/350; 530/387.1; 530/387.3; 530/387.7; 530/388.8; 530/389.1; 530/389.7; 424/133.1; 424/138.1; 424/155.1; 424/174.1

(58) Field of Classification Search .................. 530/350, 530/387.1, 387.3, 387.7, 388.8, 389.1, 389.7; 424/130.1, 133.1, 138.1, 155.1, 174.1; 435/330
See application file for complete search history.

(56) References Cited

U.S. PATENT DOCUMENTS 7,326,540 B2 * 2/2008 Tanzi et al. .................... 435/7.8
2004/0229816 A1 11/2004 Paris et al.

FOREIGN PATENT DOCUMENTS

| EP | 1 514 928 A1 | 3/2005 |
|----|--------------|--------|
| WO | WO 02/29023 A1 | 4/2002 |
| WO | 2004 073630 | 9/2004 |

OTHER PUBLICATIONS

Mitsuda et al. (Life Sci. Apr. 18, 2006; 78 (21): 2444-8).*
Li, T. et al., "Nicastrin is Required for Assembly of Presenilin/γ-Secretase Complexes to Mediate Notch Signaling and for Processing and Trafficking of β-Amyloid Precursor Protein in Mammals", The Journal of Neuroscience, vol. 23, No. 8, pp. 3272-3277, (2003).

Ogura, T. et al., "Three-dimensional structure of the γ-secretase complex", Elsevier, vol. 342, No. 2, pp. 525-534, (2006).
Weng, A.P. et al., "Growth Suppression of Pre-T Acute Lymphoblastic Leukemia Cells by Inhibition of Notch Signaling", Molecular and Cellular Biology, vol. 23, No. 2. pp. 655-664, (2003).
Ian Churcher, et al., "Gamma-Secretase as a Therapeutic Target for the Treatment of Alzheimer's Disease", Current Pharmaceutical Design, vol. 11, No. 26, XP009131855, 2005, pp. 3363-3382.
Ikuo Hayashi, et al., "Selective Reconstitution and Recovery of Functional Gamma-Secretase complex on Budded Baculovirus Particles", Journal of Biological Chemistry, vol. 279, No. 36, XP002904552, Sep. 3, 2004, pp. 38040-38046.
Keiro Shirotani, et al., "Gamma-Secretase Activity Is Associated with a Conformational Change of Nicastrin", Journal of Biological Chemistry, vol. 278, No. 19, XP009131888, May 9, 2003, pp. 16474-16477.
Ikuo Hayashi, et al., "Single Chain Variable Fragment against Nicastrin Inhibits the Gamma-Secretase Activity", Journal of Biological Chemistry, vol. 284, No. 41, XP009131889, Oct. 2009 pp. 27838-27847.
Dennis J. Selkoe, "Alzheimer's Disease: Genes, Proteins, and Therapy", Physiological Reviews, vol. 81, No. 2, 2001, pp. 741-766.
Nobuhiro Suzuki, et al., "An Increased Percentage of Long Amyloid β Protein Secreted by Familial amyloid β Protein Precursor (βAPP$_{717}$) Mutants", Science, vol. 264, May 27, 1994, pp. 1336-1340.
Takeshi Iwatsubo, et al., "Visualization of Aβ42(43) and Aβ40 in Senile Plaques with End-Specific Aβ Monoclonals: Evidence That an Initially Deposited Species Is Aβ42(43)", Neuron, vol. 13, Jul. 1994, pp. 45-53.
Michael S. Wolfe, et al., Two transmembrane aspartates in presenilin-1 required for presenilin endoproteolysis and γ-secretase activity, Nature, vol. 398, Apr. 8, 1999, pp. 513-517.
Yue-Ming Li, et al., "Photoactivated γ-secretase inhibitors directed to the active site covalently label presenilin 1", Nature, vol. 405, Jun. 8, 2000, pp. 689-694.
Oksana Berezovska, et al., "Notch1 and Amyloid Precursor protein Are Competitive Substrates for Presenilin1-dependent γ-Secretase Cleavage", The Journal of Biological Chemistry, vol. 276, No. 32, Aug. 10, 2001, pp. 30018-30023.
Christine L. Curry, et al., "Gamma secretase inhibitor blocks Notch activation and induces apoptosis in Kaposi's sarcoma tumor cells", Oncogene, 24, 2005, pp. 6333-6344.
Andrew P. Weng, et al., "Growth Suppression of Pre-T Acute Lymphoblastic Leukemia Cells by Inhibition of Notch Signaling", Molecular and Cellular Biology, vol. 23, No. 2, pp. 655-664, (2004), (reference previously filed on Oct. 23, 2008, submitting Statement of Relevancy only).
O. Hopfer, et al., "The Notch pathway in ovarian carcinomas and adenomas", British Journal of Cancer, 93, 2005, pp. 709-718.
Esler, et al., (Proc. Natl. Acad. Sci. USA. Mar. 5, 2002; 99 (5): 2720-2725.
Gura (Science, 1997; 278: 1041-1042).

(Continued)

*Primary Examiner* — Stephen Rawlings
(74) *Attorney, Agent, or Firm* — Oblon, Spivak, McClelland, Maier & Neustadt, L.L.P.

(57) ABSTRACT

To provide a therapeutic drug for Alzheimer's disease and/or a cancer. The therapeutic drug for Alzheimer's disease and/or a cancer contains an anti-nicastrin antibody, a derivative of the antibody, or a fragment of the antibody or the derivative.

2 Claims, 21 Drawing Sheets

OTHER PUBLICATIONS

Bergers, et al (Current Opinion in Genetics and Development. 2000; 10: 120-127).
Pasternak et al. (J. Biol. Chem. Jul. 18, 2003; 278: 26687-26694).
Confaloni et al., (Mol. Brain Res. 2005; 136: 12-22.
European Official Communication issued on Mar. 17, 2011 in corresponding European Application No. 07 737 095.

Ikuo Hayashi et al., "Generation of Monoclonal Antibodies Against the Extracellular Domain of Nicastrin", Alzheimer's & Dementia: The Journal of the Alzheimer's Association, Jul. 1, 2006, vol. 2, No. 3, Suppl. 1, P3-412, XP 009145313, p. S497.

* cited by examiner

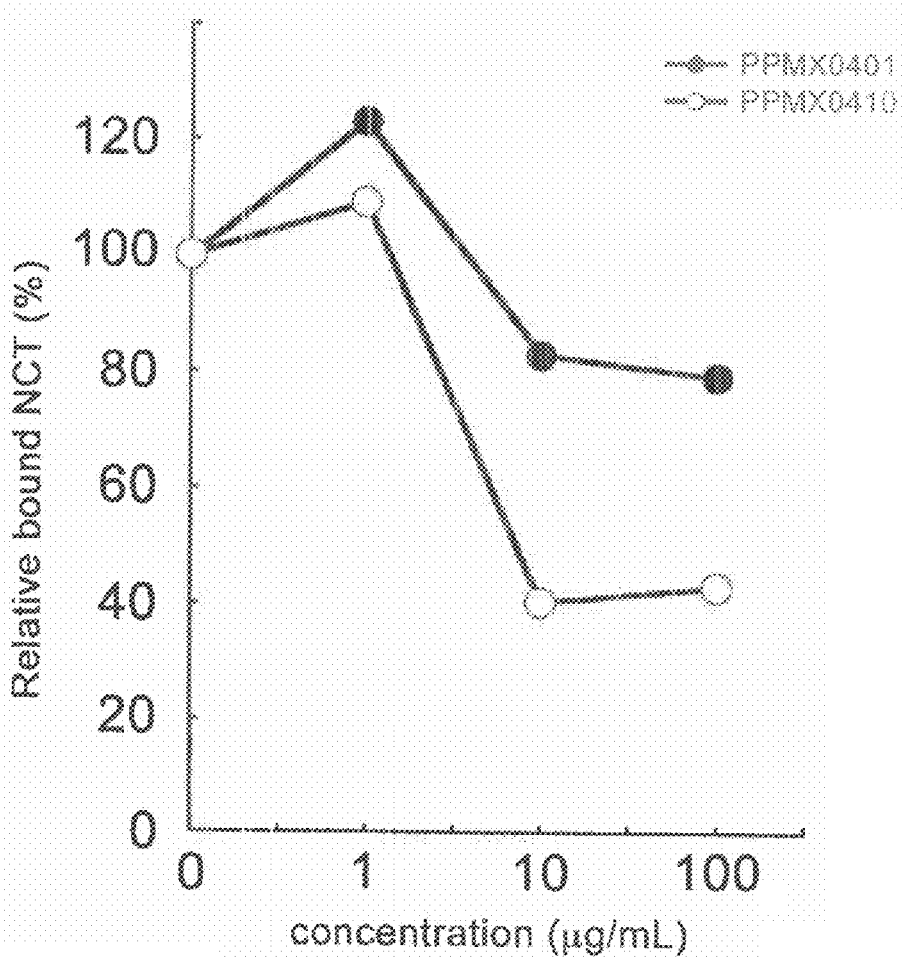

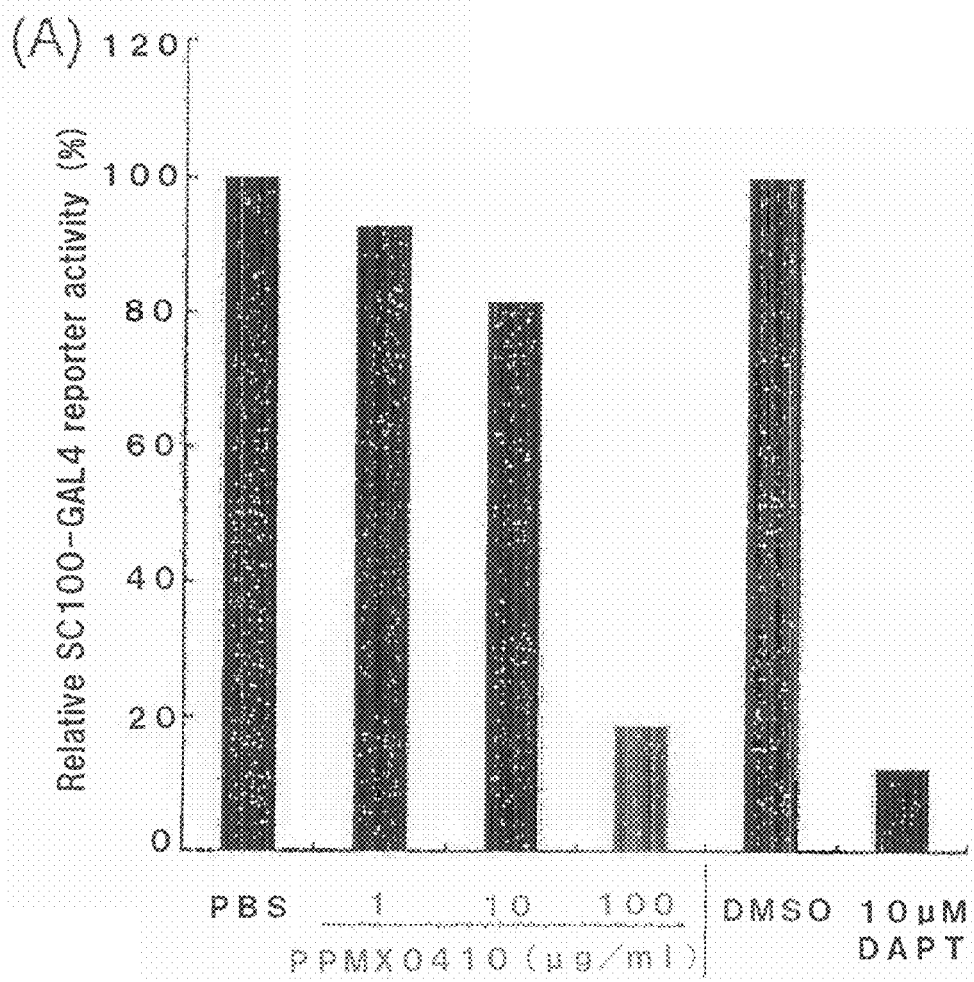

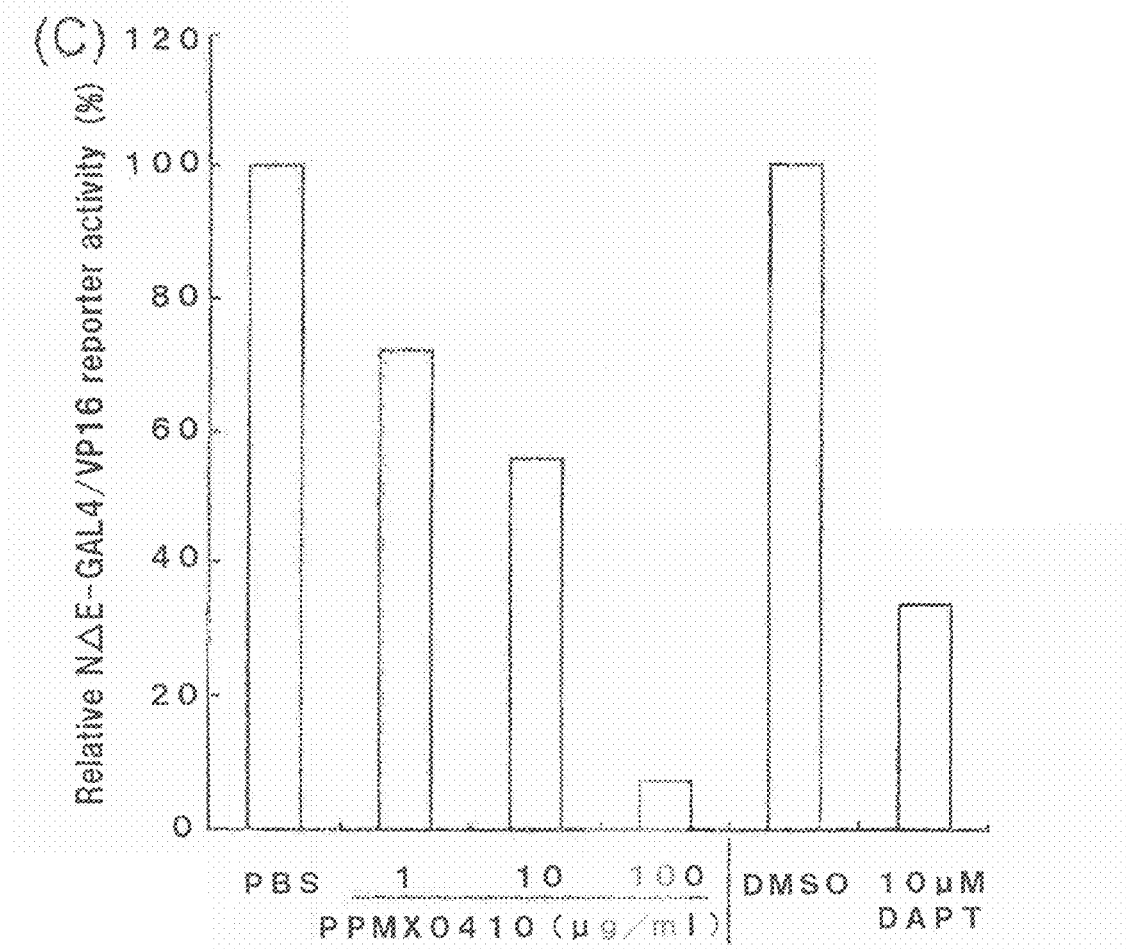

THERAPEUTIC AGENTS FOR ALZHEIMER'S DISEASE AND CANCER

CROSS-REFERENCE TO RELATED APPLICATIONS

This application is a divisional application of U.S. Ser. No. 12/298,151 filed Oct. 23, 2008, abandoned, which was a 371 of PCT/JP2007/000438 filed Apr. 23, 2007 and claims the benefit of JP 2006-120875 filed Apr. 25, 2006 and JP 2006-199489 filed Jul. 21, 2006.

TECHNICAL FIELD

The present invention relates to a therapeutic drug for Alzheimer's disease and/or a cancer, the drug containing an anti-nicastrin antibody.

BACKGROUND ART

In Japan, the three most common death-causing diseases are cancer (30.3%), cardiac disease (15.3%), and cerebrovascular disease (15.2%). As the population ages, the percentage of patients with such diseases increases, which greatly affects medical costs required for treatment or nursing care. In recent years, a nursing-care insurance system for cerebrovascular disease patients has been established as a national policy.

In Japan, the number of deaths from cancer was 320,315 (i.e., 253.9 per 100,000) in 2004. In Japan, in 2003, lung cancer (22.3%) was ranked first among cancer deaths in men, followed by gastric cancer (17.2%) and liver cancer (12.5%), whereas colon cancer (14.6%) was ranked first among cancer deaths in women, followed by gastric cancer (14.2%) and lung cancer (12.3%). According to a report by the National Cancer Center in Japan, regarding five-year survival rates for major types of cancer, the five-year survival rate of pancreatic cancer patients is the lowest (only a few percent), followed by that of patients with gallbladder cancer, lung and bronchial cancer, liver cancer, esophageal cancer, etc. Ohno, Nakamura, et al. have estimated that the number of new cases of male cancers will be 501,000 in 2020 (major sites of cancer: lung, prostate gland, stomach, colon, liver, etc.), whereas the number of new cases of female cancers will be 337,000 in 2020 (major sites of cancer: breast, colon, stomach, lung, uterus, rectum, liver, etc.). Thus, cancer is predicted to become a major death-causing disease in future (as is the case at present), and development of a therapy for cancer is essential.

Cancer therapy has changed with the times. Recently, in addition to hitherto performed surgery, drug therapy, and radiotherapy, endoscopic resection of cancer tissue has been carried out, and chemotherapy for outpatients has been performed more and more. However, about 40% of cancer cases are treated through surgery at present, and radiotherapy or chemotherapy is less effective for some cancers (e.g., pancreatic cancer). In some cancer cases, chemotherapy can reduce a size of cancer tissue, but encounters difficulty in completely curing the disease. In many refractory cancer cases, adverse reactions to an anticancer agent (i.e., side effects thereof) are more pronounced than the effects of the drug.

Cerebrovascular diseases are classified into a cognitive disorder, which is caused by vascular disorder, and Alzheimer's disease, which is a neurodegenerative disease. In Japan, a number of patients with dementia caused by Alzheimer's disease (AD) has increased with adoption of Europeanized and Americanized meals and aging of the population. AD is a neurodegenerative disease which develops various intellectual dysfunctions (including memory impairment) due to degeneration or loss of cerebral cortical neurons. An AD brain is characterized by accumulation of an abnormal protein called "β-amyloid," which is closely related to loss of neurons (Non-Patent Document 1).

β-Amyloid is accumulated in an AD brain in the pathological form of senile plaque or vascular amyloid. From the biochemical viewpoint, β-amyloid is formed of Aβ peptide including 40 to 42 amino acid residues. Aβ is produced from APP (amyloid precursor protein) through two-step cleavage and is secreted extracellularly. In the second step, a C-terminal fragment of APP is cleaved at an intramembrane site by the protease activity of the enzyme γ-secretase, and the thus-formed Aβ is released extracellularly. Cleavage of the C-terminal fragment of APP occurs at different sites; i.e., at position 40 (90%) and at position 42 (10%) (Non-Patent Document 2). Aβ42 is more highly aggregated in the form of β-amyloid and is preferentially accumulated in an AD brain from an early stage (Non-Patent Document 3).

As has been shown, presenilin (PS) protein, which is an expression product of a major pathogenic gene of familial AD, corresponds to a catalytic subunit of γ-secretase, which is a membrane-associated aspartic protease (Non-Patent Documents 4 and 5).

γ-Secretase has been shown to be involved not only in AD but also in Notch signaling (Non-Patent Document 6). As has been known, a γ-secretase inhibitor (i.e., a low-molecular-weight compound) induces apoptosis in Kaposi's sarcoma (Non-Patent Document 7) or inhibits survival of T-ALL cells (Non-Patent Document 8). However, it has been reported that a γ-secretase inhibitor may promote malignant transformation (Non-Patent Document 9). Thus, inhibition of Notch signaling does not necessarily induce cell death in all cancers, and in the future studies will be carried out to determine whether or not a γ-secretase inhibitor can be used as a therapeutic drug for cancer.

Under such circumstances, γ-secretase has been considered important as a therapeutic target for AD or cancer, but a cancer therapeutic drug based on γ-secretase has not successfully been developed for, for example, the following reason. Since γ-secretase is a complex formed of a plurality of membrane proteins and exhibits protease activity in the membrane, difficulty is encountered in reconstituting γ-secretase while maintaining protease activity, and drug screening is not properly carried out by use of γ-secretase.

As has been known, human active γ-secretase complex is a large membrane protein complex having a molecular weight of 250 to 500 kDa or more and including the following four proteins: presenilin, nicastrin (NCT), APH-1, and PEN-2. That is, nicastrin is a constituent molecule of γ-secretase. Many attempts have been made to search for γ-secretase activity inhibitors by use of low-molecular-weight compounds, but no report has been provided to show a result of an experiment by use of an anti-nicastrin antibody for development of a γ-secretase activity inhibitor or a therapy for AD and/or cancer. Although there are many AD and cancer patients, a good drug for a treatment of the diseases has not yet been provided. Development of a therapeutic drug for AD or cancer could reduce burden of nursing care as a matter of course, along with medical costs, Non-Patent Document 1: Selkoe D J., Physiol. Rev. 2001, 81 (2): 741-766, Alzheimer's disease: genes, proteins, and therapy Non-Patent Document 2: Suzuki N., et al. Science 264: 1336, 1994

Non-Patent Document 3: Iwatsubo Odaka A., Suzuki N., Mizusawa H., Nukina N., Ihara Y., Neuron. 1994, 13 (1): 45-53

Non-Patent Document 4: Wolfe M S. Xia. W., Ostaszewski B L., Diehl T S., Kimberly W T., Selkoe D J. (1999), Nature 398 (6727): 513-517

Non-Patent Document 5: Li Y M., Xu M., Lai M T., Huang Q., Castro J L., DiMuzio Mower J., Harrison T., Lellis C., Nadin A., Neduvelil J G., Register R B., Sardana M K., Shearman M S., Smith A L., Shi X P., Yin K C., Shafer J A., Gardell S J. (2000), Nature 2000 Jun. 8, 405 (6787): 689-94

Non-Patent Document 6: J. Biol. Chem. 2001 Aug. 10; 276 (32): 30018-30023

Non-Patent Document 7: Oncogene. 2005 Sep. 22; 24 (42): 6333-6344

Non-Patent Document 8: Mol. Cell. Biol. 2003 January; 23 (2): 655-664

Non-Patent Document 9: Br. J. Cancer. 2005 Sep. 19; 93 (6): 709-718

DISCLOSURE OF THE INVENTION

Problems to be Solved by the Invention

The present invention provides a new therapeutic drug for AD or a cancer. The present invention also provides a screening method for selecting such a therapeutic drug.

Means for Solving the Problems

The present inventors have succeeded in expressing active γ-secretase by use of budding baculovirus (see WO 2005/038023). The present inventors have screened anti-nicastrin antibodies on a basis of active γ-secretase activity by use of budding baculovirus, and as a result have found that an excellent anti-nicastrin antibody is useful as a therapeutic drug for AD and/or a cancer, since the anti-nicastrin antibody exhibits γ-secretase-neutralizing activity and inhibits proliferation of Notch-expressing cells and/or improves survival rate. The present invention has been accomplished on the basis of this finding. Also, the present inventors have found that an anti-nicastrin antibody inhibits reaction between nicastrin and a γ-secretase substrate (i.e., a polypeptide including the intramembrane sequence of a receptor or APP), and thus this reaction system can be employed for selecting, through screening, an antibody which inhibits γ-secretase activity. The present invention has been accomplished also on the basis of this finding.

Accordingly, the present invention provides a therapeutic drug for AD and/or a cancer containing an anti-nicastrin antibody, a derivative of the antibody, or a fragment of the antibody or the derivative.

The present invention also provides a screening method for selecting an antibody which inhibits γ-secretase activity, characterized by comprising reacting nicastrin with a γ-secretase substrate in a presence of a test antibody.

The present invention also provides use of an anti-nicastrin antibody, a derivative of the antibody, or a fragment of the antibody or the derivative for producing a therapeutic drug for Alzheimer's disease and/or a cancer.

The present invention also provides a method for treatment of Alzheimer's disease and/or a cancer, characterized by comprising administering an anti-nicastrin antibody, a derivative of the antibody, or a fragment of the antibody or the derivative to a subject in need thereof.

Effects of the Invention

According to the therapeutic drug for AD and/or a cancer of the present invention, γ-secretase activity can be inhibited by an anti-nicastrin antibody, to thereby treat Alzheimer's disease and/or a cancer.

According to the screening method of the present invention, the reaction system between nicastrin and a γ-secretase substrate can be employed for selecting an antibody which inhibits γ-secretase activity; i.e., an antibody effective for the treatment of Alzheimer's disease and/or a cancer.

BRIEF DESCRIPTION OF THE DRAWINGS

FIG. 3 discloses the "DYIGS" peptide as SEQ ID NO: 19.

FIG. 21 shows an effect of anti-nicastrin antibodies on inhibition of binding between nicastrin and N100-FLAG.

DETAILED DESCRIPTION OF THE INVENTION

Figure 1:
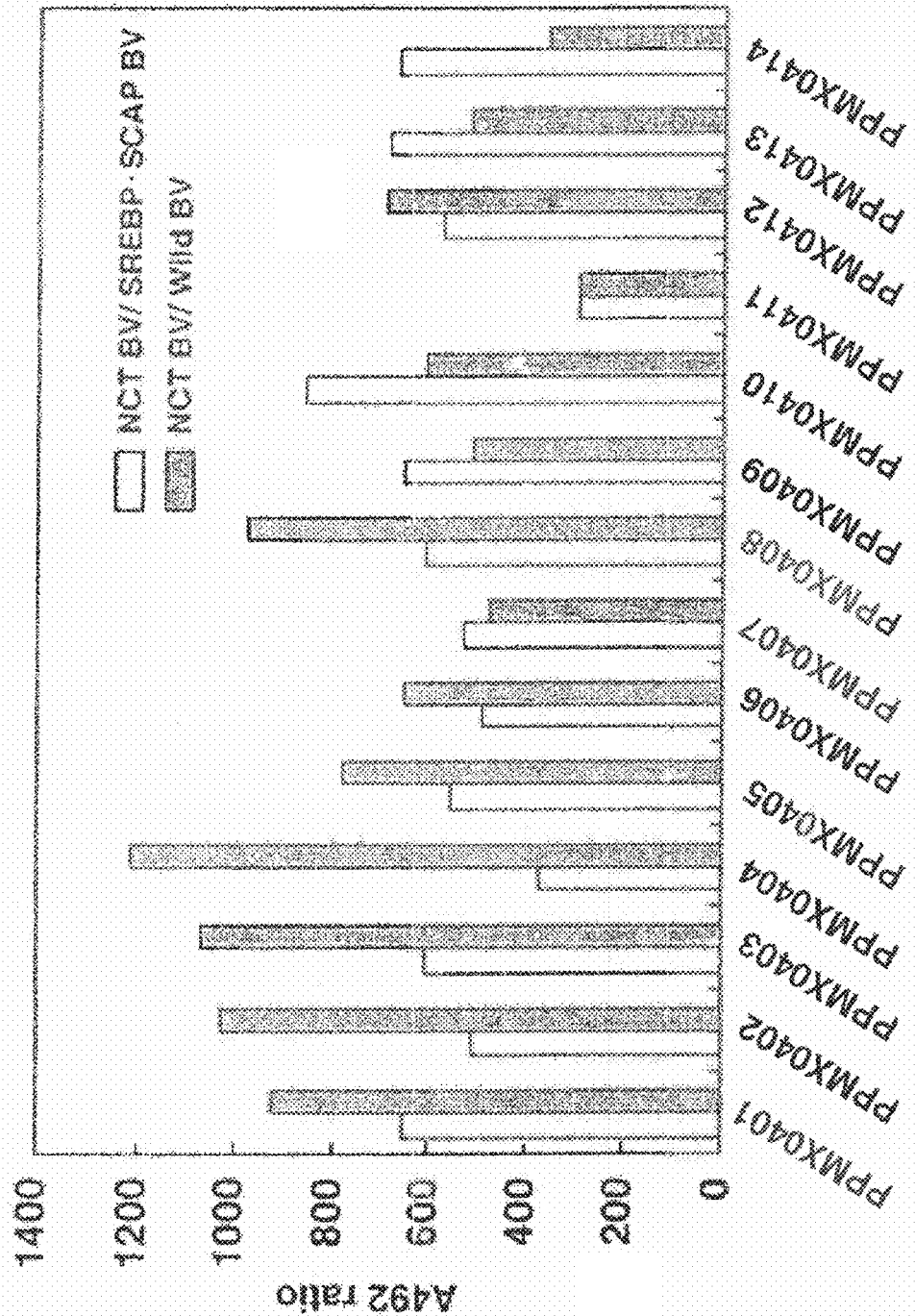
FIG. 1 shows results of screening of anti-nicastrin antibodies through BV-ELISA.

The present invention will next be described in detail.

The present invention is directed to a therapeutic drug for AD and/or a cancer containing an anti-nicastrin antibody, a derivative of the antibody, or a fragment of the antibody or the derivative; to use of the antibody, the derivative, or the fragment for producing such a therapeutic drug; and to a method for the treatment of Alzheimer's disease and/or a cancer.

In the present invention, as described hereinbelow, the anti-nicastrin antibody derivative encompasses a modified anti-nicastrin antibody and an anti-nicastrin antibody to which a compound exhibiting a desired pharmaceutical activity has been bound.

Nicastrin is a membrane protein and forms a complex to exhibit γ-secretase activity. An amino acid sequence of nicastrin and a sequence of the gene coding therefor are disclosed in GenBank™ number (NM_015331) (SEQ ID Nos: 1 and 2). As used herein, "nicastrin protein" encompasses both full-length nicastrin protein and a fragment of nicastrin. As used herein, "fragment of nicastrin" refers to a polypeptide which includes a predetermined region of nicastrin protein and which does not necessarily have a function of natural nicastrin protein.

Nicastrin protein, which is employed as an antigen in the present invention, is preferably human nicastrin protein, but is not necessarily limited thereto. The nicastrin protein employed in the present invention may be nicastrin derived from any non-human species, such as canine nicastrin, feline nicastrin, mouse nicastrin, hamster nicastrin, or drosophila nicastrin. Preferably, an antibody selected by use of nicastrin protein neutralizes human active γ-secretase including nicastrin as a constituent molecule.

Human active γ-secretase is a large-molecule membrane protein complex having a molecular weight of 250 to 500 kDa or more and including the following four proteins: fragmented presenilin, nicastrin, APH-1, and PEN-2.

The active γ-secretase employed in the present invention may be prepared through any of methods described in the Examples hereinbelow (WO 2005/038023). Natural human active γ-secretase may be prepared from a human brain homogenate, but is very difficult to employ for screening of γ-secretase inhibitors. Therefore, the active γ-secretase employed is preferably prepared through the method by the present inventors for successfully expressing an active γ-secretase complex by use of budding baculovirus (see WO 2005/038023).

In the present invention, γ-secretase activity is determined through a method by Yasuko Takahashi, et al. (J. Biol. Chem. 2003 May 16; 278 (20): 18664-70), which is a generally known method. Specifically, a test substance is mixed with microsomes (serving as an enzyme) prepared from brain tissue or cultured cells, and the mixture is incubated at 4° C. for 12 hours. Subsequently, 1 μM C100FmH serving as a substrate is added to the reaction mixture, and the mixture is incubated at 37° C. for 12 hours. Thereafter, an amount of amyloid-β is measured through sandwich ELISA, to thereby determine γ-secretase activity.

Preparation of Anti-Nicastrin Antibody

Preferably, the anti-nicastrin antibody employed in the present invention not only binds specifically to nicastrin protein, but also neutralizes human active γ-secretase. No particular limitation is imposed on an origin, type (monoclonal or polyclonal), and form of the anti-nicastrin antibody. Specifically, the anti-nicastrin antibody may be a known antibody such as a mouse antibody, a rat antibody, an avian antibody, a human antibody, a chimera antibody, and a humanized. (CDR-grafted) antibody. The anti-nicastrin antibody is preferably a human, chimera, or humanized monoclonal antibody.

Examples of the anti-nicastrin monoclonal antibody include a monoclonal antibody produced by a hybridoma, and a monoclonal antibody produced in a host transformed with an expression vector containing a gene for the antibody through a genetic engineering technique.

Basically, a hybridoma which produces the monoclonal antibody may be prepared through a known technique as described below. Specifically, the hybridoma may be prepared through the following procedure: a mammal is immunized with nicastrin protein serving as a sensitizing antigen through a customary immunization method; the resultant immunocyte is fused with a known parental cell through a customary cell fusion method; and a cell for producing the monoclonal antibody is selected through a customary screening method.

Specifically, the monoclonal antibody can be prepared as follows.

Nicastrin is a membrane protein and forms a complex to exhibit .gamma.-secretase activity. An amino acid sequence of nicastrin and a sequence of the gene coding therefor are disclosed in GenBank™ number (NM_015331) (SEQ ID Nos: 1 and 2). As used herein, "nicastrin protein" encompasses both full-length nicastrin protein and a fragment of nicastrin. As used herein, "fragment of nicastrin" refers to a polypeptide which includes a predetermined region of nicastrin protein and which does not necessarily have a function of natural nicastrin protein.

Subsequently, the thus-purified nicastrin protein is employed as a sensitizing antigen. Alternatively, a partial peptide of the nicastrin protein may be employed as a sensitizing antigen. Such a partial peptide may be obtained through chemical synthesis on the basis of the amino acid sequence of nicastrin protein, through integration of a portion of the nicastrin gene into an expression vector, or through degradation of natural nicastrin protein by use of protease. No particular limitation is imposed on a site or size of a nicastrin protein portion employed as a partial peptide.

No particular limitation is imposed on the mammal which is immunized with the sensitizing antigen, but preferably, the mammal is selected in consideration of compatibility of the resultant immunocyte with a parental cell employed for cell fusion. In general, a rodent (e.g., mouse, rat, or hamster), avian, rabbit, monkey, or the like is employed.

Immunization of an animal with the sensitizing antigen is carried out through a known method. For example, in a generally employed immunization method, the sensitizing antigen is intraperitoneally or subcutaneously injected into a mammal. Specifically, the sensitizing antigen is diluted by PBS (phosphate-buffered saline), saline, or the like, to form a suspension of an appropriate volume. If desired, the resultant suspension is mixed with an appropriate volume of a common adjuvant (e.g., Freund's complete adjuvant). After emulsification of the resultant mixture, the emulsion is administered to a mammal several times every 4 to 21 days. Upon immunization with the sensitizing antigen, an appropriate carrier may be employed. Particularly when the sensitizing antigen is a partial peptide of low molecular weight, preferably, the partial peptide employed for immunization is bound to a carrier protein such as albumin or keyhole limpet hemocyanin.

After immunization of a mammal as described above, and following confirmation of an increase in serum level of an antibody of interest, immunocytes are collected from the mammal and then subjected to cell fusion. The type of immunocytes is particularly preferably splenocyte.

A mammalian myeloma cell is employed as a parental cell which is fused with the aforementioned immunocyte. The myeloma cell employed is preferably a known cell line; for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H., et al., Cell (1976) 8, 405-415), SP2/0 (Shulman, M., et al., Nature (1978) 276, 269-270), FO (de St. Groth, S. F., et al., J. Immunol. Methods (1980) 35, 1-21), 51.94 (Trowbridge, I. S. J. Exp. Med. (1978) 148, 313-323), or R210 (Galfre, G., et al., Nature (1979) 277, 131-133).

Cell fusion between the aforementioned immunocyte and myeloma cell may be basically carried out through a known method, such as a method of Kohler, Milstein, et al. (Kohler. G. and Milstein, C., Methods Enzymol. (1981) 73, 3-46).

More specifically, the aforementioned cell fusion is carried out in a common nutrient culture medium in the presence of, for example, a cell fusion promoter. Examples of the cell fusion promoter employed include polyethylene glycol (PEG) and Sendai virus (HVJ). If desired, an auxiliary agent (e.g., dimethyl sulfoxide) may be further added in order to enhance cell fusion efficiency.

The ratio of the immunocyte and myeloma cell employed may be determined as desired. For example, an amount of the immunocyte is preferably 1 to 10 times that of the myeloma cell. Examples of the culture medium which may be employed for the aforementioned cell fusion include RPMI 1640 medium and MEM medium, which are suitable for proliferation of the aforementioned myeloma cell line; and culture media which are generally employed for such a cell culture. Such a culture medium may be employed in combination with a serum supplement such as fetal calf serum (FCS).

In the cell fusion, predetermined amounts of the aforementioned immunocyte and myeloma cell are well-mixed in any of the aforementioned culture media, and a solution of PEG (e.g., PEG having an average molecular weight of about 1,000 to about 6,000) which has been heated in advance to about 37° C. is added to the resultant mixture in a predetermined amount (generally 30 to 60% (w/v)), followed by mixing, to thereby yield a hybridoma of interest. Subsequently, a procedure including sequential addition of an appropriate culture medium and removal of a supernatant obtained through centrifugation is repeated, to thereby remove substances (e.g., a cell fusion promoter) which are not suitable for growth of the hybridoma.

Separation of the thus-yielded hybridoma is carried out through culturing in a common selective culture medium such as a HAT medium (a medium containing hypoxanthine, aminopterin, and thymidine). A culturing in the aforementioned HAT medium is continued for a sufficient period of time (generally several days to several weeks) for apoptosis of cells (i.e., non-fused cells) other than the hybridoma of interest. Subsequently, a customary limiting dilution technique is performed for screening and monocloning of the hybridoma which produces a target antibody.

An antibody which recognizes nicastrin protein may be prepared through a method described in WO 03/104453.

Screening and monocloning of a target antibody may be carried out through a known screening method on a basis of antigen-antibody reaction. For example, an antigen is bound to a carrier (e.g., beads made of polystyrene or a similar material, or a commercially available 96-well microtiter plate) and then reacted with a culture supernatant of the hybridoma, and subsequently the carrier is washed, followed by reaction with, for example, an enzyme-labeled secondary antibody, to thereby determine whether or not the culture supernatant contains a target antibody which reacts with a sensitizing antigen. Cloning of the hybridoma which produces a target antibody may be performed through, for example, a limiting dilution technique. In this case, the antigen may be an antigen employed in immunization.

In addition to preparation of the aforementioned hybridoma through immunization of a non-human animal with an antigen, a human antibody of interest having binding activity to nicastrin may be prepared by sensitizing human lymphocyte with nicastrin in vitro, and fusing the thus-sensitized lymphocyte with a human-derived myeloma cell having permanent division capacity (see JP-A-01-059878). Alternatively, nicastrin serving as an antigen may be administered to a transgenic animal having all of the human antibody gene repertoires, to thereby yield a cell which produces an anti-nicastrin antibody, and a human antibody against nicastrin may be obtained from the cell after it has been immortalized (see WO 94/25585, WO 93/12227, WO 92/03918, and WO 94/02602).

The thus-prepared monoclonal-antibody-producing hybridoma can be subcultured in a common culture medium and can be stored in liquid nitrogen for a long period of time.

A monoclonal antibody is produced from the hybridoma through, for example, a method in which the hybridoma is cultured by a customary technique, and the monoclonal antibody is obtained from the resultant culture supernatant; or a method in which the hybridoma is administered to a mammal exhibiting compatibility with the hybridoma to thereby proliferate the hybridoma, and the monoclonal antibody is obtained from ascitic fluid of the mammal. The former method is suitable for obtaining a monoclonal antibody of high purity, whereas the latter method is suitable for a mass production of a monoclonal antibody.

The monoclonal antibody employed in the present invention may be a recombinant antibody. Such a recombinant antibody is produced through the following procedure: the antibody gene is cloned from the hybridoma; the gene is integrated into an appropriate vector; and the vector is introduced into a host, followed by production of the recombinant antibody through a genetic recombination technique (see, for example, Vandamme, A. M., et al., Eur. J. Biochem. (1990) 192, 767-775, 1990).

Specifically, mRNA encoding a variable (V) region of an anti-nicastrin antibody is isolated from the hybridoma which produces the anti-nicastrin antibody. Isolation of mRNA is carried out as follows. Total RNA is prepared through a known method such as the guanidine ultracentrifugation method (Chirgwin, J. M., et al., Biochemistry (1979) 18, 5294-5299) or the AGPC method (Chomczynski, P., et al., Anal. Biochem. (1987) 162, 156-159), and target mRNA is prepared by means of, for example, mRNA Purification Kit (product of Pharmacia). Alternatively, mRNA may be directly prepared by means of QuickPrep mRNA Purification Kit (product of Pharmacia).

The thus-obtained mRNA is employed for synthesis of cDNA of the antibody V region by use of reverse transcriptase. Synthesis of cDNA is carried out by means of, for example, AMV Reverse Transcriptase First-strand cDNA Synthesis Kit (product of Seikagaku Corporation). Alternatively, synthesis and amplification of cDNA may be carried out by means of, for example, 5'-Ampli FINDER RACE Kit (product of Clontech) or the 5'-RACE method using PCR (Frohman, M. A., et al., Proc. Natl. Acad. Sci. USA (1988) 85, 8998-9002; Belyavsky, A., et al., Nucleic Acids Res. (1989) 17, 2919-2932).

A target DNA fragment is purified from the resultant PCR product and ligated to vector DNA. Subsequently, a recombinant vector is prepared from the vector DNA and then introduced into *Escherichia coli* or the like, followed by colony selection, to thereby prepare a recombinant vector of interest. The nucleotide sequence of the target DNA fragment is determined through a known method such as a dideoxynucleotide chain termination method.

DNA encoding the V regions of a target anti-nicastrin antibody is obtained, and then the DNA is integrated into an expression vector containing DNA encoding constant regions (C regions) of the target antibody.

In order to produce the anti-nicastrin antibody employed in the present invention, the gene for the antibody is integrated into an expression vector so that the gene can be expressed under a control of an expression regulatory region (e.g., an enhancer or a promoter). Subsequently, a host cell is transformed with this expression vector for expression of the antibody.

The gene for the antibody may be expressed by transforming a host cell with both an expression vector containing the DNA encoding a heavy chain (H chain) of the antibody and an expression vector containing the DNA encoding a light chain (L chain) of the antibody, or by transforming a host cell with a single expression vector containing the DNA encoding the heavy and light chains of the antibody (see WO 94/11523).

In addition to the aforementioned host cell, a transgenic animal may be employed for production of a recombinant antibody. For example, an antibody gene is inserted into a gene encoding a protein produced specifically in milk such as goat β-casein) to prepare a fusion gene. A DNA fragment including the fusion gene having the inserted antibody gene is injected into an embryo of a goat, and this embryo is implanted into a female goat. An antibody of interest is obtained from milk produced by transgenic goats born from the goat impregnated with the embryo or progeny thereof. In order to increase an amount of the antibody-containing milk produced by the transgenic goats, hormones may be administered to the transgenic goats as appropriate (Ebert, K. M. et al., Bio/Technology (1994) 12, 699-702).

In the present invention, in addition to the aforementioned antibodies, an artificially modified, genetically recombinant antibody (e.g., a chimera antibody or a humanized antibody) may be employed. Such a modified antibody may be produced through a known method.

Specifically, a chimera antibody is prepared through the following procedure: the above-obtained DNA encoding the antibody V regions is ligated to the DNA encoding the human antibody C regions; the thus-ligated DNA is integrated into an expression vector; and the expression vector is introduced into a host for production of the chimera antibody. Through this known procedure, a chimera antibody useful for the present invention can be prepared.

A humanized antibody is also called a "reshaped human antibody" and is obtained by grafting a complementarity determining regions (CDRs) of an antibody from a non-human mammal (e.g., mouse) into the complementarity-determining regions of a human antibody. Typical gene recombination techniques for preparing such a humanized antibody are known (see European Patent Application. Laid-Open (EP) No. 125023 and WO 96/02576).

Specifically, a DNA sequence designed to ligate a CDRs of a mouse antibody to a framework regions (FRs) of a human antibody is synthesized through PCR employing, as primers, several oligonucleotides prepared to have portions overlapping terminal regions of both the CDRs and FRs (see the method described in WO 98/1388).

The framework regions of the human antibody ligated via the CDRs are selected in such a manner that the complementarity-determining regions form a proper antigen-binding site. If necessary, amino acid residues in the framework regions of the antibody variable regions may be substituted so that the complementarity-determining regions of a reshaped human antibody form a proper antigen-binding site (Sato, K., et al., Cancer Res. (1993) 53, 851-856).

The C regions employed in a chimera antibody or a humanized antibody may be those of a human antibody; for example, Cγ1, Cγ2, Cγ3, and Cγ4 in the H chain, and Cκ and Cλ in the L chain. The C regions of the human antibody may be modified so as to improve a stability of the antibody or to achieve stable production thereof.

The chimera antibody includes the variable regions of an antibody derived from a non-human mammal and the constant regions of a human antibody. Meanwhile, the humanized antibody includes the complementarity-determining regions of an antibody derived from a non-human mammal and the framework regions and C regions of a human antibody. The humanized antibody is useful as an active ingredient of a therapeutic agent, since it exhibits low antigenicity in a human body.

The anti-nicastrin antibody employed in the present invention is not limited to the whole antibody molecule. So long as the anti-nicastrin antibody binds to nicastrin protein, the antibody may be an antibody fragment, derivatives of the antibody (including a modified antibody, and an antibody bound to a compound exhibiting a desired pharmaceutical activity), a divalent antibody, or a monovalent antibody. The anti-nicastrin antibody is preferably an antibody which neutralizes human active γ-secretase.

Examples of the antibody fragment include Fab, $F(ab')_2$, Fab/c having Fab having one Fv and complete Fc, and single-chain Fv (scFv) in which Fv fragments of the H or L chain are linked together with an appropriate linker. Specifically, an antibody is treated with an enzyme (e.g., papain or pepsin) to produce an antibody fragment. Alternatively, a gene encoding such an antibody fragment is constructed and introduced into an expression vector, followed by expression in an appropriate host cell (see, for example, Co, M. S., et al., J. Immunol. (1994) 152, 2966-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 652-663; Rousseaux, J., et. al., Methods in Enzymology (1989) 121, 663-669; and Bird, R. E., et al., TIBTECH (1991) 9, 132-137).

A single-chain Fv (scFv) is obtained by linking the H chain V region and L chain V region of an antibody. In the scFv fragment, the H chain V region and the L chain V region are linked by a linker (preferably, a peptide linker) (Huston, J. S., et al., Proc. Natl. Acad. Sci. U.S.A. (1988) 85, 5879-5883). The H chain V region and the L chain V region in the scFv fragment may be derived from any of the antibodies described herein. The peptide linker employed for linking the V regions is, for example, any single-stranded peptide including 12 to 19 amino acid residues.

DNA encoding the scFv fragment is obtained through PCR amplification employing, as a template, an entire sequence of the DNA encoding the H chain or 1 chain V region of the aforementioned antibody or the DNA encoding the L chain or L chain V region of the antibody, or a portion of the DNA sequence encoding an amino acid sequence of interest, in combination with a primer pair defining both ends of the DNA sequence, followed by amplification employing the DNA encoding a peptide linker region in combination with a primer pair which defines both ends of the DNA so that the respective ends are linked to the H and L chains.

Once the DNA encoding the scFv fragment is prepared, an expression vector containing the DNA and a host transformed with the expression vector can be obtained through a customary method, and the scFv fragment can be obtained through a customary method by use of the host.

Such an antibody fragment may be produced by a host after a gene for the fragment has been obtained and expressed in a manner similar to that described above. As used herein, the term "antibody" also encompasses such an antibody fragment.

Also, a modified anti-nicastrin antibody prepared through conjugation of a molecule (e.g., polyethylene glycol (PEG) or a sugar chain) to an anti-nicastrin antibody may be employed. Through such modification, a half-life of the anti-nicastrin antibody can be prolonged, and hydrolysis or elimination thereof can be reduced in blood. As used herein, the term "antibody" also encompasses such a modified antibody. Such a modified antibody may be prepared through chemical modification of the above-obtained antibody or a fragment thereof. Methods for modifying antibodies have already been established in the art.

Also, the antibody employed in the present invention may be a bispecific antibody. The bispecific antibody may have antigen-binding sites recognizing different epitopes of NCT molecule. A bispecific antibody may be prepared by binding HL pairs of two antibodies, or may be obtained from a bispecific-antibody-producing fused cell prepared through fusion of hybridomas producing different monoclonal antibodies. Alternatively, a bispecific antibody may be prepared through a genetic engineering technique.

The above-constructed gene for the antibody may be expressed through a known method, to thereby yield the antibody. In the case where a mammalian cell is employed, the antibody gene may be expressed by functionally binding a common useful promoter, the gene which is expressed, and a polyA signal downstream of a 3'-end thereof. Examples of the promoter/enhancer which may be employed include human cytomegalovirus immediate early promoter/enhancer.

Other promoters/enhancers which may be employed for antibody expression in the present invention include viral promoters/enhancers such as retrovirus, polyomavirus, adenovirus, and simian virus 40 (SV40); and promoters/enhancers derived from mammalian cells, such as human elongation factor 1α (HEF1α).

When SV40 promoter/enhancer is employed, gene expression can be readily carried out through a method of Mulligan, et al. (Nature (1979) 277, 108), whereas when HEF1α promoter/enhancer is employed, gene expression can be readily carried out through a method of Mizushima, at al. (Nucleic Acids Res. (1990) 18, 5322).

In the case where *Escherichia coli* are employed, the gene for the antibody can be expressed by functionally binding a common useful promoter, a signal sequence for secreting the antibody, and the antibody gene which is expressed. Examples of the promoter which may be employed include lacZ promoter and araB promoter. When lacZ promoter is employed, the gene can be expressed through a method of Ward, at al. (Nature (1098) 341, 544-546; FASEB J. (1992) 6, 2422-2427), whereas when araB promoter is employed, the gene can be expressed through a method of Better, et al. (Science (1988) 240, 1041-1043).

When the antibody is produced in a periplasm of *Escherichia coli*, a pelB signal sequence (Lei, S. P., at al., J. Bacterial. (1987) 169, 4379) may be employed as a signal sequence for secreting the antibody. The antibody produced in the periplasm is isolated and then employed by appropriately refolding a structure of the antibody.

Replication origins which may be employed include those derived from SV40, polyomavirus, adenovirus, bovine papilloma virus (BPV). In order to increase gene copy number in a host cell system, the expression vector employed may contain a selective marker such as aminoglycoside transferase (APH) gene, thymidine kinase (TK) gene, *Escherichia coli* xanthine-guanine phosphoribosyl transferase (Ecogpt) gene, or dihydrofolate reductase (dhfr) gene.

Any expression system such as a eukaryotic or prokaryotic system may be used for production of the antibody employed in the present invention. Examples of the eukaryotic cell include animal cells of, for example, established mammalian cell line, cells of insect cell line, filamentous fungal cells, and yeast cells; and examples of the prokaryotic cell include cells of a bacterium such as *Escherichia coli*.

Preferably, the antibody employed in the present invention is expressed in a mammalian cell such as CHO, COS, myeloma, BHK, Vero, or HeLa cell.

Subsequently, the above-transformed host cell is cultured in vitro or in vivo to produce a target antibody. Culturing of the host cell is carried out through a known method. For example, DMEM, MEM, RPMI 1640, or IMDM may be employed as a culture medium, and a serum supplement such as fetal calf serum (FCS) may be employed in combination.

The above-expressed or produced antibody can be isolated from cells or a host animal and purified to homogeneity. Isolation and purification of the antibody employed in the present invention may be carried out by means of an affinity column. Examples of columns employing protein A column include Hyper D, POROS, and Sepharose F.F. (products of Pharmacia). No particular limitation is imposed on the method for isolation/purification of the antibody, and the antibody may be isolated or purified through any method which is generally employed for isolation/separation of proteins. For example, the antibody may be isolated/purified by appropriately selecting or combining chromatography columns other than the aforementioned affinity columns, filters, ultrafiltration, salting out, dialysis, etc. (Antibodies A Laboratory Manual. Ed Harlow, David Lane, Cold Spring Harbor Laboratory, 1988).

As described in the Examples hereinbelow, the above-obtained anti-nicastrin antibody recognizes nicastrin protein (i.e., a constituent molecule of human active γ-secretase), binds specifically to nicastrin protein, and exhibits an activity to neutralize γ-secretase. In addition, the anti-nicastrin antibody has an ability to inhibit proliferation of γ-secretase-dependent cancer cells. Therefore, the anti-nicastrin antibody, a derivative of the antibody, or a fragment of the antibody or the derivative is effective as a therapeutic drug for Alzheimer's disease and/or a cancer.

Conceivably, the cancer which can be treated by the present invention is a nicastrin-expressing cancer and/or a γ-secretase-dependent cancer.

Examples of such a cancer include lung cancer and T-cell acute lymphoblastic leukemia.

As used herein, "nicastrin-expressing cancer" refers to a cancer in which nicastrin protein is produced through expression of the nicastrin gene; and "γ-secretase-dependent cancer" refers to a cancer in which proliferation of cancer cells requires γ-secretase, and cancer cell proliferation is inhibited or cancer cells die through inhibition of γ-secretase activity.

The anti-nicastrin antibody derivative or a fragment thereof also encompasses a product prepared by conjugating a compound exhibiting a desired pharmaceutical activity to the anti-nicastrin antibody or a fragment thereof through a customary method. Such an anti-nicastrin antibody derivative may be employed in, for example, a missile therapy specifically targeting nicastrin. As used herein, "compound exhibiting a desired pharmaceutical activity" refers to a compound exhibiting, for example, a pharmaceutical activity to inhibit or promote a substance (e.g., an enzyme or a receptor) which directly or indirectly causes symptoms to progress.

Examples of compounds exhibiting a desired pharmaceutical activity for cancer treatment include a compound which causes damage to cancer cells, and a compound which provides or enhances cytotoxic activity (e.g., a radioisotope). The radioisotope employed may be any radioisotope known to those skilled in the art, but is preferably $^{131}$I, $^{99m}$Tc, $^{111}$In, or $^{90}$Y.

Cancer treatment employing an antibody bound to a radioisotope-containing compound may be carried out through a method known to those skilled in the art. Specifically, firstly, a small amount of an antibody bound to a radioisotope-containing compound is administered to a patient, followed by whole-body scintigraphy. After determination that a degree of binding between the antibody and normal tissue cells is low but the degree of binding between the antibody and cancer cells is high, a large amount of the radioisotope-bound antibody is administered to the patient.

The therapeutic drug of the present invention may be prepared into a drug product by subjecting both the drug and a pharmaceutically acceptable carrier well known in the art to a drug preparation process such as mixing, dissolution, granulation, tableting, emulsification, encapsulation, or lyophilization.

For oral administration, the therapeutic drug of the present invention may be mixed with, for example, a pharmaceutically acceptable solvent, excipient, binder, stabilizer, or dispersant, and the mixture may be prepared into a dosage form such as tablet, pill, sugar-coated agent, soft capsule, hard capsule, solution, suspension, emulsion, gel, syrup, or slurry.

For parenteral administration, the therapeutic drug of the present invention may be mixed with, for example, a pharmaceutically acceptable solvent, excipient, binder, stabilizer, or dispersant, and the mixture may be prepared into a dosage form such as injection solution, suspension, emulsion, cream, ointment, inhalant, or suppository. For formulation of an injection, the therapeutic drug of the present invention may be dissolved in an aqueous solution, preferably, a physiologically compatible buffer (e.g., Hanks' solution, Ringer solution, or saline buffer). The composition may be in the form of suspension, solution, or emulsion in an oily or aqueous vehicle. Alternatively, the therapeutic drug may be produced in the form of powder, and, before use, the drug may be prepared into an aqueous solution or suspension with, for example, sterile water. For inhalation administration, the therapeutic drug of the present invention may be powdered and may be prepared into a powder mixture together with an appropriate base such as lactose or starch. For production of a suppository, the therapeutic drug of the present invention may be mixed with a conventional suppository base such as cocoa butter. The therapeutic drug of the present invention may be formulated into a sustained-release drug product by encapsulating the drug in, for example, a polymer matrix.

A dose of the therapeutic drug of the present invention or a number of doses thereof varies depending on a dosage form or administration route thereof, or the symptom, age, or body weight of a patient in need thereof. The therapeutic drug can be administered once to several times per day so that a daily dose of the drug is generally about 0.001 mg to about 1,000 mg per kg body weight, preferably about 0.01 mg to about 10 mg per kg body weight.

Generally, the therapeutic drug is administered through a parenteral route; for example, injection (e.g., subcutaneous injection, intravenous injection, intramuscular injection, or intraperitoneal injection), or transdermal, transmucosal, transnasal, or transpulmonary administration. However, no particular limitation is imposed on the administration route of the therapeutic drug, and the drug may be orally administered.

A screening method for selecting an antibody which inhibits γ-secretase activity.

As described in the Examples hereinbelow, an anti-nicastrin antibody has been found to inhibit reaction between nicastrin and a γ-secretase substrate (e.g., C99 or N99).

Therefore, the screening method of the present invention for selecting an antibody which inhibits γ-secretase activity is a promising method for searching a therapeutic drug for AD or cancer.

In the screening method of the present invention, nicastrin is reacted with a γ-secretase substrate (e.g., a polypeptide formed of the entirety or a portion of Notch receptor and/or APP (including the intramembrane sequence)) in the presence of a test antibody, and the reaction between nicastrin and the substrate is detected.

Specifically, nicastrin is reacted with a polypeptide formed of the entirety or a portion of the sequence of Notch or APP in the presence of a test antibody through addition thereof, and whether or not the added test antibody inhibits the reaction is determined through a known detection method.

Alternatively, a test antibody is exposed to cells expressing nicastrin and a polypeptide formed of the entirety or a portion of the sequence of Notch and/or APP, and whether or not a product is produced through the reaction between nicastrin and the polypeptide is determined through a known detection method.

Preferably, the latter screening method is carried out. The latter screening method requires a simpler screening process. In addition, when the Latter screening method is carried out in combination with a known detection method, numerous test antibodies can be screened to determine whether or not they inhibit γ-secretase activity within a short period of time. Thus, a therapeutic drug for AD or cancer can be developed within a short period.

The γ-secretase substrate employed in the screening method may be a polypeptide formed of the entirety or a portion of Notch receptor (NM_008714) (SEQ ID NO: 3) (including the intramembrane sequence) and/or a polypeptide formed of the entirety or a portion of APP protein (NM_000484) (SEQ ID NO: 4) (including the intramembrane sequence). The polypeptide formed of the entirety or a portion of Notch receptor or APP protein may be prepared through expression of a gene having a sequence (5'-cacctcatgtacgtggcagcggccgccttcgtgctcctgttctttgtgggctgtggggtgc tgctg-3') (SEQ ID NO: 6) and encoding a polypeptide including the intramembrane sequence of Notch receptor (NH$_2$-HLMYVAAAAFVLLFFVGCGVLL-COOH) (SEQ ID NO: 5), or a gene having a sequence (5'-ggtgcaatcattggactcatg-gtgggcggtgttgtcatagcgacagtgatcgtcatcacct tggtgatgctg-3') (SEQ ID NO: 8) and encoding a polypeptide including the intramembrane sequence of APP protein (NH$_2$-GAIIGLM-VGGVVIATVIVITLVML-COOH) (SEQ ID NO: 7). Particularly preferably, the polypeptide formed of the entirety or a portion of Notch receptor or APP protein is prepared through expression of a gene having a sequence (SEQ ID NO: 10) and encoding 99 amino acid residues (No. 1711 to No.

1809) of a protein of Notch receptor including the intramembrane sequence (NH$_2$-VKSEPVEPPLPSQLHLVY-VAAAAFVLLFFVGCGVLLSRKRRRQH-GQLWFPEGFKVSEASKK KRREPLGEDSVGLKPLKNASDGALMDDN-QNEWGDEDLE-COOH) (SEQ ID NO: 9) (the 99 amino acid residues may be called "N99"), or a gene having a sequence (SEQ ID NO: 12) and encoding 99 amino acid residues (the C-terminus to No. 99) of a protein of APP including the intramembrane sequence (NH$_2$-DAEFRHDS-GYEVHHQKLVFFAEDVGSNKGAIIGLM-VGGVVIATVIVITLVMLKKKQYTSIH HGVVEVDAAVTPEERHLSKMQQNGYENP-TYKFFEQMQN-COOH) (SEQ ID NO: 11) (the 99 amino acid residues may be called "C99").

The polypeptide serving as a γ-secretase substrate, which is formed of the entirety or a portion of a protein, is obtained from the corresponding amino acid sequence or expressing a gene encoding the amino acid residues. Alternatively, the polypeptide is obtained from a natural product.

The polypeptide serving as a γ-secretase substrate, which is formed of the entirety or a portion of a protein, is preferably derived from human. However, the origin of the polypeptide is not limited to human, and the polypeptide may be derived from any non-human species such as dog, cat, mouse, hamster, or drosophila.

The amino acid sequence of nicastrin or a γ-secretase substrate or the sequence of the gene coding therefor may be provided, before expression thereof, with a tag sequence (e.g., V5 or FLAG sequence), which is selected in consideration of a detection method employed.

Whether or not a test antibody inhibits γ-secretase activity may be determined through a known technique such as co-immunoprecipitation (IP), western blotting, ELISA, reporter gene assay, a SPA beads method, a fluorescence polarization method, or a homogeneous time-resolved fluorescence method. These techniques may be employed singly or in combination as appropriate.

For example, co-immunoprecipitation (IP) and western blotting may be employed in combination. In this case, the amino acid sequence of nicastrin or a peptide formed of the entirety or a portion of Notch receptor or APP (including the intramembrane sequence) or the sequence of the gene coding therefor is provided with a tag sequence (e.g., FLAG or V5 sequence) through a known method, and the protein or peptide is expressed in a host cell.

Nicastrin or the peptide formed of the entirety or a portion of Notch receptor or APP (including the intramembrane sequence) is extracted from the host cell by a known extraction method including lysis of the cell membrane, followed by purification as appropriate.

The thus-extracted nicastrin is diluted with a culture medium and then mixed with a test, antibody, and reaction is carried out at 4° C. for 8 to 12 hours. Thereafter, the Notch or APP peptide is added to the reaction mixture, followed by further mixing for three to four hours. A HEPES buffer containing 0.5% CHAPSO is employed as a buffer solution.

An antibody corresponding to the tag is added, and IP is carried out. Subsequently, a precipitated fraction is analyzed through a known western blot technique. The tag-corresponding antibody may be bound to a carrier (e.g., agarose beads) in advance.

In this case, when nicastrin and the peptide formed of the entirety or a portion of Notch receptor or APP (including the intramembrane sequence) are precipitated in smaller amounts, the test antibody is determined to have higher percent inhibition of γ-secretase activity.

Alternatively, binding assay may be carried out by immobilizing one of nicastrin and the peptide on, for example, a carrier or an assay plate, and labeling the other with, for example, a radioisotope or a fluorescent substance. A test antibody detected may be provided with a tag (e.g., an antigen) or a label (e.g., a radioisotope).

Whether or not a test antibody inhibits γ-secretase activity may be determined through, for example, a method employing a GAL4-UAS system and ELISA or a reporter gene in combination. In this case, a construct (SC100G) is prepared by inserting GAL4 into C99 through a known method, and a reporter construct (UAS-luc) is prepared by inserting a UAS sequence into an upstream region of the luciferase gene serving as a reporter gene. These constructs are introduced into host cells through a known technique such as lipofection. Cells constitutively expressing nicastrin are selected by use of, for example, an antibiotic-resistant marker as appropriate.

The constitutively expressing cells are cultured at 37° C. for 24 hours, and then a test antibody is exposed to the cells, followed by expression of the transgene. Expression of the gene is induced by addition of 10 mM n-butylic acid. After culturing at 37° C. for 12 hours, the cells or the resultant supernatant is recovered.

In the case where the cells are employed, when the amount of luminescence generated by luciferase is reduced after lysis of the cells, the test antibody is determined to inhibit binding between nicastrin and a Notch receptor intramembrane peptide or an APP peptide, and to inhibit cleavage of the Notch receptor intramembrane peptide or the APP peptide; i.e., the test antibody is determined to have high percent inhibition of γ-secretase activity.

In the case where the supernatant is employed, an extracellularly released Aβ peptide fraction having an indicator applicable to ELISA is assayed through ELISA. When the degree of ELISA reaction is low, the test antibody is determined to inhibit binding between nicastrin and Notch receptor or an APP peptide, and to inhibit cleavage of the intramembrane sequence of a Notch receptor peptide or the APP peptide; i.e., the test antibody is determined to have high percent inhibition of γ-secretase activity.

Alkaline phosphatase or GFP may be employed in place of luciferase.

EXAMPLES

The present invention will next be described in more detail by way of examples, which should not be construed as limiting the invention thereto.

Example 1

Culturing of Insect Cells

Insect cells (*Spodoptera frugiperda*, Sf9) were cultured at 27° C. by use of Grace's Insect Media Supplemented (Invitrogen) containing 10% fetal bovine serum (FBS, Sigma), penicillin (100 U/mL), and streptomycin (100 µg/mL) (Invitrogen). When mass culture was carried out, 0.001% pluronic F-68 (Invitrogen) was added to the aforementioned medium placed in a 1-L spinner flask.

Example 2

Preparation of Recombinant Virus

Human nicastrin cDNA cloned into pEF6-TOPO/V5-His (Invitrogen) (pEF6-NCT) (T. Tomita et al., FEBS Lett. 520

(2002) 117-121) was subcloned into pBlueBac4.5 (Invitrogen) so that the V5-His tag derived from the vector was provided on the C-terminal side, to thereby prepare a human-nicastrin-containing construct (pBlueBac4.5-NCT). Recombinant virus preparation was carried out according to a protocol attached Bac-N-Blue Transfection Kit (Invitrogen). Specifically, Sf9 cells were transfected with Bac-N-Blue DNA and the above-prepared plasmid (4 μg), followed by purification through a plaque assay (several times), to thereby prepare a recombinant virus containing only a target gene. After preparation of a high titer stock, a titer of the virus was determined through a plaque assay.

Example 3

Confirmation of Expression of Nicastrin on BV

Expression of nicastrin (i.e., a single-transmembrane protein) on BV was confirmed by use of the above-prepared recombinant virus. Sf9 cells were infected with the recombinant virus at a multiplicity of infection (MOI) of 5, and the cells and BV were recovered after 12 hours, 24 hours, 48 hours, or 72 hours initiation of infection, followed by confirmation of expression of nicastrin through immunoblotting by use of an anti-nicastrin N-terminal antibody (anti-NCT (N-19), SantaCruz) and an anti-His antibody. As a result, nicastrin was found to be sufficiently expressed in both a cell fraction and a BV fraction 48 hours after initiation of infection. This indicates that, similar to the case of SREBP-2 (Y. Urano, et al., Biochem. Biophys. Res. Commun. 308 (2003) 191-196), nicastrin is expressed on BV.

Example 4

Preparation of Anti-Nicastrin Antibody by Use of Budding Virus (BV)

Since a large amount of gp64, which is a virus-derived membrane protein and exhibits high antigenicity, is expressed on BV, when a mouse is infected with BV, an anti-gp64 antibody is strongly induced, and difficulty is encountered in yielding an antibody to a target antigen. Therefore, gp64 transgenic mice, which were prepared so as to exhibit resistance to gp64, were employed, as mice for immunization.

Sf9 cells ($5 \times 10^8$ cells/500 mL) were infected with human-nicastrin-expressing recombinant virus (NCT-BV) at an MOI of 5, and cultured for 48 hours, followed by recovery of a culture supernatant. BV serving as an antigen was prepared from the culture supernatant through ultracentrifugation, and then gp64 transgenic mice were immunized five times with the antigen.

Figure 2:
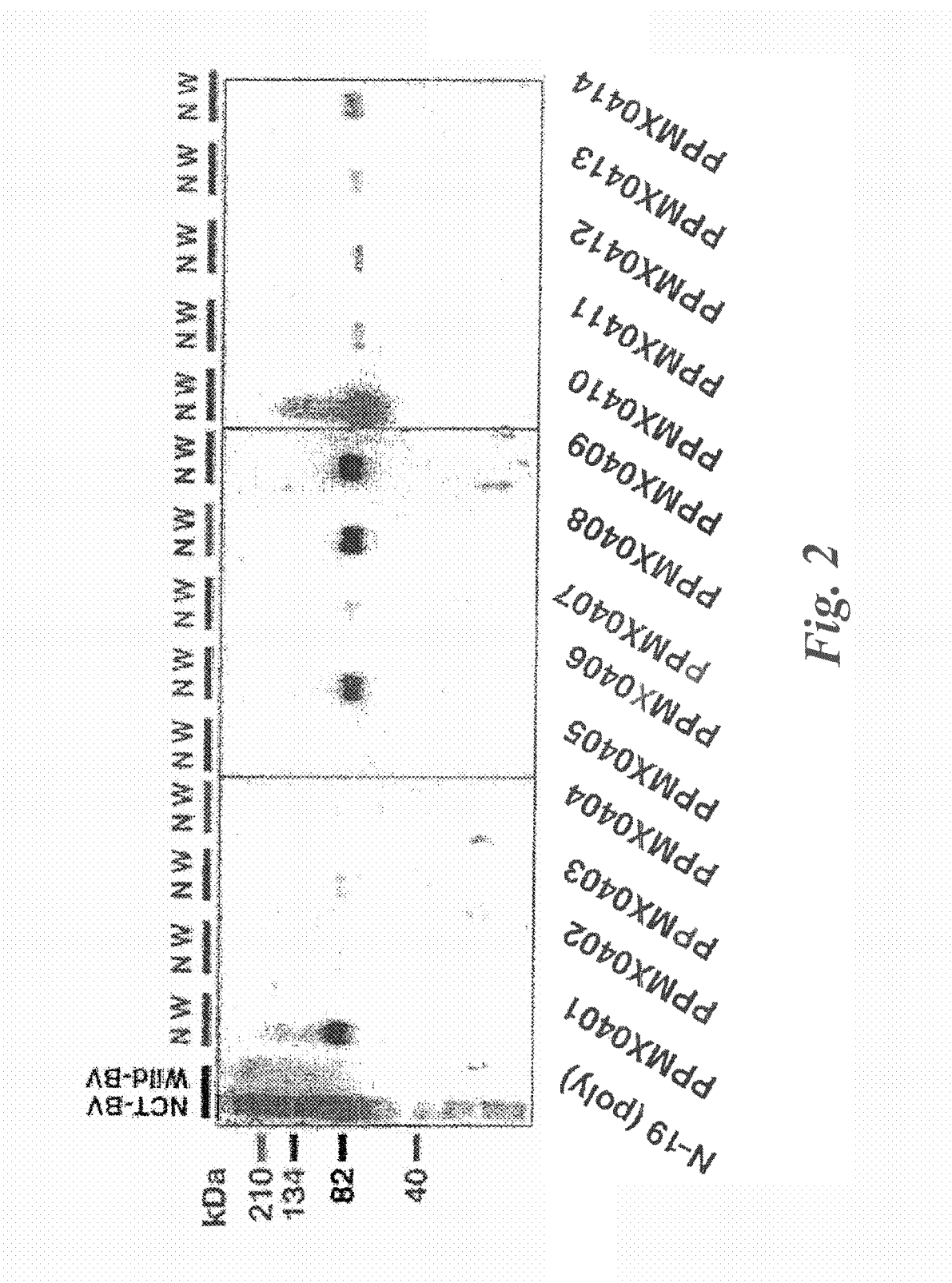
FIG. 2 shows results of screening of anti-nicastrin antibodies through western blot analysis by use of BV.

Screening of antisera and a resultant hybridoma culture supernatants was carried out through BV-ELISA by a customary method. There were added NCT-BV employed during immunization (serving as an antigen for immobilization), and SREBP+SCAP-BV prepared through coinfection of SREBP-2 and SREBP cleavage-activating protein (SCAP) (Y. Urano, et al., Biochem. Biophys. Res. Commun. 308 (2003) 191-196) or wild-BV containing no foreign gene (20 μg/mL in saline) (serving as a negative control) (50 μL/well). As a result, there were yielded many clones which do not respond to wild-type BV or SREBP/SCAP-expressing BV but show positive response to only nicastrin-expressing BV (FIG. 1). Similarly, there were yielded a plurality of clones (e.g., PPMX0401 and PPMX0410) which recognize nicastrin expressed on BV, as determined through immunoblotting employing BV (FIG. 2).

Example 5

Cell Culture

COS-7 cells (cells derived from simian kidney), HeLa cells (cells derived from human cervical cancer), A549 cells (cells derived from human lung cancer), or NKO cells (fibroblasts derived from nicastrin knockout mouse: T. Li, et al., J. Neurosci. 23 (2003) 3272-3277) were cultured in Dulbecco's modified Eagle's medium (DMEM, Sigma) containing 10% FBS, penicillin (100 U/mL), and streptomycin (100 μg/mL) (Invitrogen) at 37° C. and 5% $CO_2$.

Example 6

Identification of Antibody by Use of BV and Forced Expression Product

The culture supernatants of positive clones selected through BV-ELISA were subjected to SDS-PAGE and immunoblotting by use of NCT-BV, Wild-BV, human wild-type nicastrin, and mutant forms of nicastrin in the presence of a 1×SDS-PAGE sample buffer. An anti-nicastrin N-terminal antibody (N-19) was employed as a positive control. In transient expression by use of animal cells, transfection into COS-7 cells was carried out by use of DEAE-dextran, and cells were recovered 48 hours after initiation of transfection. pEF6-NCT was employed for human wild-type nicastrin. Mutant nicastrin constructs (A312 and A694) were prepared from pEF6-NCT through long PCR (T. Tomita, et al., FEBS Lett. 520 (2002) 117-121).

Figure 3:
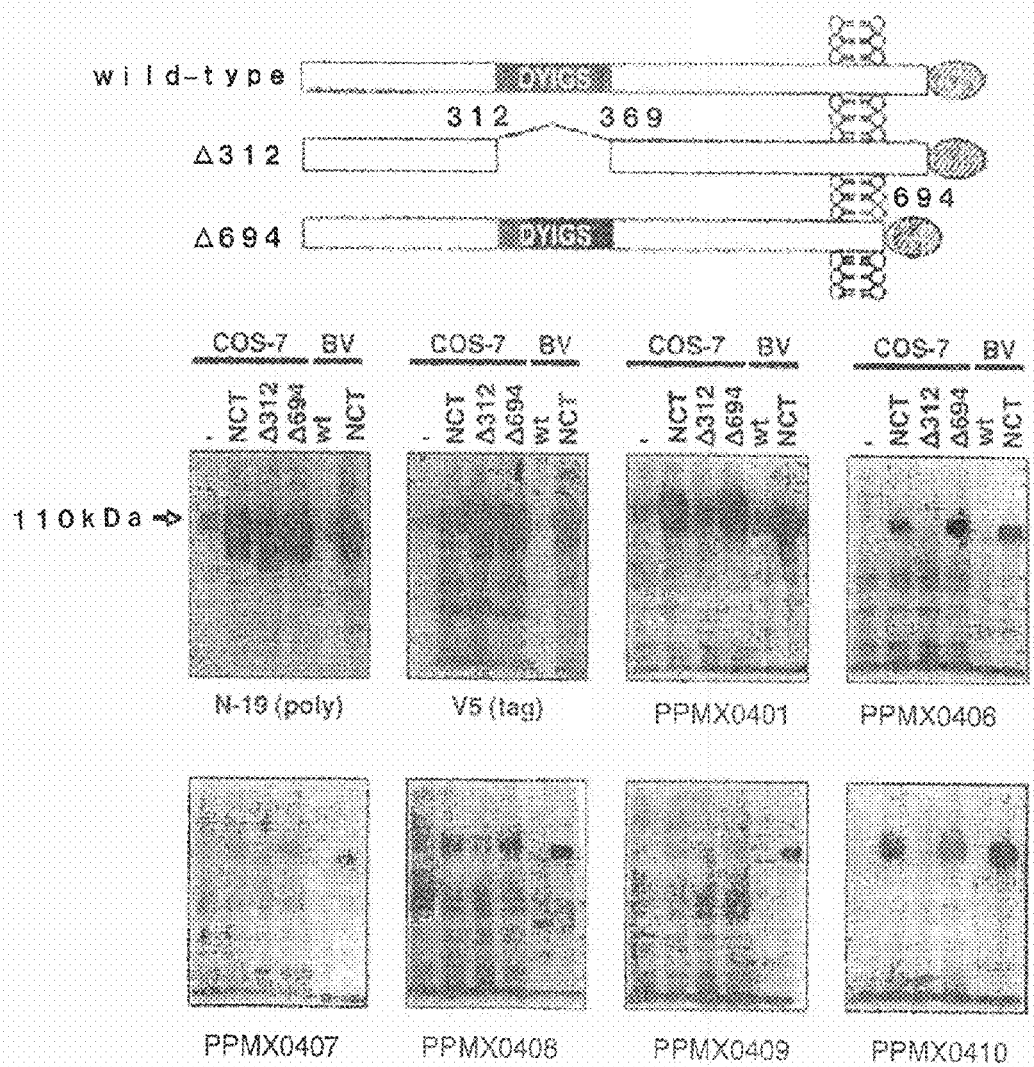
FIG. 3 shows results of western blot analysis of various forms of nicastrin expressed in COS-7 cells.

As a result, all the tested antibodies were found to recognize exogenously expressed human wild-type nicastrin. The anti-nicastrin N-terminal antibody (N-19) (i.e., a positive control) or an antibody to the C-terminal-added V5 tag recognized both wild-type nicastrin and mutant forms of nicastrin. In contrast, almost all the above-prepared antibodies (clones) (e.g., PPMX0401 and PPMX0410) did not recognize nicastrin Δ312 (FIG. 3). This suggests that the epitope site of each of the above-prepared antibodies is present in the extracellular domain of nicastrin.

Example 7

Preparation of Cells Constitutively Expressing Nicastrin

For the purpose of analysis of anti-nicastrin antibodies, NKO cells were transfected with pEF6-NCT by use of LipofectAmine (Invitrogen), and then NKO cells constitutively expressing human nicastrin (NKO/NCT cells) were selected in a medium containing 10 μg/mL blasticidin.

Example 8

Deglycosylation of Nicastrin

As has been known, nicastrin has, in the sequence thereof, 20 potential glycosylation sites and highly undergoes N-linked glycosylation (T. Tomita, et al., FEBS Lett. 520 (2002) 117-121; J. Y. Leem, et al., J. Biol. Chem. 277 (2002) 19236-19249; D. S. Yang, et al., J. Biol. Chem. 277 (2002) 28135-28142; and W. T. Kimberly, et al., J. Biol. Chem. 277 (2002) 35113-35117).

Nicastrin is classified, on the basis of the degree of glycosylation, into mature nicastrin (molecular weight: about 130 kDa) and immature nicastrin (molecular weight: about 110 kDa). Active γ-secretase complex contains only mature nicastrin. Among N-linked sugar chains, complex-type sugar chains are known to exhibit resistance to endoglycosidase H (Endo H) but to be cleaved by peptide: N-glycosidase F (PNGase). Therefore, through Endo H treatment, the molecular weight of complex-type glycosylated mature nicastrin is reduced to about 115 kDa, whereas the molecular weight of immature nicastrin having no complex-type sugar chain is reduced to about 80 kDa. In contrast, through PNGase F treatment, the molecular weights of both the mature nicastrin and immature nicastrin are reduced to about 80 kDa (D. S. Yang, et al., J. Biol. Chem. 277 (2002) 28135-28142, and W. T. Kimberly, et al., J. Biol. Chem. 277 (2002) 35113-35117).

In Example 8, a deglycosylation experiment was carried out for a purpose of epitopic analysis of anti-nicastrin antibodies.

Firstly, NKO/NCT cells were washed with PBS and then suspended in an RIPA buffer (50 mM Tris-HCl at pH 7.5, 1% Triton X-100, 1% sodium deoxycholate, 0.1% SDS, 150 mM NaCl), followed by inversion mixing at 4° C. for eight hours for lysis. Nicastrin was immunoprecipitated (IP) from the resultant lysate fraction by use of an anti-nicastrin. C-terminal antibody (N1660, Sigma), and the thus-precipitated nicastrin fraction was employed for the following analysis.

For Endo H or PNGase treatment, 200 mM citrate-NaOH (pH 5.8), 0.1% SDS, and 1% 2-mercaptoethanol were added to the nicastrin fraction, and the mixture was boiled at 95° C. for five minutes. 500 mU/mL Endoglycosidase H (Roche Applied Sciences) or 200 U/mL PNGase F (Roche Applied Sciences) was added to the mixture, and reaction was carried out at 37° C. overnight. Finally, a 5× sample buffer (¼ amount of the reaction mixture) was added to the reaction mixture, and the resultant mixture was boiled at 95° C. for five minutes, whereby reaction was terminated.

For neuraminidase (sialidase) treatment, 50 mM Na-acetate (pH 5.2), 2 mM $CaCl_2$, and 0.5% 2-mercaptoethanol were added to the nicastrin fraction, and the mixture was boiled at 95° C. for five minutes. 500 mU/mL Neuraminidase (Roche Applied Sciences) was added to the mixture, and reaction was carried out at 37° C. overnight. Finally, a 5× sample buffer (¼ amount of the reaction mixture) was added to the reaction mixture, and the resultant mixture was boiled at 95° C. for five minutes, whereby reaction was terminated.

Figure 4:
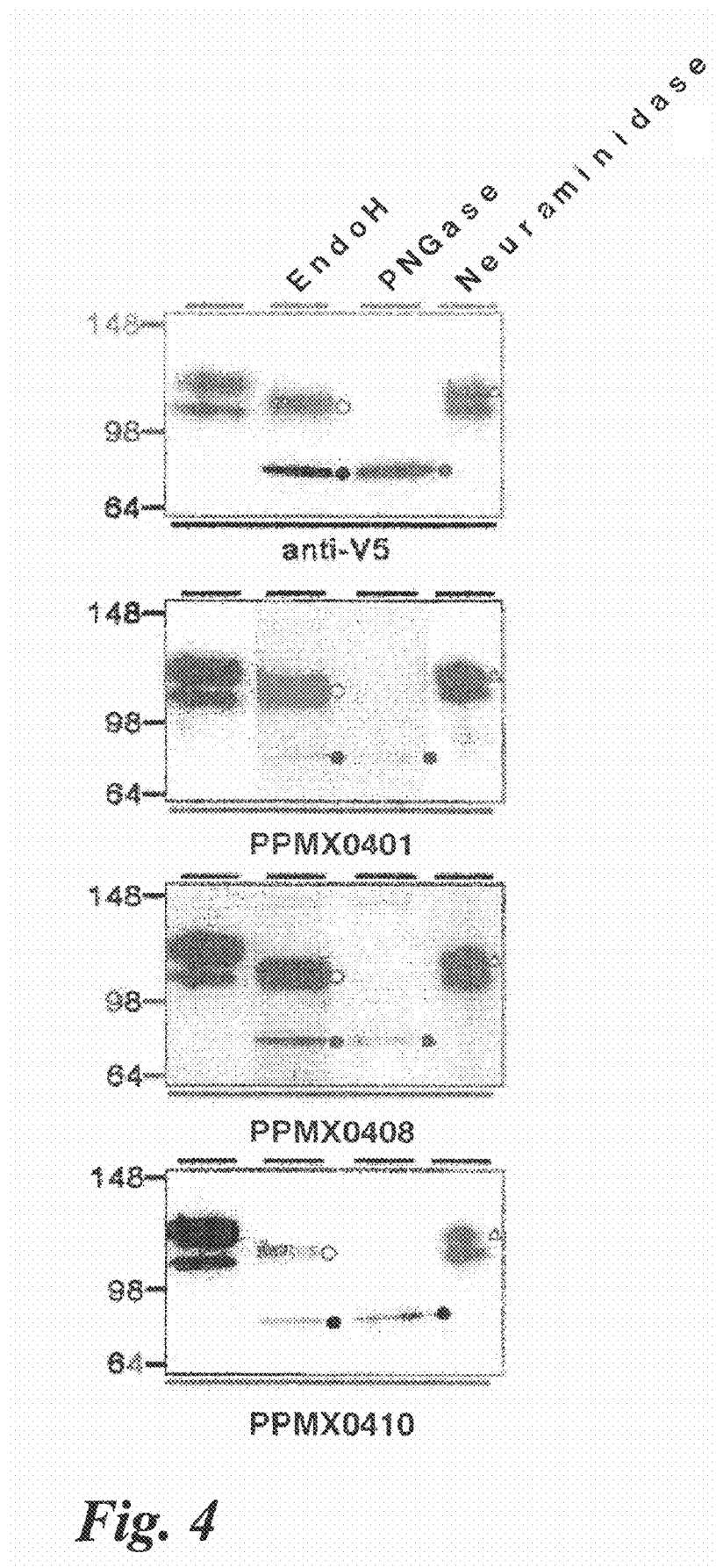
FIG. 4 shows results of an experiment for evaluating cross-reactivity of anti-nicastrin antibodies to deglycosylated nicastrin ("O" represents Endo H-resistant nicastrin; "black dot" represents completely deglycosylated nicastrin; and "Δ" represents neuraminidase-desialylated nicastrin).

Samples prepared through treatment with the aforementioned deglycosylation enzymes were subjected to western blot analysis. As a result, PPMX0401, PPMX0408, and PPMX0410 were found to exhibit cross-reactivity to deglycosylated nicastrin (FIG. 4). In FIG. 4, "O" represents Endo H-resistant nicastrin; "black dot" represents completely deglycosylated nicastrin; and "Δ" represents neuraminidase-desialylated nicastrin.

These data (in particular, the fact that each of the above-prepared antibodies recognized nicastrin which had been completely deglycosylated by PNGase F) suggest that the antibody binds to nicastrin by recognizing a peptide chain of the protein rather than a sugar chain thereof.

Example 9

Immunoprecipitation (IP) of Endogenous Nicastrin by use of Anti-Nicastrin Antibody HeLa cells were suspended in a cell homogenization buffer (10% glycerol-containing HEPES buffer (10 mM HEPES pH 7.4, 150 mM NaCl complete inhibitor cocktail (Roche Applied Sciences))) and homogenized by means of a homogenizer, followed by centrifugation at 1,500×g for 10 minutes. Subsequently, the resultant supernatant was centrifuged at 100,000×g for one hour, and the precipitate was employed as a HeLa cell membrane fraction. The cell membrane fraction was lysed in a 1% CHAPSO-containing HEPES buffer, to thereby yield a HeLa cell membrane lysate fraction. After IP of nicastrin from the lysate fraction by use of each of the above-prepared anti-nicastrin monoclonal antibodies, western blot analysis was carried out by use of various antibodies.

Figure 5:
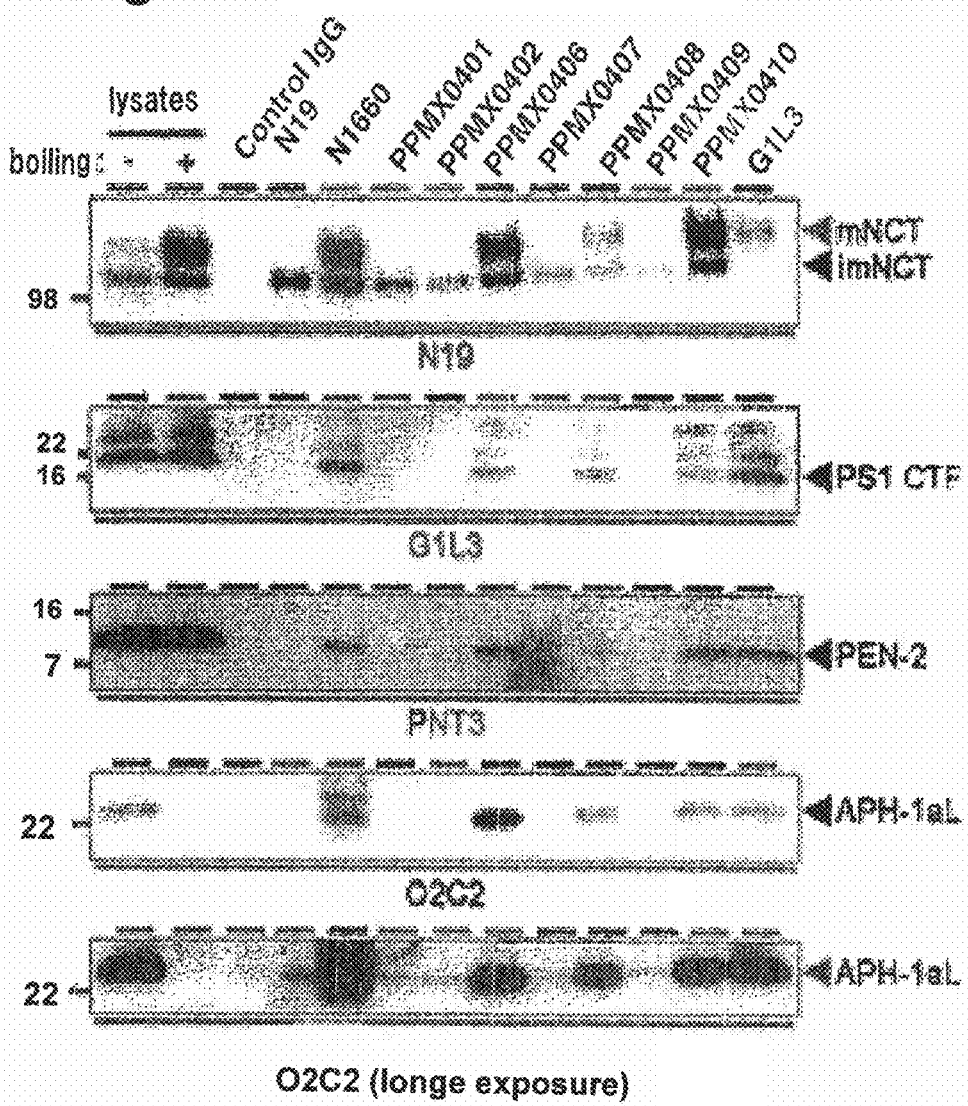
FIG. 5 shows results of IP of nicastrin from a soluble membrane fraction of HeLa cell by use of anti-nicastrin antibodies.

As a result, the above-prepared antibodies were found to be classified into two groups i.e., antibodies which allow IP of only immature nicastrin (PPMX0401, PPMX0402, PPMX0407, and PPMX0409) (first group); and antibodies which allow IP of both immature nicastrin and mature nicastrin (PPMX0406, PPMX0408, and PPMX0410) (second group) (FIG. 5). In the case of the antibodies of the second group (PPMX0406, PPMX0408, and PPMX0410), presenilin, PEN-2, and APH-1aL, which are components of the γ-secretase complex, were coprecipitated, whereas in the case of the antibodies of the first group (PPMX0401, PPMX0402, PPMX0407, and PPMX0409), only APH-1aL was precipitated in a small amount. As has been reported, immature nicastrin binds to APH-1 and forms a sub-complex before it forms a γ-secretase complex (M. LaVoie, et al., J. Biol. Chem. 278 (2003) 37213-37222). Therefore, conceivably, each of the antibodies of the first group (PPMX0401, PPMX0402, PPMX0407, and PPMX0409) binds specifically to immature nicastrin contained in a nicastrin-APH-1 sub-complex.

Figure 6:
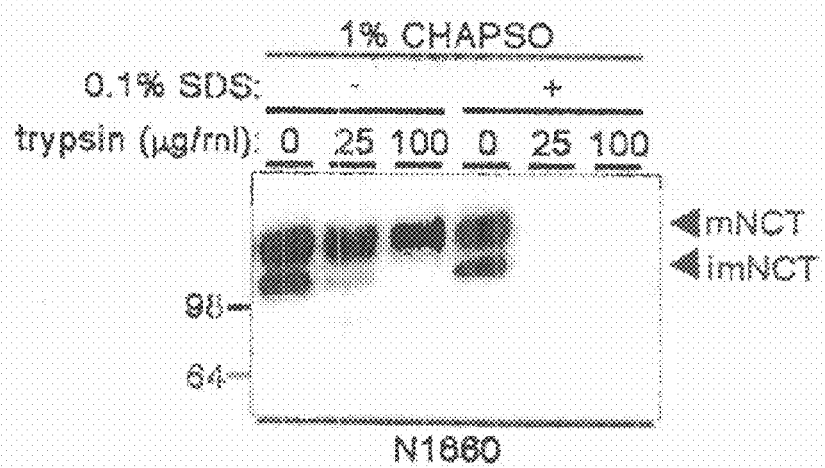
FIG. 6 shows results of treatment of a HeLa cell lysate with trypsin.

As has also been reported, the structure of the extracellular domain of nicastrin changes with formation of the γ-secretase complex (K. Shirotani, et al., J. Biol. Chem. 278 (2003) 16474-16477). When the HeLa cell 1% CHAPSO lysate was treated with trypsin, the extracellular domain of nicastrin exhibited resistance to trypsin. Therefore, conceivably, the extracellular domain of nicastrin maintains its structure in the γ-secretase complex in the presence of 1% CHAPSO (FIG. 6). Thus, the data of the IP experiment suggest that the epitope site of each antibody of the first group is masked through structural change of nicastrin, whereas the epitope site of each antibody of the second group may be exposed even after structural change of nicastrin.

Example 10

Immunostaining of Cultured Cells by Use of Anti-Nicastrin Monoclonal Antibody

Biochemical studies have reported that active γ-secretase containing mature nicastrin is localized to lipid rafts (Urano Y., Hayashi I., Isoo N., et al.: Association of active γ-secretase complex with lipid rafts. J. Lipid Res. 2005, 46: 904). In this Example, cultured cells were immunostained by use of the above-prepared antibodies, to thereby examine intracellular localization of nicastrin recognized by the antibodies. Intracellular localization of nicastrin was examined by use of HeLa cells and NKO cells. Cells were bonded, at an appropriate cell density, to a cover glass which had been coated with poly-D-lysine in advance, and the cells were washed with PBS and then fixed with PBS containing 4% paraformaldehyde. PBS containing 3% BSA was employed for blocking, and, in the case of permeation, Triton X-100 (final concentration: 0.1%) was further added. Each of the antibodies was diluted to an appropriate concentration with a blocking solution, and the thus-diluted antibody was reacted with the cells (at room temperature for three hours, or at 4° C. overnight). An anti-mouse or anti-rabbit immunoglobulin antibody bound to Alexa 488 or 546 was employed as a secondary antibody.

Figure 7:
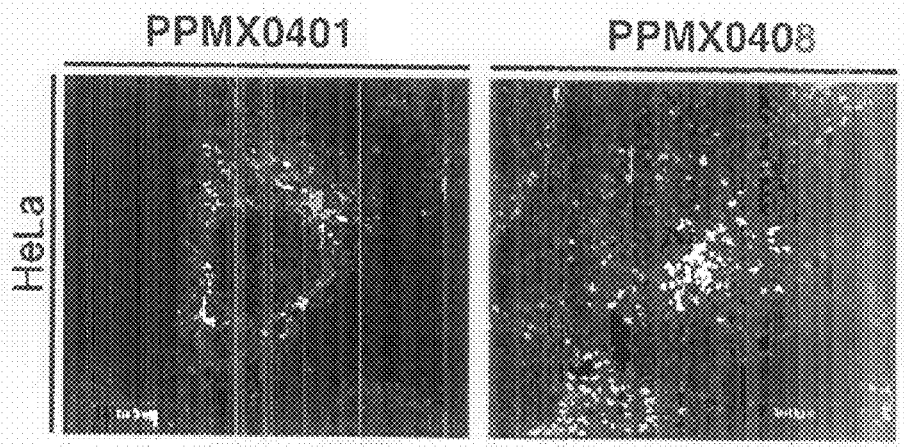
FIG. 7 shows results of immunostaining of HeLa cells by use of anti-nicastrin antibodies.
Figure 8:
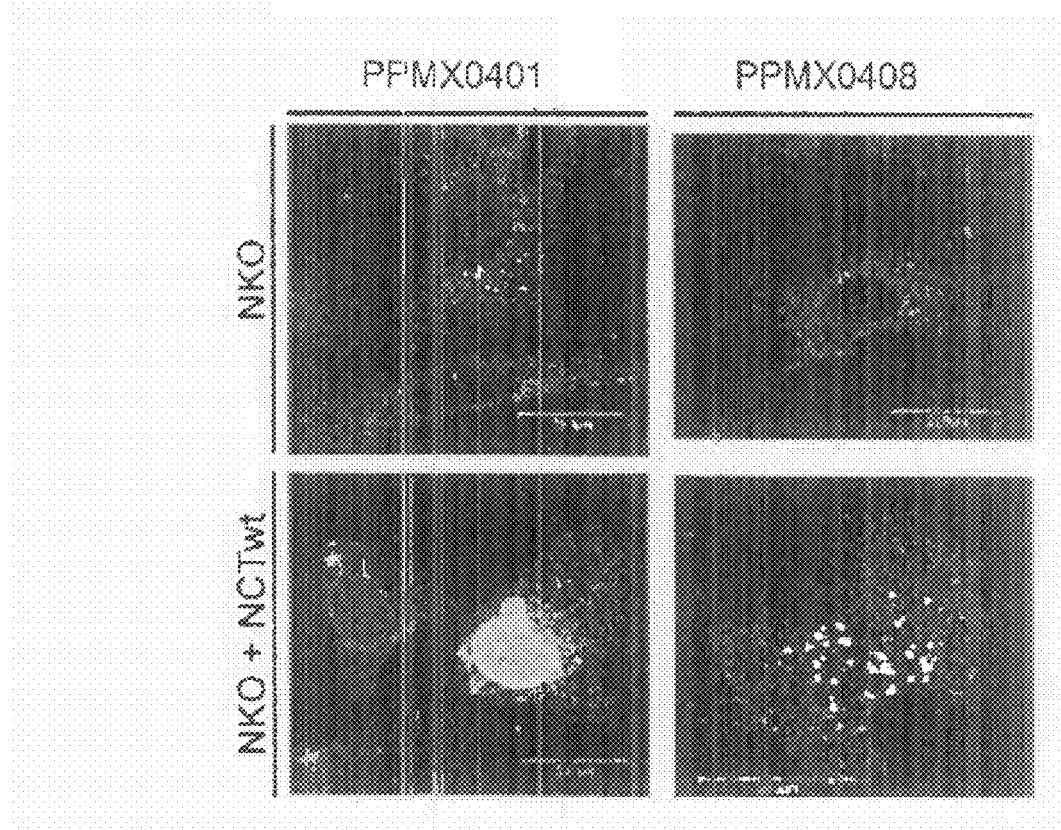
FIG. 8 shows results of immunostaining of NKO cells and NKO/NCT cells by use of anti-nicastrin antibodies.

As a result, in HeLa cells, a granular structure and the cell membrane were stained in the presence of PPMX0408, whereas such a structure was not stained in the presence of PPMX0401 (FIG. 7). In NKO cells, a granular structure was not stained in the presence of PPMX0408. However, when wild-type nicastrin was introduced into NKO cells, there was obtained a stained image similar to that obtained in the case of HeLa cells (FIG. 8). These data indicate that the granular structure stained in the presence of PPMX0408 is derived from nicastrin.

Figure 9:
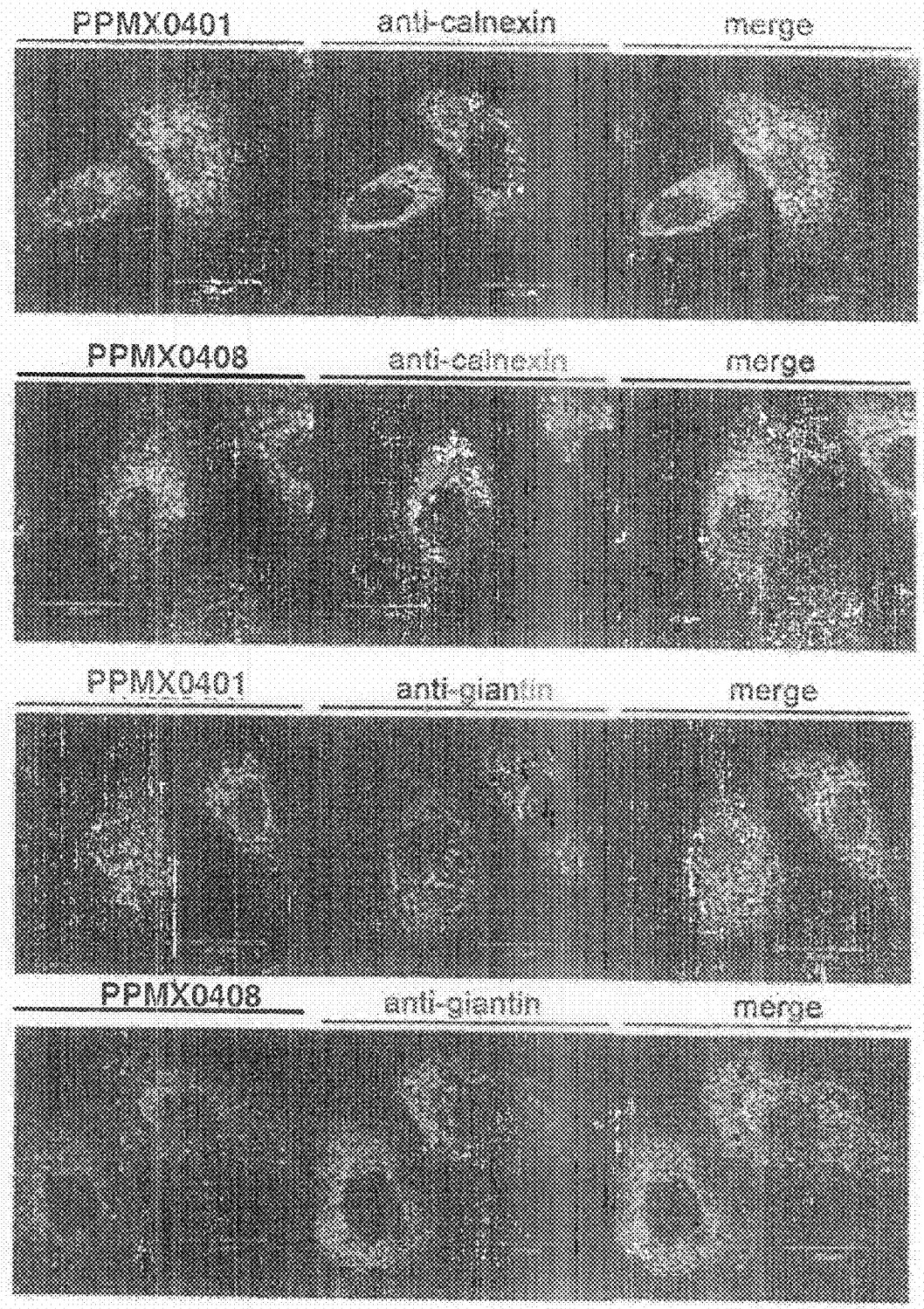
FIG. 9 shows results of co-staining by use of anti-nicastrin antibodies and antibodies to various marker proteins.
Figure 10:
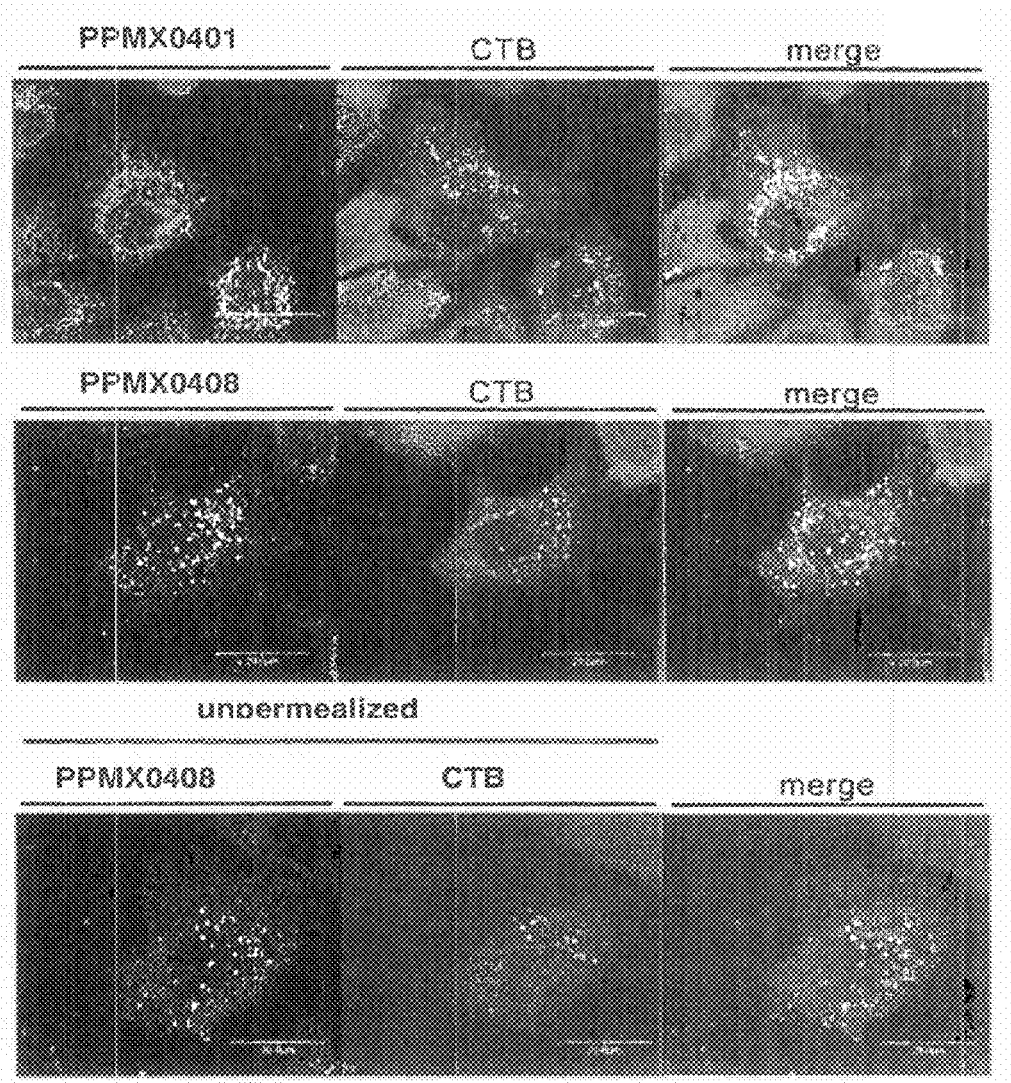
FIG. 10 shows results of co-staining by use of anti-nicastrin antibodies and cholera toxin subunit B (CTB).

Subsequently, in order to examine intracellular localization of the granular structure, co-staining was carried out by use of PPMX0408 and antibodies to various marker proteins. As a result, localization of the granular structure did not correspond to that of calnexin and giantin, which are marker proteins for endoplasmic reticulum and Golgi body, respectively (FIG. 9). In contrast, the results of staining in the presence of cholera toxin subunit B (CTB), which is used for staining of GM1 ganglioside present in lipid rafts, corresponded well to those of staining of the granular structure in the presence of PPMX0408. The results of staining in the presence of PPMX0401 did not correspond to those of staining in the presence of CTB (FIG. 10). Correspondence of localization similar to that described above was observed even under non-permeating conditions (i.e., no treatment with Triton X-100 during blocking) (FIG. 10). These data suggest that PPMX0408 recognizes mature nicastrin which is localized to lipid rafts (including cell membrane).

Example 11

Neutralization of Human Active γ-Secretase Activity by Use of Anti-Nicastrin Monoclonal Antibody Since PPMX0408 or PPMX0410 binds to mature nicastrin contained in active γ-secretase under the conditions where the γ-secretase complex is maintained, these antibodies are considered to affect γ-secretase activity. Therefore, a microsomal fraction of HeLa cells was lysed with 1% CHAPSO; each of the antibodies was added to an in vitro γ-secretase assay system employing an artificial substrate; and γ-secretase activity was determined on the basis of accumulation of de novo synthesized Aβ (Takasugi N., Tomita T., Hayashi I., Tsuruoka M., Niimura M., Takahashi Y., Thinakaran G., Iwatsubo T.: The role of presenilin cofactors in the γ-secretase complex. Nature 2003, 422: 438; and Takahashi Y., Hayashi I., Tominari Y., et al.: Sulindac sulfide is a non-competitive γ-secretase inhibitor that preferentially reduces Aβ 42 generation. J. Biol. Chem. 2003, 278: 18664).

Figure 11:
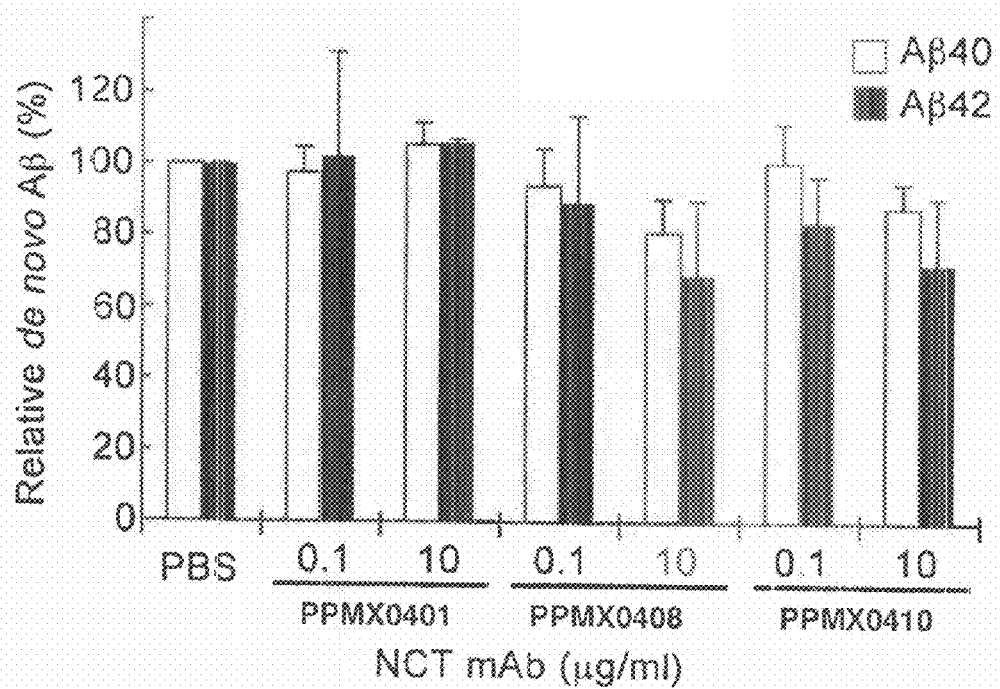
FIG. 11 shows an effect of anti-nicastrin antibodies on in vitro γ-secretase activity.

When PPMX0401 was added (final concentration: 10 μg/mL), γ-secretase activity was maintained at almost the same level as in the case where PBS was added. In contrast, when PPMX0408 or PPMX0410 was added (final concentration: 10 μg/mL), γ-secretase activity was inhibited by about 20%, as compared with the case where PBS was added (FIG. 11). This suggest that the antibodies which bind to mature nicastrin exhibit γ-secretase inhibitory activity.

Example 12

Effect of Anti-Nicastrin Monoclonal Antibody on Viability of Cancer Cell Lines

Figure 12:
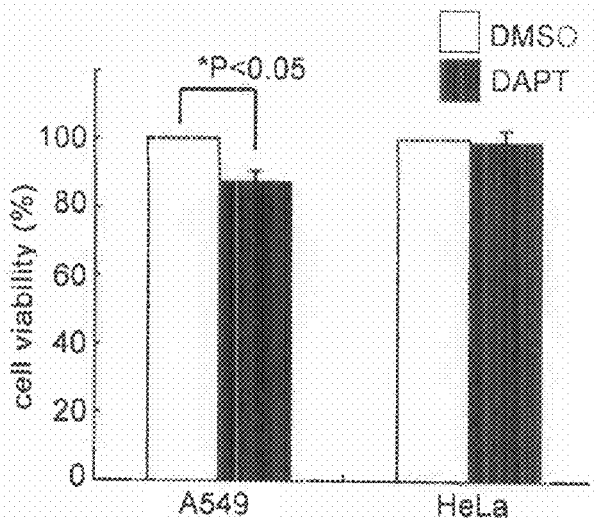
FIG. 12 shows an effect of DAPT on a viability of HeLa cells or A549 cells.
Figure 13:
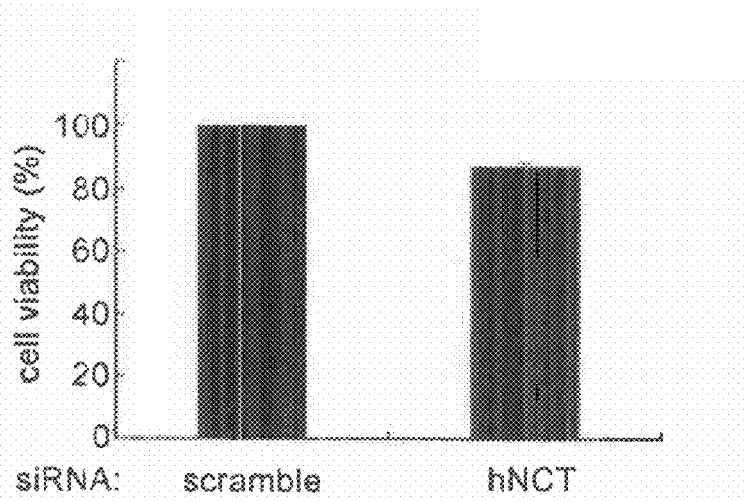
FIG. 13 shows an effect of inhibition of nicastrin expression on a viability of A549 cells.
Figure 14:
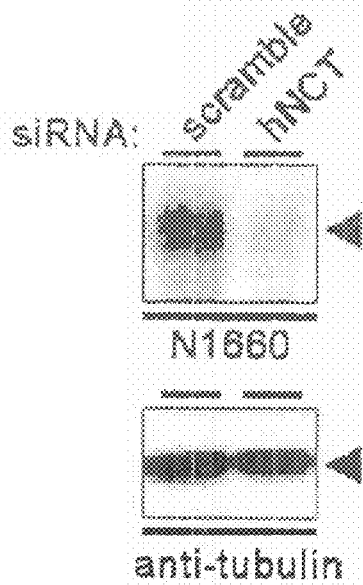
FIG. 14 shows results of inhibition of expression of endogenous nicastrin in A549 cells by siRNA.

Firstly, in order to identify a cancer cell line exhibiting Notch-signaling-dependent survival, the effect of a γ-secretase inhibitor DAPT (H F. Dovey, et al., J. Neurochem. 76 (2001) 173-181) on survival of HeLa cells or A549 cells was evaluated through the MTT method. HeLa cells or A549 cells ($5 \times 10^3$ cells) were inoculated onto a 96-well multiplate and treated with DAPT (final concentration: 100 μM) for 72 hours. After the 72-hour treatment, MTT diluted with PBS was added to the plate so that the final MTT concentration was 500 μg/mL, followed by culturing at 37° C. for three to four hours. Thereafter, stop solution (10% SDS, 0.01 M HCl) was added to the plate for termination of reaction, and the plate was allowed to stand still at 37° C. overnight, followed by dissolution of produced formazan. The formazan solution was uniformly mixed through pipetting, and absorbance was measured at 550 nm, to thereby calculate cell viability. As a result, the viability of DAPT-treated A549 cells was significantly lower than that of DAPT-untreated A549 cells. In contrast, no significant difference was observed in viability between DAPT-treated HeLa cells and DAPT-untreated HeLa cells (FIG. 12). Subsequently, in order to confirm that this reduction in cell viability was attributed to inhibition of γ-secretase activity, endogenous nicastrin of A549 cells was knocked down through treatment with nicastrin-corresponding short interference RNA (siRNA), and change in cell viability was determined. As a result, in the case of treatment with nicastrin siRNA, cell viability was reduced by about 20%, as compared with the case of treatment with siRNA having a random sequence (scramble) (FIG. 13). Under the nicastrin siRNA treatment conditions, expression of endogenous nicastrin was completely inhibited (FIG. 14). These data suggest that, unlike the case of HeLa cells, survival of A549 cells requires γ-secretase activity.

Figure 15:
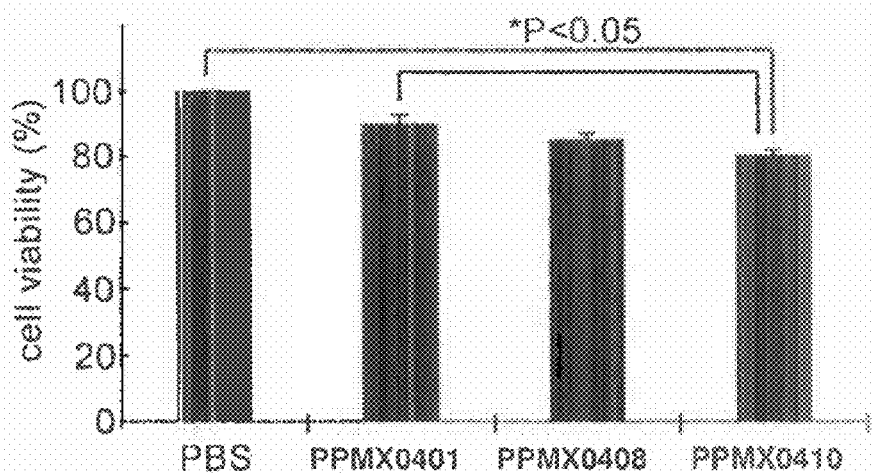
FIG. 15 shows an effect of anti-nicastrin antibodies on the viability of A549 cells.

Subsequently, the effect of the above-prepared antibodies on survival of A549 cells was examined. Each of the antibodies was added to A549 cells so that the final antibody concentration was 10 μg/mL, and, 96 hours after addition of the antibody, cell viability was determined through the MTT method. As a result, the viability of PPMX0410-treated A549 cells was significantly lower than that of antibody-untreated A549 cells or PPMX0401-treated A549 cells (FIG. 15). These data suggest that an antibody exhibiting γ-secretase inhibitory activity has an ability to inhibit proliferation of cancer cells exhibiting γ-secretase-dependent survival.

Example 13

Figure 16:
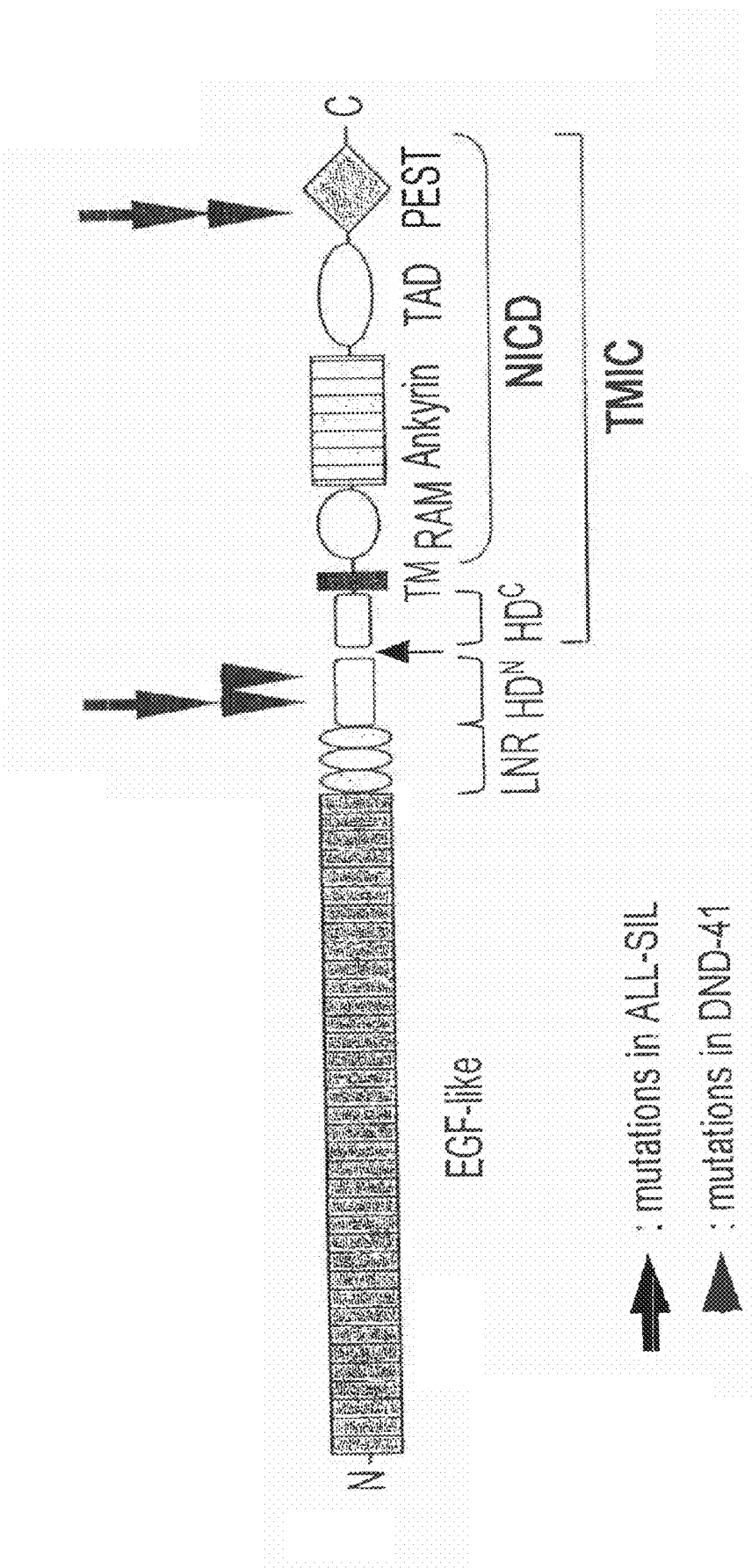
FIG. 16 shows mutation sites of Notch1 gene in various T-ALL-derived cells.

Effect of Anti-Nicastrin Monoclonal Antibody on Proliferation of Leukemia Cell Lines As has been reported, proliferation of cells of the following cell lines: TALL-1, ALL-SIL, and DND 41—which are isolated and established from patients with T-cell acute lymphoblastic leukemia (T-ALL)—requires Notch signaling (Weng, A. P., Ferrando, A. A., Lee, W., Morris, J. P. t., Silverman, L. B., Sanchez-Irizarry, C., Blacklow, S. C., Look, A. T. and Aster, J. C. (2004), Activating mutations of NOTCH1 in human T cell acute lymphoblastic leukemia. Science 306, 269-271). As has also been reported, in TALL-1 cells, somatic mutation is not found in the Notch1 gene, but in ALL-SIL cells or DND-41 cells, missense mutation occurs in the region (HDN) involved in interaction between an extracellular domain of Notch1 and TMIC (transmembrane-intracellular domain of Notch), and deletion (by mutation) occurs in the PEST region involved in degradation of NICD (Notch intracellular domain) (FIG. 16). Conceivably, mutation of the HDN region causes ligand-independent heterodimeric dissociation, shedding, and cleavage by γ-secretase, and deletion in the PEST region increases the stability of NICD, which induces abnormal activation of Notch signaling, thereby causing T-ALL.

Figure 17:
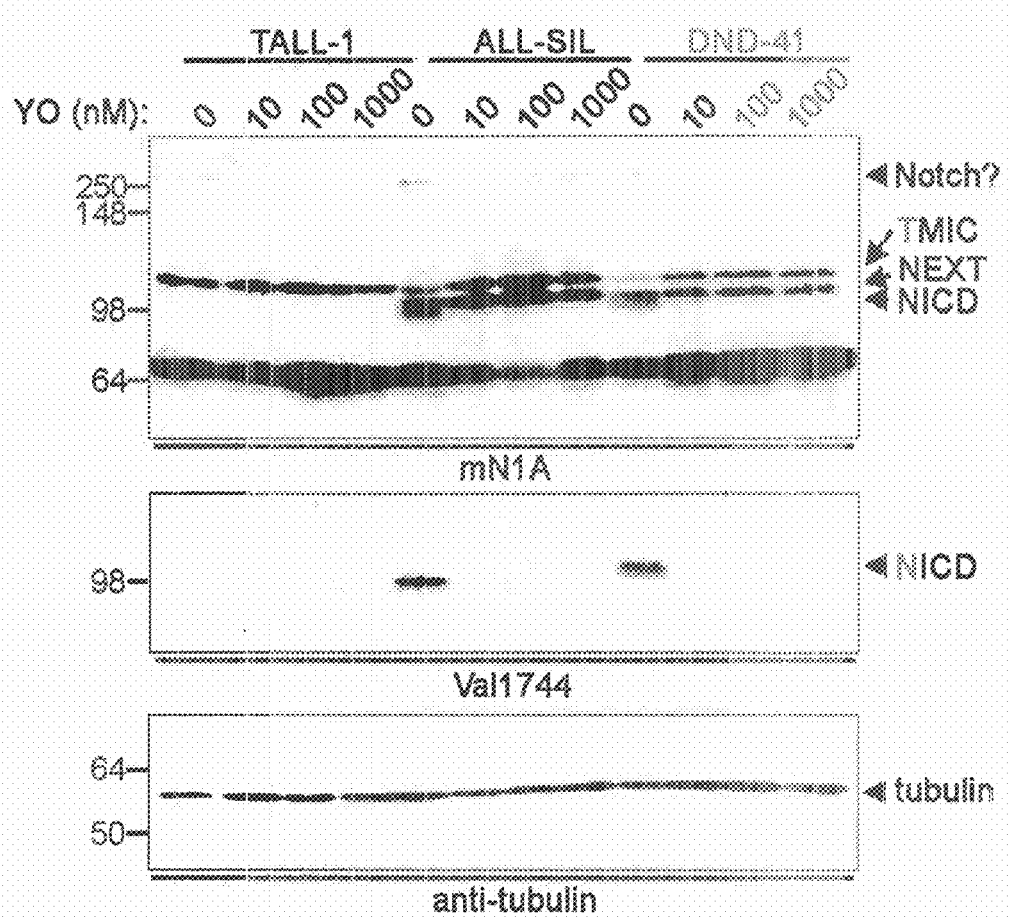
FIG. 17 shows results of western blot analysis of Notch1 gene products in various T-ALL-derived cell lysates.

Firstly, there was examined the effect of treatment of TALL-1, ALL-SIL, or DND-41 cells with a γ-secretase inhibitor on metabolism of Notch1. Through western blot analysis by use of an antibody mNIA to the intracellular ankyrin repeat domain of Notch1 (Chemicon, Cat #MAB5352), a band considered to be attributed to Notch1 TMIC was observed in the cases of all these types of cells. In the case of ALL-SIL cells or DND-41 cells, a band considered to be attributed to NEXT (Notch extracellular truncation) was observed at a position slightly below the TMIC band, and also a somewhat unclear band considered to be attributed to NICD was observed at a position below the NEXT band (FIG. 17). In the case of ALL-SIL cells or DND-41 cells, constitutive expression of NICD was determined by an antibody Val1744 (Cell Signaling, Cat #2421) specific to the cleaved N-terminal of NICD, but in the case of TALL-1 cells, expression of NICD was not observed. Subsequently, a γ-secretase inhibitor YO (concentration: 10, 100, or 1,000 nM) was added to the culture supernatant of each type of cells, and the cells were recovered 48 hours after addition of YO, followed by western blot analysis of the resultant lysate. As a result, in the case of YO treatment of ALL-SIL cells or DND-41 cells, NICD was found to disappear, and TMIC and NEXT were found to be accumulated (FIG. 17). These data suggest that Notch signaling is constitutively activated in at least both ALL-SIL cells and DND-41 cells.

Subsequently, the effect of YO treatment on proliferation of these cells was examined. Cells were inoculated onto a 96-well plate 5×10³ cells/well) and cultured at 37° C. overnight. Then, a γ-secretase inhibitor YO was added to the plate, followed by culturing for seven days. Thereafter, percent cell proliferation was determined by use of Alamar Blue (Serotec). Alamar Blue was added to the culture liquid in an amount of 1/10 that of the culture liquid, followed by culturing at 37° C. for four hours. Subsequently, the resultant culture supernatant was recovered. Fluorescence in the culture supernatant was measured by means of a plate reader (excitation wavelength: 530 nm, fluorescence wavelength: 590 nm), and percent cell proliferation was calculated by use of the following formula.

$$\text{cell proliferation}(\%) = \frac{A_{590}}{PC_{590}} \times 100$$

Figure 18:
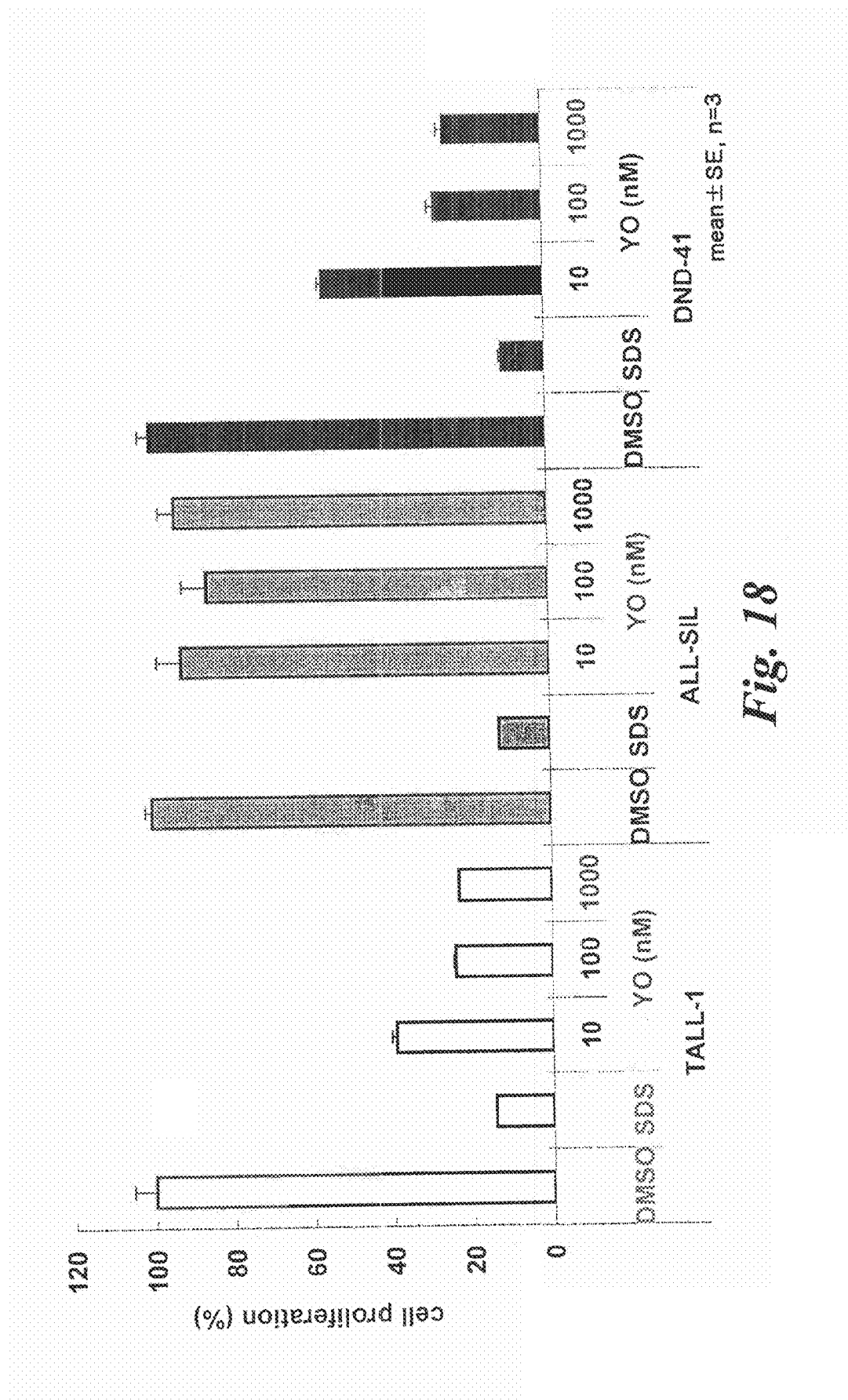
FIG. 18 shows an effect of a γ-secretase inhibitor YO on proliferation of various T-ALL-derived cells.

In the above formula, "A590" represents the absorbance of a sample at 590 nm, and "PC590" represents the absorbance of a positive control group (treated with PBS or DMSO) at 590 nm. As a result, proliferation of TALL-1 cells or DND-41 cells was found to be inhibited through YO treatment. Specifically, through treatment with 10 nM YO, proliferation of TALL-1 cells or DND-41 cells was inhibited by about 60% or about 50%, respectively, and, through treatment with 1,000 nM YO, proliferation of TALL-1 cells or DND-41 cells was inhibited by about 80% (FIG. 18). Unexpectedly, virtually no inhibition of cell proliferation was observed in ALL-SIL cells, in which NICD was found to disappear through YO treatment (as determined by western blot analysis). These data indicate that TALL-1 cells or DND-41 cells exhibit γ-secretase activity-dependent proliferation.

Figure 19:
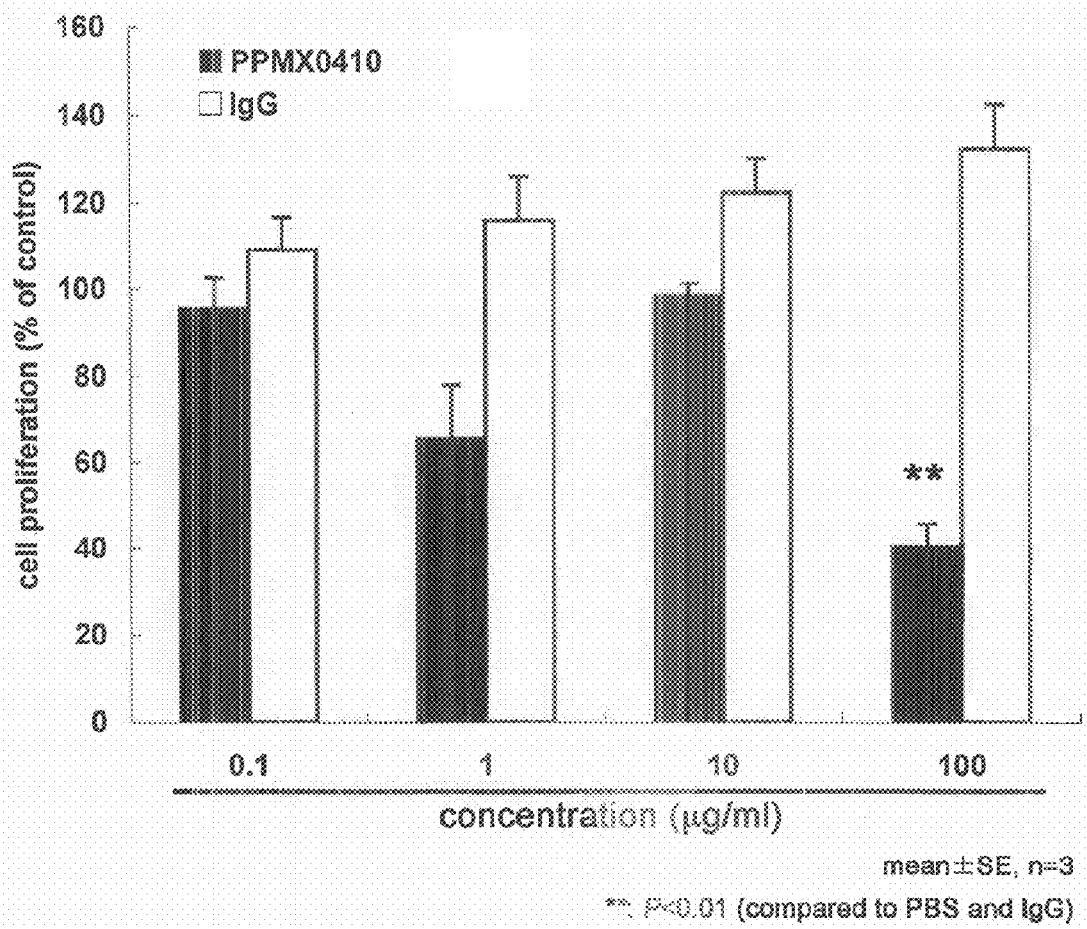
FIG. 19 shows an effect of an anti-nicastrin antibody on proliferation of DND-41 cells.

The above-obtained data suggest that, among the examined T-ALL-derived cells, at least DND-41 cells exhibit Notch signaling/γ-secretase activity-dependent proliferation. Therefore, the effect of PPMX0410 (i.e., an anti-nicastrin antibody) on proliferation of DND-41 cells was examined. PPMX0410 or a mouse IgG fraction (concentration: 0.1, 1, 10, or 100 µg/mL) was added to a DND-41 cell culture supernatant, followed by culturing for seven days. Thereafter, percent cell proliferation was determined, by use of Alamar Blue. As a result, percent cell proliferation tended to slightly increase in an IgG-fraction-concentration-dependent manner, but tended to lower through addition of PPMX0410. Specifically, proliferation of DND-41 cells was inhibited by about 60% through addition of 100 µg/mL PPMX0410 (FIG. 19). These data indicate that PPMX0410 inhibits Notch signaling/γ-secretase activity-dependent proliferation of T-ALL cells.

On the basis of these results, PPMX0410 was deposited with International Patent Organism Depositary, National Institute of Advanced Industrial Science and Technology (Central 6th, Tsukuba Center, 1-1-1, Higashi, Tsukuba, Ibaraki, Japan, Postal Code 305-8566) (deposition date: Apr. 21, 2006, accession number: FERM-AP 20895).

Example 14

Effect of Anti-Nicastrin Monoclonal Antibody in Inhibiting Binding Between Nicastrin and Substrate As has been reported, nicastrin may function as a substrate receptor in the γ-secretase complex (Shah S., Lee S F., Tabuchi K., Hao Y H., Yu C., LaPlant Q., Ball H., Dann C E 3rd, Sudhof T., Yu G.: Nicastrin functions as a γ-secretase-substrate receptor. Cell 2005, 122: 435).

Therefore, there was examined a possibility that PPMX0410 exhibits γ-secretase inhibitory activity by inhibiting interaction between γ-secretase and a substrate therefor.

Firstly, there was expressed, in Sf9 cells, nicastrin (having a V5-His tag sequence added at the carboxyl terminus) or Ni 00-FLAG (100 amino acid residues (No. 1711 to No. 1809) of Notch receptor including the intramembrane sequence (NH2-MVKSEPVEPPLPSQLHLVYVAAAAFVLL-FFVGCGVLLSRKRRRQHGQLWFPEGFKV SEA-SKKKRREPLGEDSVGLKPLKNASDGALMDDNQNEW GDEDLE-COOH) (SEQ ID NO: 15)) and having a FLAG-His tag (DYKDDDDKGSHJETHHHH) (SEQ ID NO: 16)) added at the carboxyl terminus), Lee S F., Shah S., Li H., Yu C., Han W., Yu G.: Mammalian APH-i interacts with presenilin and nicastrin and is required for intramembrane proteolysis of amyloid-3 precursor protein and Notch. J. Biol. Chem. 2002 277: 45013). Subsequently, a cell membrane fraction was prepared through the method described above in Example 9.

The resultant cell fraction was lysed in a HEPES buffer containing 1% CHAPSO, to thereby yield a nicastrin fraction or an N100 fraction.

The nicastrin fraction was mixed with PPMX0401 or PPMX0410 diluted to an appropriate concentration with PBS, and reaction was carried out at 4° C. overnight. Thereafter, the N100 fraction was added to the reaction mixture, followed by inversion mixing for three hours. A 1% CHAPSO-containing HEPES buffer was employed during mixing of the nicastrin fraction with the antibody, and a 0.5% CHAPSO-containing HEPES buffer was employed after addition of the N100 fraction.

Figure 20:
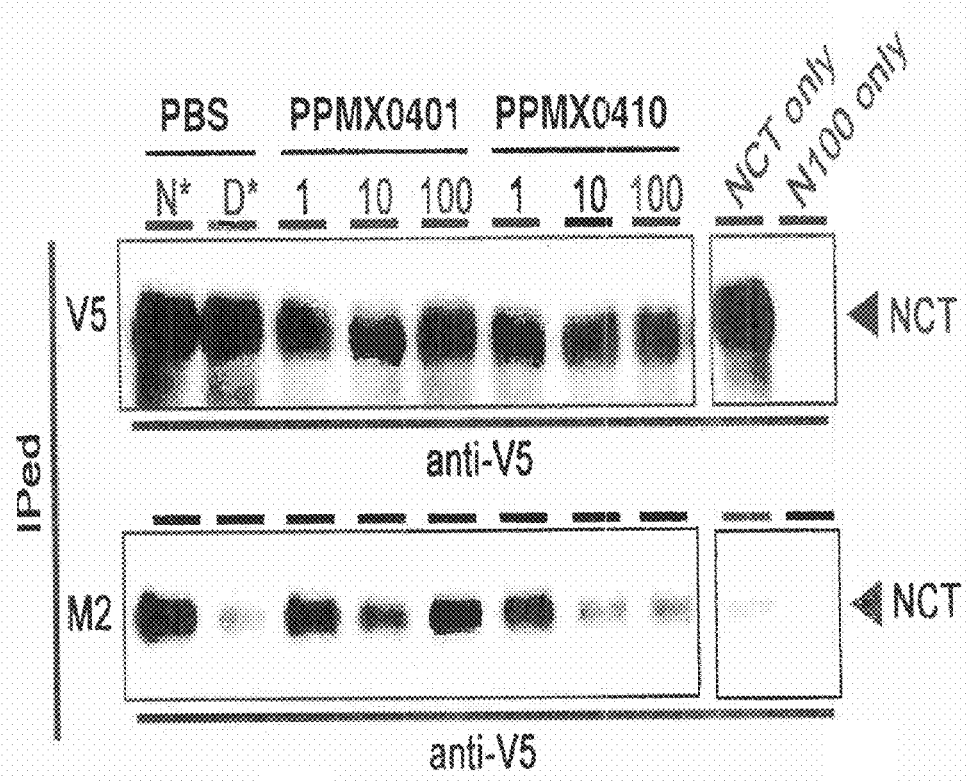
FIG. 20 shows results of western blot analysis of anti-nicastrin antibodies and a nicastrin-N100 fraction.

Nicastrin and N100-FLAG were coprecipitated from the resultant nicastrin-N100 fraction mixture by use of anti-V5-antibody-bound V5-agarose beads (SIGMA) or anti-FLAG-antibody-bound M2-agarose beads (SIGMA), and the precipitated fraction was subjected to western blot analysis by use of an anti-V5 antibody (FIG. 20).

In the case where a nicastrin fraction which had been denatured with 0.1% SDS in advance was employed, the amount of nicastrin precipitated by the M2-agarose beads (i.e., nicastrin bound to N100-FLAG) was reduced, as compared with the case where a native nicastrin fraction was employed (comparison between lanes "D" and "N" in FIG. 20).

Thus, this experiment system was considered to be applicable to detection of structure-dependent binding of nicastrin to N100.

Under the aforementioned conditions, PPMX0401 or PPMX0410 was added, and the amount of nicastrin precipitated by the M2-agarose beads was measured, followed by comparison of the resultant measurement data. In the case where PPMX0410 was added at a concentration of 10 or 100 μg/mL, the amount of nicastrin precipitated was found to be considerably reduced (FIG. 21). When the measurement data were normalized with the amount of nicastrin precipitated by the V5-agarose beads, PPMX0410 (at the aforementioned concentrations) was found to inhibit binding between nicastrin and N100-FLAG by about 60% (FIG. 21).

These data suggest that PPMX0410 inhibits γ-secretase activity by inhibiting binding between nicastrin and a substrate for the enzyme. Thus, these data suggest that an antibody exhibiting potent γ-secretase inhibitory activity can be selected on the basis of inhibition of binding between nicastrin and a substrate for the enzyme.

Example 15

Inhibition of γ-Secretase Activity by Anti-Nicastrin Antibody in Living Cells

An experiment was carried out by means of a GAL4-UAS system employing reporter cells, in order to determine whether or not PPMX0410—which inhibits γ-secretase activity in an in vitro reaction system—also inhibits cleavage mediated by γ-secretase activity in living cells.

C99 is a fragment produced through cleavage of APP (amyloid precursor protein) by BACE (β-site APP cleaving enzyme) and serves as a direct substrate for γ-secretase.

A preproenkephalin-derived signal peptide was inserted into C99, and GAL4 (i.e., a yeast-derived transcription factor) was inserted immediately downstream of the transmembrance domain of C99, to thereby prepare a construct (SC100G). The construct (SC100G) was subcloned into pcDNA3.1/Hygro vector (Invitroger).

GAL4/VP16 was bound to NΔE (including N99), in which deletion occurs in the extracellular domain of Notch receptor and which serves as a direct substrate for γ-secretase in a ligand-independent manner, to thereby prepare a construct (NΔEGV, Taniguchi Y., Karlstrom K., Lundkvist J., Mizutani T., Otaka A., Vestling M., Bernstein A., Donoviel D., Lendahl U., Honjo T.: Notch receptor cleavage depends on but is not directly executed by presenilins. Proc. Natl. Acad. Sci. U.S.A 2002, 99: 4014). The construct (NΔEGV) was subcloned into pcDNA3.1 vector (pcDNA3.1-NΔEGV).

A UAS sequence was inserted upstream of luciferase in pGL3(R2.2) vector (Promega), to thereby prepare a construct (UAS-luc), and the construct was employed as a reporter construct. eGFP was subcloned into pcDNA3 (Invitrogen), and the thus-prepared pcDNA3-eGFP was employed as a control vector for monitoring the number of cells. HEK293 cells were transfected with pcDNA3.1-SC100G and UAS-luc, or transfected with pcDNA3.1-NΔEGV, UAS-luc, and pcDNA3-eGFP by use of Lipofectamine 2000 (Invitrogen). Cells constitutively expressing nicastrin (HEK/SC100G cells or HEK/NΔEGV cells) were selected by use of an antibiotic-resistant marker (Hygromycin (Wako Pure Chemical Industries, Ltd.) or G418 (CALBIOCHEM), respectively).

HEK/SC100G cells or HEK/NΔEGV cells were inoculated into a 48-well multiplate ($2.5 \times 10^4$ cells). After culturing at 37° C. for 24 hours, PBS or PPMX0410 diluted to an appropriate concentration with PPS was added to the plate. Cells treated with DMSO or DAPT (final concentration: 10 μM) (i.e., γ-secretase-activity-inhibiting control) were also provided. After culturing at 37° C. for 36 hours, n-butyric acid (final concentration: 10 mM) was added for induction of transgene expression. After culturing for 12 hours, cells and a culture supernatant were recovered, and the amount of Aβ was determined through a reporter assay or ELISA.

The recovered cells were lysed in a lysis buffer (Promega), and the resultant lysate was subjected to the reporter assay. PicaGene (Toyo Ink Mfg. Co., Ltd.) was employed as a luminescent substrate. The amount of luciferase luminescence was normalized by the concentration of protein (in the case of HEK/SC100G cells), or by the amount of eGFP luminescence (in the case of HEK/NΔEGV cells), to thereby yield relative light unit (RLU). The amount of Aβ secreted in the culture supernatant of HEK/SC100G cells was determined through ELISA, and the thus-determined Aβ amount was normalized by the concentration of protein similar to the case of normalization of the amount of luciferase luminescence.

Figure 22:
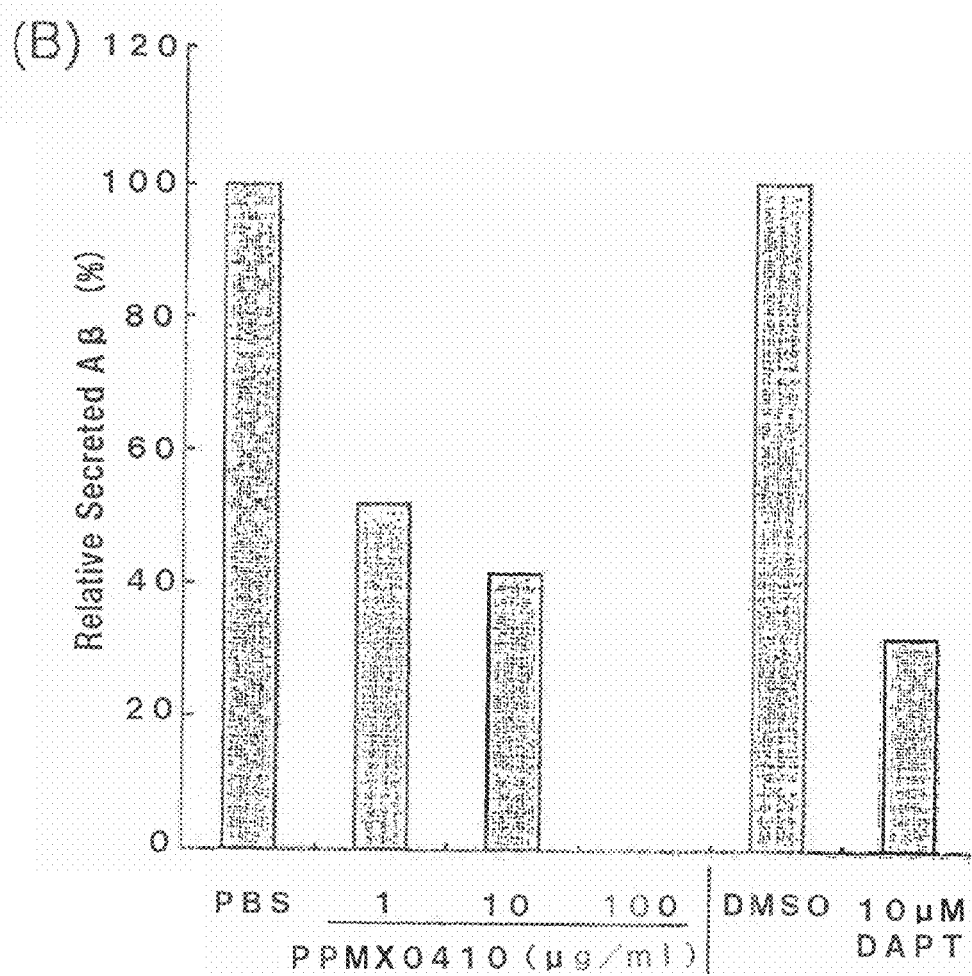
FIG. 22A shows an effect of an anti-nicastrin antibody on inhibition of γ-secretase activity in living cells.
FIG. 22B shows an effect of an anti-nicastrin antibody on inhibition of γ-secretase activity in living cells.
FIG. 22C shows an effect of an anti-nicastrin antibody on inhibition of γ-secretase activity in living cells.

As a result, PPMX0410 was found to inhibit, in a concentration-dependent manner, reporter activity (FIG. 22A) and Aβ secretion (FIG. 22B) in HEK/SC100G cells, and reporter activity (FIG. 22C) in HEK/NΔEGV cells. Under the aforementioned conditions, DAPT (i.e., a γ-secretase inhibitor) was found to inhibit reporter activity in both HEK/SC100G cells and HEK/NΔEGV cells.

These data indicate that PPMX0410 also inhibits γ-secretase activity in living cells and inhibits intramembrane protein cleavage in APP or Notch receptor.

The method described in Example 14 can be employed for high throughput screening. Therefore, the method is considered applicable to selection of an antibody exhibiting potent γ-secretase inhibitory activity.

The invention claimed is:

1. A method for treatment of a nicastrin-expressing cancer that is γ-secretase-dependent, comprising administering an anti-nicastrin antibody, which is PPMX0410 (FERM-AP20895) to a subject in need thereof, wherein the cancer is lung cancer or T-cell acute lymphoblastic leukemia.

2. The method as described in claim 1, wherein the cancer is T-cell acute lymphoblastic leukemia.

* * * * *

SEQUENCE LISTING

<160> NUMBER OF SEQ ID NOS: 19

<210> SEQ ID NO 1
<211> LENGTH: 2944
<212> TYPE: DNA
<213> ORGANISM: Homo sapiens

<400> SEQUENCE: 1
cgcctggaaa cacgaacttc cggtctctta ggctccgggc cacagagacg gtgtcagtgg      60
tagcctagag aggccgctaa cagacaggag ccgaacgggg gcttccgctc agcagagagg     120

-continued

```
caagatggct acggcagggg gtggctctgg ggctgacccg ggaagtcggg gtctccttcg      180
ccttctgtct ttctgcgtcc tactagcagg tttgtgcagg ggaaactcag tggagaggaa      240
gatatatatc cccttaaata aaacagctcc ctgtgttcgc ctgctcaacg ccactcatca      300
gattggctgc cagtcttcaa ttagtggaga cacaggggtt atccacgtag tagagaaaga      360
ggaggaccta cagtgggtat tgactgatgg ccccaacccc ccttacatgg ttctgctgga      420
gagcaagcat tttaccaggg atttaatgga gaagctgaaa gggagaacca gccgaattgc      480
tggtcttgca gtgtccttga ccaagcccag tcctgcctca ggcttctctc ctagtgtaca      540
gtgcccaaat gatgggtttg gtgtttactc caattcctat gggccagagt ttgctcactg      600
cagagaaata cagtggaatt cgctgggcaa tggtttggct tatgaagact ttagtttccc      660
catctttctt cttgaagatg aaaatgaaac caaagtcatc aagcagtgct atcaagatca      720
caacctgagt cagaatggct cagcaccaac cttcccacta tgtgccatgc agctcttttc      780
acacatgcat gctgtcatca gcactgccac ctgcatgcgg cgcagctcca tccaaagcac      840
cttcagcatc aacccagaaa tcgtctgtga cccctgtct gattacaatg tgtggagcat      900
gctaaagcct ataaatacaa ctgggacatt aaagcctgac gacagggttg tggttgctgc      960
cacccggctg gatagtcgtt ccttttctg gaatgtggcc ccaggggctg aaagcgcagt     1020
ggcttccttt gtcacccagc tggctgctgc tgaagctttg caaaaggcac ctgatgtgac     1080
caccctgccc cgcaatgtca tgtttgtctt ctttcaaggg gaaacttttg actacattgg     1140
cagctcgagg atggtctacg atatggagaa gggcaagttt cccgtgcagt tagagaatgt     1200
tgactcattt gtggagctgg acaggtggc cttaagaact tcattagagc tttggatgca     1260
cacagatcct gtttctcaga aaatgagtc tgtacggaac caggtggagg atctcctggc     1320
cacattggag aagagtggtg ctggtgtccc tgctgtcatc ctcaggaggc caaatcagtc     1380
ccagcctctc ccaccatctt ccctgcagcg atttcttcga gctcgaaaca tctctggcgt     1440
tgttctggct gaccactctg gtgccttcca taacaaatat taccagagta tttacgacac     1500
tgctgagaac attaatgtga gctatcccga atggctgagc cctgaagagg acctgaactt     1560
tgtaacagac actgccaagg ccctggcaga tgtggccacg gtgctgggac gtgctctgta     1620
tgagcttgca ggaggaacca acttcagcga cacagttcag gctgatcccc aaacggttac     1680
ccgcctgctc tatgggttcc tgattaaagc caacaactca tggttccagt ctatcctcag     1740
gcaggaccta aggtcctact gggtgacgg gcctcttcaa cattcatcg ctgtctccag     1800 ccccaccaac accacttatg ttgtacagta tgccttggca aatttgactg gcacagtggt     1860
caacctcacc cgagagcagt gccaggatcc aagtaaagtc ccaagtgaaa caaggatct     1920 gtatgagtac tcatgggtcc agggccctt gcattctaat gagacggacc gactcccccg     1980
gtgtgtgcgt tctactgcac gattagccag ggccttgtct cctgcctttg aactgagtca     2040
gtggagctct actgaatact ctacatggac tgagagccgc tggaaagata tccgtgcccg     2100
gatatttctc atcgccagca aagagcttga gttgatcacc ctgacagtgg gcttcggcat     2160
cctcatcttc tccctcatcg tcacctactg catcaatgcc aaagctgatg tccttttcat     2220
tgctccccgg gagccaggag ctgtgtcata ctgaggagga ccccagcttt tcttgccagc     2280
tcagcagttc acttcctaga gcatctgtcc cactgggaca caaccactaa tttgtcactg     2340
gaacctccct gggcctgtct cagattggga ttaacataaa agagtggaac tatccaaaag     2400 agacaggag aaataaataa attgcctccc ttcctccgct cccctttccc atcacccctt     2460
ccccatttcc tcttccttct ctactcatgc cagattttgg gattacaaat agaagcttct     2520
```

-continued

```
tgctcctgtt taactcccta gttacccacc ctaatttgcc cttcaggacc cttctacttt    2580
ttccttcctg ccctgtacct ctctctgctc ctcaccccca ccctgtacc cagccacctt    2640 cctgactggg aaggacataa aaggtttaat gtcagggtca aactacattg agccctgag    2700 gacagggca tctctgggct gagcctactg tctccttccc actgtccttt ctccaggccc    2760
tcagatggca cattagggtg ggcgtgctgc gggtgggtat cccacctcca gcccacagtg    2820
ctcagttgta cttttattat agctgtaata tctatttttg tttttgtctt tttccttat    2880 tcttttttgta aatatatata taatgagttt cattaaaata gattatccca cacgaaaaaa    2940
aaaa                                                                  2944
```

<210> SEQ ID NO 2
<211> LENGTH: 709
<212> TYPE: PRT
<213> ORGANISM: Homo sapiens

<400> SEQUENCE: 2

```
Met Ala Thr Ala Gly Gly Gly Ser Gly Ala Asp Pro Gly Ser Arg Gly
 1               5                   10                  15

Leu Leu Arg Leu Leu Ser Phe Cys Val Leu Leu Ala Gly Leu Cys Arg
             20                  25                  30

Gly Asn Ser Val Glu Arg Lys Ile Tyr Ile Pro Leu Asn Lys Thr Ala
         35                  40                  45

Pro Cys Val Arg Leu Leu Asn Ala Thr His Gln Ile Gly Cys Gln Ser
     50                  55                  60

Ser Ile Ser Gly Asp Thr Gly Val Ile His Val Val Glu Lys Glu Glu
 65                  70                  75                  80

Asp Leu Gln Trp Val Leu Thr Asp Gly Pro Asn Pro Pro Tyr Met Val
                 85                  90                  95

Leu Leu Glu Ser Lys His Phe Thr Arg Asp Leu Met Glu Lys Leu Lys
            100                 105                 110

Gly Arg Thr Ser Arg Ile Ala Gly Leu Ala Val Ser Leu Thr Lys Pro
        115                 120                 125

Ser Pro Ala Ser Gly Phe Ser Pro Ser Val Gln Cys Pro Asn Asp Gly
    130                 135                 140

Phe Gly Val Tyr Ser Asn Ser Tyr Gly Pro Glu Phe Ala His Cys Arg
145                 150                 155                 160

Glu Ile Gln Trp Asn Ser Leu Gly Asn Gly Leu Ala Tyr Glu Asp Phe
                165                 170                 175

Ser Phe Pro Ile Phe Leu Leu Glu Asp Glu Asn Glu Thr Lys Val Ile
            180                 185                 190

Lys Gln Cys Tyr Gln Asp His Asn Leu Ser Gln Asn Gly Ser Ala Pro
        195                 200                 205

Thr Phe Pro Leu Cys Ala Met Gln Leu Phe Ser His Met His Ala Val
    210                 215                 220

Ile Ser Thr Ala Thr Cys Met Arg Arg Ser Ser Ile Gln Ser Thr Phe
225                 230                 235                 240

Ser Ile Asn Pro Glu Ile Val Cys Asp Pro Leu Ser Asp Tyr Asn Val
                245                 250                 255

Trp Ser Met Leu Lys Pro Ile Asn Thr Thr Gly Thr Leu Lys Pro Asp
            260                 265                 270

Asp Arg Val Val Val Ala Ala Thr Arg Leu Asp Ser Arg Ser Phe Phe
        275                 280                 285

Trp Asn Val Ala Pro Gly Ala Glu Ser Ala Val Ala Ser Phe Val Thr
```

-continued

```
            290                 295                 300
Gln Leu Ala Ala Ala Glu Ala Leu Gln Lys Ala Pro Asp Val Thr Thr
305                 310                 315                 320

Leu Pro Arg Asn Val Met Phe Val Phe Phe Gln Gly Glu Thr Phe Asp
                325                 330                 335

Tyr Ile Gly Ser Ser Arg Met Val Tyr Asp Met Glu Lys Gly Lys Phe
                340                 345                 350

Pro Val Gln Leu Glu Asn Val Asp Ser Phe Val Glu Leu Gly Gln Val
                355                 360                 365

Ala Leu Arg Thr Ser Leu Glu Leu Trp Met His Thr Asp Pro Val Ser
370                 375                 380

Gln Lys Asn Glu Ser Val Arg Asn Gln Val Glu Asp Leu Leu Ala Thr
385                 390                 395                 400

Leu Glu Lys Ser Gly Ala Gly Val Pro Ala Val Ile Leu Arg Arg Pro
                405                 410                 415

Asn Gln Ser Gln Pro Leu Pro Pro Ser Ser Leu Gln Arg Phe Leu Arg
                420                 425                 430

Ala Arg Asn Ile Ser Gly Val Val Leu Ala Asp His Ser Gly Ala Phe
            435                 440                 445

His Asn Lys Tyr Tyr Gln Ser Ile Tyr Asp Thr Ala Glu Asn Ile Asn
            450                 455                 460

Val Ser Tyr Pro Glu Trp Leu Ser Pro Glu Glu Asp Leu Asn Phe Val
465                 470                 475                 480

Thr Asp Thr Ala Lys Ala Leu Ala Asp Val Ala Thr Val Leu Gly Arg
                485                 490                 495

Ala Leu Tyr Glu Leu Ala Gly Gly Thr Asn Phe Ser Asp Thr Val Gln
                500                 505                 510

Ala Asp Pro Gln Thr Val Thr Arg Leu Leu Tyr Gly Phe Leu Ile Lys
            515                 520                 525

Ala Asn Asn Ser Trp Phe Gln Ser Ile Leu Arg Gln Asp Leu Arg Ser
            530                 535                 540

Tyr Leu Gly Asp Gly Pro Leu Gln His Tyr Ile Ala Val Ser Ser Pro
545                 550                 555                 560

Thr Asn Thr Thr Tyr Val Val Gln Tyr Ala Leu Ala Asn Leu Thr Gly
                565                 570                 575

Thr Val Val Asn Leu Thr Arg Glu Gln Cys Gln Asp Pro Ser Lys Val
                580                 585                 590

Pro Ser Glu Asn Lys Asp Leu Tyr Glu Tyr Ser Trp Val Gln Gly Pro
            595                 600                 605

Leu His Ser Asn Glu Thr Asp Arg Leu Pro Arg Cys Val Arg Ser Thr
610                 615                 620

Ala Arg Leu Ala Arg Ala Leu Ser Pro Ala Phe Glu Leu Ser Gln Trp
625                 630                 635                 640

Ser Ser Thr Glu Tyr Ser Thr Trp Thr Glu Ser Arg Trp Lys Asp Ile
                645                 650                 655

Arg Ala Arg Ile Phe Leu Ile Ala Ser Lys Glu Leu Glu Leu Ile Thr
                660                 665                 670

Leu Thr Val Gly Phe Gly Ile Leu Ile Phe Ser Leu Ile Val Thr Tyr
                675                 680                 685

Cys Ile Asn Ala Lys Ala Asp Val Leu Phe Ile Ala Pro Arg Glu Pro
            690                 695                 700

Gly Ala Val Ser Tyr
705
```

<210> SEQ ID NO 3
<211> LENGTH: 8064
<212> TYPE: DNA
<213> ORGANISM: Mus musculus
<220> FEATURE:
<221> NAME/KEY: CDS
<222> LOCATION: (79)..(7671)

<400> SEQUENCE: 3

| | |
|---|---|
| gtggtgtgcg tcaacgtccg atccccgccg gccaccccaa gaggccgccg ccgggctgcg | 60 |
| ggcagctggc gagcaggc atg cca cgg ctc ctg acg ccc ctt ctc tgc cta<br>                           Met Pro Arg Leu Leu Thr Pro Leu Leu Cys Leu<br>                            1               5               10 | 111 |
| acg ctg ctg ccc gcg cgc gcc gca aga ggc ttg aga tgc tcc cag cca<br>Thr Leu Leu Pro Ala Arg Ala Ala Arg Gly Leu Arg Cys Ser Gln Pro<br>         15                    20                    25 | 159 |
| agt ggg acc tgc ctg aat gga ggt agg tgc gaa gtg gcc agc ggc act<br>Ser Gly Thr Cys Leu Asn Gly Gly Arg Cys Glu Val Ala Ser Gly Thr<br>  30                      35                    40 | 207 |
| gaa gcc tgt gtt gcc agc ggc agc ttt gtg ggc caa cga tgc cag gac<br>Glu Ala Cys Val Ala Ser Gly Ser Phe Val Gly Gln Arg Cys Gln Asp<br>45                    50                    55 | 255 |
| ccc aat cct tgc ctc agc aca cgg tgt aag aat gct gga acg tgc tat<br>Pro Asn Pro Cys Leu Ser Thr Arg Cys Lys Asn Ala Gly Thr Cys Tyr<br>60                  65                   70                    75 | 303 |
| gtt gtg gac cat ggt ggc atc gtg gac tat gcc tgc agc tgt ccc ctg<br>Val Val Asp His Gly Gly Ile Val Asp Tyr Ala Cys Ser Cys Pro Leu<br>                80                    85                    90 | 351 |
| ggt ttc tct ggg ccc ctc tgc ctg aca cct ctg gac aag ccc tgc ctg<br>Gly Phe Ser Gly Pro Leu Cys Leu Thr Pro Leu Asp Lys Pro Cys Leu<br>         95                    100                 105 | 399 |
| gcc aac ccc tgc cgc aat ggg ggc acc tgt gac ctg ctc act ctc aca<br>Ala Asn Pro Cys Arg Asn Gly Gly Thr Cys Asp Leu Leu Thr Leu Thr<br>        110                    115                    120 | 447 |
| gag tac aag tgc cgc tgc tct cca ggg tgg tca gga aaa tca tgt cag<br>Glu Tyr Lys Cys Arg Cys Ser Pro Gly Trp Ser Gly Lys Ser Cys Gln<br>   125                    130                    135 | 495 |
| cag gct gac ccc tgt gcc tcc aac ccc tgt gcc aat ggt ggc cag tgc<br>Gln Ala Asp Pro Cys Ala Ser Asn Pro Cys Ala Asn Gly Gly Gln Cys<br>140                    145                   150                   155 | 543 |
| ctg ccc ttt gag tct tca tac atc tgt cgc tgc ccg cct ggc ttc cat<br>Leu Pro Phe Glu Ser Ser Tyr Ile Cys Arg Cys Pro Pro Gly Phe His<br>                  160                    165                    170 | 591 |
| ggc ccc acc tgc agg caa gat gtt aat gag tgc agc cag aac cct ggg<br>Gly Pro Thr Cys Arg Gln Asp Val Asn Glu Cys Ser Gln Asn Pro Gly<br>        175                    180                    185 | 639 |
| ctg tgc cgc cat gga ggc cac tgc cac aat gag atc ggc tcc tat cgc<br>Leu Cys Arg His Gly Gly His Cys His Asn Glu Ile Gly Ser Tyr Arg<br>   190                    195                    200 | 687 |
| tgt gcc tgc tgt gcc acc cat act ggt ccc cac tgt gaa ctg ccc tat<br>Cys Ala Cys Cys Ala Thr His Thr Gly Pro His Cys Glu Leu Pro Tyr<br>205                    210                   215 | 735 |
| gtg ccc tgc agc ccc tca ccc tgc cag aat gga gca acc tgc cgt cct<br>Val Pro Cys Ser Pro Ser Pro Cys Gln Asn Gly Ala Thr Cys Arg Pro<br>220                    225                   230                   235 | 783 |
| aca ggg gac acc acc cac gag tgt gcc tgc ttg cca ggt ttt gct gga<br>Thr Gly Asp Thr Thr His Glu Cys Ala Cys Leu Pro Gly Phe Ala Gly<br>        240                    245                    250 | 831 |
| cag aac tgt gaa gaa aat gtg gat gac tgt cca gga aac aac tgc aag<br>Gln Asn Cys Glu Glu Asn Val Asp Asp Cys Pro Gly Asn Asn Cys Lys<br>   255                    260                    265 | 879 |

-continued

| | | |
|---|---|---|
| aat ggg ggt gcc tgt gtg gac ggc gtg aat acc tac aat tgc cgc tgc<br>Asn Gly Gly Ala Cys Val Asp Gly Val Asn Thr Tyr Asn Cys Arg Cys<br>        270                  275                280 | 927 |
| cca ccg gag gtg acg ggt cag tac tgt aca gag gat gtg gac gaa tgt<br>Pro Pro Glu Val Thr Gly Gln Tyr Cys Thr Glu Asp Val Asp Glu Cys<br>285                  290                295 | 975 |
| cag ctc atg cca aat gcc tgc cag aat gcg gga acc tgc cac aac aca<br>Gln Leu Met Pro Asn Ala Cys Gln Asn Ala Gly Thr Cys His Asn Thr<br>300                  305                310                315 | 1023 |
| cac ggc ggc tac aac tgt gtg tgt gtc aat ggg tgg act ggc gag gac<br>His Gly Gly Tyr Asn Cys Val Cys Val Asn Gly Trp Thr Gly Glu Asp<br>        320                  325                330 | 1071 |
| tgc agt gag aac att gat gac tgt gcc agt gcc gcc tgt ttc cag ggt<br>Cys Ser Glu Asn Ile Asp Asp Cys Ala Ser Ala Ala Cys Phe Gln Gly<br>                335                340                345 | 1119 |
| gcc act tgc cac gac cgt gtg gct tcc ttc tac tgc gaa tgt ccg cat<br>Ala Thr Cys His Asp Arg Val Ala Ser Phe Tyr Cys Glu Cys Pro His<br>350                  355                360 | 1167 |
| ggg cgc aca ggt ctg ctg tgc cac ctc aag cat gcg tgc atc agc aac<br>Gly Arg Thr Gly Leu Leu Cys His Leu Lys His Ala Cys Ile Ser Asn<br>365                  370                375 | 1215 |
| ccc tgc aac gag ggc tcc aac tgt gac acc aac cct gtc aac ggc aaa<br>Pro Cys Asn Glu Gly Ser Asn Cys Asp Thr Asn Pro Val Asn Gly Lys<br>380                  385                390                395 | 1263 |
| cga atc tgc acc tgc ccc tcg ggg tac aca ggg cca gcc tgc agc cag<br>Arg Ile Cys Thr Cys Pro Ser Gly Tyr Thr Gly Pro Ala Cys Ser Gln<br>                  400                405                410 | 1311 |
| gac gtg gat gag tgt gat ctg ggt gcc aac cgt tgt gag cac gca ggc<br>Asp Val Asp Glu Cys Asp Leu Gly Ala Asn Arg Cys Glu His Ala Gly<br>                415                420                425 | 1359 |
| aaa tgc ctc aac aca ctg ggt tct ttt gag tgc cag tgt cta cag ggc<br>Lys Cys Leu Asn Thr Leu Gly Ser Phe Glu Cys Gln Cys Leu Gln Gly<br>430                  435                440 | 1407 |
| tac acg gga ccc ggc tgt gag att gat gtt aat gag tgc atc tcc aac<br>Tyr Thr Gly Pro Gly Cys Glu Ile Asp Val Asn Glu Cys Ile Ser Asn<br>445                  450                455 | 1455 |
| cca tgt cag aat gac gcc act tgc ctg gac cag att ggg gag ttc caa<br>Pro Cys Gln Asn Asp Ala Thr Cys Leu Asp Gln Ile Gly Glu Phe Gln<br>460                  465                470                475 | 1503 |
| tgc ata tgt atg cca ggt tat gaa ggt gta tac tgt gaa atc aac acg<br>Cys Ile Cys Met Pro Gly Tyr Glu Gly Val Tyr Cys Glu Ile Asn Thr<br>                  480                485                490 | 1551 |
| gat gag tgc gcc agc agc ccc tgt ctg cac aat ggc cac tgc atg gac<br>Asp Glu Cys Ala Ser Ser Pro Cys Leu His Asn Gly His Cys Met Asp<br>                    495                500                505 | 1599 |
| aag atc cat gag ttc caa tgt cag tgc ccc aaa ggc ttc aac ggg cac<br>Lys Ile His Glu Phe Gln Cys Gln Cys Pro Lys Gly Phe Asn Gly His<br>                510                515                520 | 1647 |
| ctg tgc cag tat gat gtg gat gag tgt gcc agc aca cca tgc aag aac<br>Leu Cys Gln Tyr Asp Val Asp Glu Cys Ala Ser Thr Pro Cys Lys Asn<br>525                  530                535 | 1695 |
| ggt gcc aag tgc ctg gat ggg ccc aac acc tat acc tgc gtg tgt aca<br>Gly Ala Lys Cys Leu Asp Gly Pro Asn Thr Tyr Thr Cys Val Cys Thr<br>540                  545                550                555 | 1743 |
| gaa ggt tac aca ggg acc cac tgc gaa gtg gac att gac gag tgt gac<br>Glu Gly Tyr Thr Gly Thr His Cys Glu Val Asp Ile Asp Glu Cys Asp<br>                    560                565                570 | 1791 |
| cct gac ccc tgc cac tat ggt tcc tgt aag gat ggt gtg gcc acc ttt<br>Pro Asp Pro Cys His Tyr Gly Ser Cys Lys Asp Gly Val Ala Thr Phe<br>                575                580                585 | 1839 |

```
acc tgc ctg tgc cag cca ggc tac aca ggc cat cac tgt gag acc aac       1887
Thr Cys Leu Cys Gln Pro Gly Tyr Thr Gly His His Cys Glu Thr Asn
        590                 595                 600 atc aat gag tgc cac agc caa ccg tgc cgc cat ggg ggc acc tgc cag       1935
Ile Asn Glu Cys His Ser Gln Pro Cys Arg His Gly Gly Thr Cys Gln
605                 610                 615 gac cgt gac aac tcc tac ctc tgc tta tgc ctc aag gga acc aca ggg       1983
Asp Arg Asp Asn Ser Tyr Leu Cys Leu Cys Leu Lys Gly Thr Thr Gly
620                 625                 630                 635 ccc aac tgt gag atc aac ctg gat gac tgc gcc agc aac ccc tgt gac       2031
Pro Asn Cys Glu Ile Asn Leu Asp Asp Cys Ala Ser Asn Pro Cys Asp
                640                 645                 650 tct ggc acc tgt ctg gac aag att gat ggc tac gaa tgt gcc tgt gaa       2079
Ser Gly Thr Cys Leu Asp Lys Ile Asp Gly Tyr Glu Cys Ala Cys Glu
        655                 660                 665 cca ggc tac aca gga agc atg tgt aac gtc aac att gac gaa tgt gcg       2127
Pro Gly Tyr Thr Gly Ser Met Cys Asn Val Asn Ile Asp Glu Cys Ala
            670                 675                 680 ggc agc ccc tgc cac aac ggg ggc act tgt gag gat ggc atc gcg ggc       2175
Gly Ser Pro Cys His Asn Gly Gly Thr Cys Glu Asp Gly Ile Ala Gly
685                 690                 695 ttc act tgc cgc tgc ccc gag ggc tac cat gac ccc acg tgc ctg tcc       2223
Phe Thr Cys Arg Cys Pro Glu Gly Tyr His Asp Pro Thr Cys Leu Ser
700                 705                 710                 715 gag gtc aac gag tgc aac agt aac ccc tgc atc cac gga gct tgc cgg       2271
Glu Val Asn Glu Cys Asn Ser Asn Pro Cys Ile His Gly Ala Cys Arg
                720                 725                 730 gat ggc ctc aat ggg tac aag tgt gac tgt gcc cct ggg tgg agt gga       2319
Asp Gly Leu Asn Gly Tyr Lys Cys Asp Cys Ala Pro Gly Trp Ser Gly
        735                 740                 745 aca aac tgt gac atc aac aac aac gag tgt gag tcc aac cct tgt gtc       2367
Thr Asn Cys Asp Ile Asn Asn Asn Glu Cys Glu Ser Asn Pro Cys Val
            750                 755                 760 aac ggt ggc acc tgc aag gac atg acc agt ggc tac gta tgc acc tgc       2415
Asn Gly Gly Thr Cys Lys Asp Met Thr Ser Gly Tyr Val Cys Thr Cys
765                 770                 775 cga gaa ggc ttc agt ggc cct aat tgc cag acc aac atc aac gaa tgt       2463
Arg Glu Gly Phe Ser Gly Pro Asn Cys Gln Thr Asn Ile Asn Glu Cys
780                 785                 790                 795 gcc tcc aac ccc tgc ctg aac cag ggg acc tgc att gat gat gtc gct       2511
Ala Ser Asn Pro Cys Leu Asn Gln Gly Thr Cys Ile Asp Asp Val Ala
                800                 805                 810 gga tac aag tgc aac tgt cct ctg cca tat aca gga gcc acg tgt gag       2559
Gly Tyr Lys Cys Asn Cys Pro Leu Pro Tyr Thr Gly Ala Thr Cys Glu
        815                 820                 825 gtg gtg ttg gcc cca tgt gct acc agc ccc tgc aaa aac agc ggc gta       2607
Val Val Leu Ala Pro Cys Ala Thr Ser Pro Cys Lys Asn Ser Gly Val
            830                 835                 840 tgc aag gag tct gaa gac tat gag agt ttc tcc tgt gtc tgt ccc aca       2655
Cys Lys Glu Ser Glu Asp Tyr Glu Ser Phe Ser Cys Val Cys Pro Thr
845                 850                 855 ggc tgg caa ggt caa acc tgc gag gtt gac atc aat gag tgt gtg aaa       2703
Gly Trp Gln Gly Gln Thr Cys Glu Val Asp Ile Asn Glu Cys Val Lys
860                 865                 870                 875 agc cca tgt cgc cat ggg gcc tcc tgc cag aac acc aat ggc agc tac       2751
Ser Pro Cys Arg His Gly Ala Ser Cys Gln Asn Thr Asn Gly Ser Tyr
                880                 885                 890 cgc tgc ctc tgc cag gcc ggc tat aca ggt cgc aac tgt gag agt gac       2799
Arg Cys Leu Cys Gln Ala Gly Tyr Thr Gly Arg Asn Cys Glu Ser Asp
        895                 900                 905
```

-continued

| | | |
|---|---|---|
| atc gat gac tgc cgc ccc aac ccg tgt cac aat ggg ggt tcc tgc acc<br>Ile Asp Asp Cys Arg Pro Asn Pro Cys His Asn Gly Gly Ser Cys Thr<br>910                     915                     920 | 2847 |
| gat ggc atc aac aca gcc ttc tgc gac tgc ctg ccc ggc ttc cag ggt<br>Asp Gly Ile Asn Thr Ala Phe Cys Asp Cys Leu Pro Gly Phe Gln Gly<br>925                     930                     935 | 2895 |
| gcc ttc tgt gag gag gac atc aat gaa tgt gcc agc aat ccc tgc caa<br>Ala Phe Cys Glu Glu Asp Ile Asn Glu Cys Ala Ser Asn Pro Cys Gln<br>940                     945                     950                     955 | 2943 |
| aat gga gcc aat tgc act gac tgt gtg gac agc tac aca tgt acc tgc<br>Asn Gly Ala Asn Cys Thr Asp Cys Val Asp Ser Tyr Thr Cys Thr Cys<br>960                     965                     970 | 2991 |
| ccc gtg ggc ttc aat ggc atc cac tgc gag aac aac aca cct gac tgt<br>Pro Val Gly Phe Asn Gly Ile His Cys Glu Asn Asn Thr Pro Asp Cys<br>975                     980                     985 | 3039 |
| act gag agc tcc tgc ttc aat ggt ggt acc tgt gtg gat ggt atc aac<br>Thr Glu Ser Ser Cys Phe Asn Gly Gly Thr Cys Val Asp Gly Ile Asn<br>990                     995                     1000 | 3087 |
| tcc ttc acc tgt ctg tgt cca cct ggc ttc acg ggc agc tac tgt<br>Ser Phe Thr Cys Leu Cys Pro Pro Gly Phe Thr Gly Ser Tyr Cys<br>1005                    1010                  1015 | 3132 |
| cag tat gat gtc aat gag tgt gat tca cgg ccc tgt ctg cac ggt<br>Gln Tyr Asp Val Asn Glu Cys Asp Ser Arg Pro Cys Leu His Gly<br>1020                  1025                  1030 | 3177 |
| ggt acc tgc caa gac agc tat ggt act tat aag tgt acc tgc cca<br>Gly Thr Cys Gln Asp Ser Tyr Gly Thr Tyr Lys Cys Thr Cys Pro<br>1035                  1040                  1045 | 3222 |
| cag ggc tac act ggt ctc aac tgc cag aac ctt gtg cgc tgg tgc<br>Gln Gly Tyr Thr Gly Leu Asn Cys Gln Asn Leu Val Arg Trp Cys<br>1050                  1055                  1060 | 3267 |
| gac tcg gct ccc tgc aag aat ggt ggc agg tgc tgg cag acc aac<br>Asp Ser Ala Pro Cys Lys Asn Gly Gly Arg Cys Trp Gln Thr Asn<br>1065                  1070                  1075 | 3312 |
| acg cag tac cac tgt gag tgc cgc agc ggc tgg act ggc gtc aac<br>Thr Gln Tyr His Cys Glu Cys Arg Ser Gly Trp Thr Gly Val Asn<br>1080                  1085                  1090 | 3357 |
| tgc gac gtg ctc agt gtg tcc tgt gag gtg gct gca cag aag cga<br>Cys Asp Val Leu Ser Val Ser Cys Glu Val Ala Ala Gln Lys Arg<br>1095                  1100                  1105 | 3402 |
| ggc att gac gtc act ctc ctg tgc cag cat gga ggg ctc tgt gtg<br>Gly Ile Asp Val Thr Leu Leu Cys Gln His Gly Gly Leu Cys Val<br>1110                  1115                  1120 | 3447 |
| gat gag gga gat aaa cat tac tgc cac tgc cag gca ggc tac acg<br>Asp Glu Gly Asp Lys His Tyr Cys His Cys Gln Ala Gly Tyr Thr<br>1125                  1130                  1135 | 3492 |
| ggc agc tac tgt gag gac gag gtg gac gag tgc tca cct aac ccc<br>Gly Ser Tyr Cys Glu Asp Glu Val Asp Glu Cys Ser Pro Asn Pro<br>1140                  1145                  1150 | 3537 |
| tgc cag aat gga gct acc tgc act gac tat ctc ggc ggc ttt tcc<br>Cys Gln Asn Gly Ala Thr Cys Thr Asp Tyr Leu Gly Gly Phe Ser<br>1155                  1160                  1165 | 3582 |
| tgc aag tgt gtg gct ggc tac cat ggg tct aac tgc tcc gag gag<br>Cys Lys Cys Val Ala Gly Tyr His Gly Ser Asn Cys Ser Glu Glu<br>1170                  1175                  1180 | 3627 |
| atc aac gag tgc ctg tcc cag ccc tgc cag aat ggg ggt acc tgc<br>Ile Asn Glu Cys Leu Ser Gln Pro Cys Gln Asn Gly Gly Thr Cys<br>1185                  1190                  1195 | 3672 |
| att gat ctg acc aac tcc tac aag tgt tcc tgc ccc cgg ggg aca<br>Ile Asp Leu Thr Asn Ser Tyr Lys Cys Ser Cys Pro Arg Gly Thr<br>1200                  1205                  1210 | 3717 |

```
cag ggt gta cac tgt gag atc aat gtt gat gac tgc cat ccc ccc   3762
Gln Gly Val His Cys Glu Ile Asn Val Asp Asp Cys His Pro Pro
    1215            1220                1225 ctt gac cct gcc tcc cga agc ccc aag tgc ttc aac aat ggc acc   3807
Leu Asp Pro Ala Ser Arg Ser Pro Lys Cys Phe Asn Asn Gly Thr
        1230                1235                1240 tgt gtg gac cag gtg ggt ggc tat acc tgc acc tgc cca cca ggc   3852
Cys Val Asp Gln Val Gly Gly Tyr Thr Cys Thr Cys Pro Pro Gly
            1245                1250                1255 ttc gtc ggg gag cgg tgt gag ggt gat gtc aat gaa tgt ctc tcc   3897
Phe Val Gly Glu Arg Cys Glu Gly Asp Val Asn Glu Cys Leu Ser
                1260                1265                1270 aac ccc tgt gac cca cgt ggc acc cag aac tgt gtg cag cgt gtt   3942
Asn Pro Cys Asp Pro Arg Gly Thr Gln Asn Cys Val Gln Arg Val
    1275                1280                1285 aat gac ttc cac tgc gag tgc cgg gct ggc cac act gga cgc cgc   3987
Asn Asp Phe His Cys Glu Cys Arg Ala Gly His Thr Gly Arg Arg
        1290                1295                1300 tgt gag tca gtc atc aat ggc tgc agg ggc aaa cct tgc aag aat   4032
Cys Glu Ser Val Ile Asn Gly Cys Arg Gly Lys Pro Cys Lys Asn
            1305                1310                1315 ggg ggt gtc tgt gcc gtg gcc tcc aac acc gcc cgt gga ttc atc   4077
Gly Gly Val Cys Ala Val Ala Ser Asn Thr Ala Arg Gly Phe Ile
                1320                1325                1330 tgt agg tgc cct gcg ggc ttc gag ggt gcc aca tgt gag aat gat   4122
Cys Arg Cys Pro Ala Gly Phe Glu Gly Ala Thr Cys Glu Asn Asp
    1335                1340                1345 gcc cgc act tgt ggc agc tta cgc tgt ctc aac ggt ggt aca tgc   4167
Ala Arg Thr Cys Gly Ser Leu Arg Cys Leu Asn Gly Gly Thr Cys
        1350                1355                1360 atc tcg ggc cca cgt agt ccc acc tgc cta tgc ctg gga tcc ttc   4212
Ile Ser Gly Pro Arg Ser Pro Thr Cys Leu Cys Leu Gly Ser Phe
            1365                1370                1375 acc ggc cct gag tgc cag ttc cca gcc agc agc ccc tgt gtg ggt   4257
Thr Gly Pro Glu Cys Gln Phe Pro Ala Ser Ser Pro Cys Val Gly
                1380                1385                1390 agc aac ccc tgc tac aat cag ggc acc tgt gag ccc aca tcc gag   4302
Ser Asn Pro Cys Tyr Asn Gln Gly Thr Cys Glu Pro Thr Ser Glu
    1395                1400                1405 aac cct ttc tac cgc tgt cta tgc cct gcc aaa ttc aac ggg cta   4347
Asn Pro Phe Tyr Arg Cys Leu Cys Pro Ala Lys Phe Asn Gly Leu
        1410                1415                1420 ctg tgc cac atc ctg gac tac agc ttc aca ggt ggc gct ggc ccg   4392
Leu Cys His Ile Leu Asp Tyr Ser Phe Thr Gly Gly Ala Gly Pro
            1425                1430                1435 gac att ccc cca ccg cag att gag gag gcc tgt gag ctg cct gag   4437
Asp Ile Pro Pro Pro Gln Ile Glu Glu Ala Cys Glu Leu Pro Glu
                1440                1445                1450 tgc cag gtg gat gca ggc aat aag gtc tgc aac ctg cag tgt aat   4482
Cys Gln Val Asp Ala Gly Asn Lys Val Cys Asn Leu Gln Cys Asn
    1455                1460                1465 aat cac gca tgt ggc tgg gat ggt ggc gac tgc tcc ctc aac ttc   4527
Asn His Ala Cys Gly Trp Asp Gly Gly Asp Cys Ser Leu Asn Phe
        1470                1475                1480 aat gac ccc tgg aag aac tgc acg cag tct cta cag tgc tgg aag   4572
Asn Asp Pro Trp Lys Asn Cys Thr Gln Ser Leu Gln Cys Trp Lys
            1485                1490                1495 tat ttt agc gac ggc cac tgt gac agc cag tgc aac tcg gcc ggc   4617
Tyr Phe Ser Asp Gly His Cys Asp Ser Gln Cys Asn Ser Ala Gly
                1500                1505                1510
```

-continued

| | |
|---|---|
| tgc ctc ttt gat ggc ttc gac tgc cag ctc acc gag gga cag tgc<br>Cys Leu Phe Asp Gly Phe Asp Cys Gln Leu Thr Glu Gly Gln Cys<br>1515                        1520                        1525 | 4662 |
| aac ccc ctg tat gac cag tac tgc aag gac cac ttc agt gat ggc<br>Asn Pro Leu Tyr Asp Gln Tyr Cys Lys Asp His Phe Ser Asp Gly<br>1530                        1535                        1540 | 4707 |
| cac tgc gac cag ggc tgt aac agt gcc gaa tgt gag tgg gat ggc<br>His Cys Asp Gln Gly Cys Asn Ser Ala Glu Cys Glu Trp Asp Gly<br>1545                        1550                        1555 | 4752 |
| cta gac tgt gct gag cat gta ccc gag cgg ctg gca gcg ggc acc<br>Leu Asp Cys Ala Glu His Val Pro Glu Arg Leu Ala Ala Gly Thr<br>1560                        1565                        1570 | 4797 |
| ctg gtc ctg gtg gtg ctg ctt cca ccc gac cag cta cgg aac aac<br>Leu Val Leu Val Val Leu Leu Pro Pro Asp Gln Leu Arg Asn Asn<br>1575                        1580                        1585 | 4842 |
| tcc ttc cac ttt ctg cgg gag ctc agc cac gtg ctg cac acc aac<br>Ser Phe His Phe Leu Arg Glu Leu Ser His Val Leu His Thr Asn<br>1590                        1595                        1600 | 4887 |
| gtg gtc ttc aag cgt gat gcg caa ggc cag cag atg atc ttc ccg<br>Val Val Phe Lys Arg Asp Ala Gln Gly Gln Gln Met Ile Phe Pro<br>1605                        1610                        1615 | 4932 |
| tac tat ggc cac gag gaa gag ctg cgc aag cac cca atc aag cgc<br>Tyr Tyr Gly His Glu Glu Glu Leu Arg Lys His Pro Ile Lys Arg<br>1620                        1625                        1630 | 4977 |
| tct aca gtg ggt tgg gcc acc tct tca ctg ctt cct ggt acc agt<br>Ser Thr Val Gly Trp Ala Thr Ser Ser Leu Leu Pro Gly Thr Ser<br>1635                        1640                        1645 | 5022 |
| ggt ggg cgc cag cgc agg gag ctg gac ccc atg gac atc cgt ggc<br>Gly Gly Arg Gln Arg Arg Glu Leu Asp Pro Met Asp Ile Arg Gly<br>1650                        1655                        1660 | 5067 |
| tcc att gtc tac ctg gag atc gac aac cgg caa tgt gtg cag tca<br>Ser Ile Val Tyr Leu Glu Ile Asp Asn Arg Gln Cys Val Gln Ser<br>1665                        1670                        1675 | 5112 |
| tcc tcg cag tgc ttc cag agt gcc acc gat gtg gct gcc ttc cta<br>Ser Ser Gln Cys Phe Gln Ser Ala Thr Asp Val Ala Ala Phe Leu<br>1680                        1685                        1690 | 5157 |
| ggt gct ctt gcg tca ctt ggc agc ctc aat att cct tac aag att<br>Gly Ala Leu Ala Ser Leu Gly Ser Leu Asn Ile Pro Tyr Lys Ile<br>1695                        1700                        1705 | 5202 |
| gag gcc gtg aag agt gag ccg gtg gag cct ccg ctg ccc tcg cag<br>Glu Ala Val Lys Ser Glu Pro Val Glu Pro Pro Leu Pro Ser Gln<br>1710                        1715                        1720 | 5247 |
| ctg cac ctc atg tac gtg gca gcg gcc gcc ttc gtg ctc ctg ttc<br>Leu His Leu Met Tyr Val Ala Ala Ala Ala Phe Val Leu Leu Phe<br>1725                        1730                        1735 | 5292 |
| ttt gtg ggc tgt ggg gtg ctg ctg tcc cgc aag cgc cgg cgc cag<br>Phe Val Gly Cys Gly Val Leu Leu Ser Arg Lys Arg Arg Arg Gln<br>1740                        1745                        1750 | 5337 |
| cat ggc cag ctc tgg ttc cct gag ggt ttc aaa gtg tca gag gcc<br>His Gly Gln Leu Trp Phe Pro Glu Gly Phe Lys Val Ser Glu Ala<br>1755                        1760                        1765 | 5382 |
| agc aag aag aag cgg aga gag ccc ctc ggc gag gac tca gtc ggc<br>Ser Lys Lys Lys Arg Arg Glu Pro Leu Gly Glu Asp Ser Val Gly<br>1770                        1775                        1780 | 5427 |
| ctc aag ccc ctg aag aat gcc tca gat ggt gct ctg atg gac gac<br>Leu Lys Pro Leu Lys Asn Ala Ser Asp Gly Ala Leu Met Asp Asp<br>1785                        1790                        1795 | 5472 |
| aat cag aac gag tgg gga gac gaa gac ctg gag acc aag aag ttc<br>Asn Gln Asn Glu Trp Gly Asp Glu Asp Leu Glu Thr Lys Lys Phe<br>1800                        1805                        1810 | 5517 |

| | | |
|---|---|---|
| cgg ttt gag gag cca gta gtt ctc cct gac ctg agt gat cag act<br>Arg Phe Glu Glu Pro Val Val Leu Pro Asp Leu Ser Asp Gln Thr<br>1815                              1820                         1825 | 5562 |
| gac cac agg cag tgg acc cag cag cac ctg gac gct gct gac ctg<br>Asp His Arg Gln Trp Thr Gln Gln His Leu Asp Ala Ala Asp Leu<br>1830                             1835                        1840 | 5607 |
| cgc atg tct gcc atg gcc cca aca ccg cct cag ggg gag gtg gat<br>Arg Met Ser Ala Met Ala Pro Thr Pro Pro Gln Gly Glu Val Asp<br>1845                            1850                     1855 | 5652 |
| gct gac tgc atg gat gtc aat gtt cga gga cca gat ggc ttc aca<br>Ala Asp Cys Met Asp Val Asn Val Arg Gly Pro Asp Gly Phe Thr<br>1860                          1865                     1870 | 5697 |
| ccc ctc atg att gcc tcc tgc agt gga ggg ggc ctt gag aca ggc<br>Pro Leu Met Ile Ala Ser Cys Ser Gly Gly Gly Leu Glu Thr Gly<br>1875                          1880                    1885 | 5742 |
| aac agt gaa gaa gaa gaa gat gca cct gct gtc atc tct gac ttc<br>Asn Ser Glu Glu Glu Glu Asp Ala Pro Ala Val Ile Ser Asp Phe<br>1890                         1895                    1900 | 5787 |
| atc tac cag ggc gcc agc ttg cac aac cag aca gac cgc acc ggg<br>Ile Tyr Gln Gly Ala Ser Leu His Asn Gln Thr Asp Arg Thr Gly<br>1905                          1910                    1915 | 5832 |
| gag acc gcc ttg cac ttg gct gcc cga tac tct cgt tca gat cgt<br>Glu Thr Ala Leu His Leu Ala Ala Arg Tyr Ser Arg Ser Asp Arg<br>1920                          1925                    1930 | 5877 |
| cga aag cgc ctt gag gcc agt gca gat gcc aac atc cag gac aac<br>Arg Lys Arg Leu Glu Ala Ser Ala Asp Ala Asn Ile Gln Asp Asn<br>1935                          1940                    1945 | 5922 |
| atg ggc cgt act ccg tta cat gca gca gtt tct gca gat gct cag<br>Met Gly Arg Thr Pro Leu His Ala Ala Val Ser Ala Asp Ala Gln<br>1950                          1955                    1960 | 5967 |
| ggt gtc ttc cag atc ctg ctc cgg aac agg gcc aca gat ctg gat<br>Gly Val Phe Gln Ile Leu Leu Arg Asn Arg Ala Thr Asp Leu Asp<br>1965                          1970                    1975 | 6012 |
| gcc cga atg cat gat ggc aca act cca ctg atc ctg gct gcg cgc<br>Ala Arg Met His Asp Gly Thr Thr Pro Leu Ile Leu Ala Ala Arg<br>1980                          1985                    1990 | 6057 |
| ctg gcc gtg gag ggc atg ctg gag gac ctc atc aac tca cat gct<br>Leu Ala Val Glu Gly Met Leu Glu Asp Leu Ile Asn Ser His Ala<br>1995                          2000                    2005 | 6102 |
| gac gtc aat gcc gtg gat gac cta ggc aag tcg gct ttg cat tgg<br>Asp Val Asn Ala Val Asp Asp Leu Gly Lys Ser Ala Leu His Trp<br>2010                          2015                    2020 | 6147 |
| gcg gcc gcg gtg aac aat gtg gat gct gct gtt gtg ctc ctg aag<br>Ala Ala Ala Val Asn Asn Val Asp Ala Ala Val Val Leu Leu Lys<br>2025                          2030                    2035 | 6192 |
| aac gga gcc aac aag gac atc gag aac aac aag gag gag act tcc<br>Asn Gly Ala Asn Lys Asp Ile Glu Asn Asn Lys Glu Glu Thr Ser<br>2040                          2045                    2050 | 6237 |
| ctg ttc ctg tcg atc cgc cgt gag agc tat gag act gcc aaa gtg<br>Leu Phe Leu Ser Ile Arg Arg Glu Ser Tyr Glu Thr Ala Lys Val<br>2055                          2060                    2065 | 6282 |
| ttg ctg gac cac ttt gcc aac cgg gac atc acg gat cac atg gac<br>Leu Leu Asp His Phe Ala Asn Arg Asp Ile Thr Asp His Met Asp<br>2070                          2075                    2080 | 6327 |
| cga ttg ccg cgg gac atc gca cag gag cgt atg cac cac gat atc<br>Arg Leu Pro Arg Asp Ile Ala Gln Glu Arg Met His His Asp Ile<br>2085                          2090                    2095 | 6372 |
| gtg cgg ctt ttg gat gag tac aac ctg gtg cgg tcc cca cag ctg<br>Val Arg Leu Leu Asp Glu Tyr Asn Leu Val Arg Ser Pro Gln Leu<br>2100                          2105                    2110 | 6417 |

```
cat ggc act gcc ctg ggt ggc aca ccc act ctg tct ccc aca ctc      6462
His Gly Thr Ala Leu Gly Gly Thr Pro Thr Leu Ser Pro Thr Leu
    2115                2120                2125 tgc tcg cca aat ggc tac cct ggc aat ctc aag tct gcc aca cag      6507
Cys Ser Pro Asn Gly Tyr Pro Gly Asn Leu Lys Ser Ala Thr Gln
2130                2135                2140 ggc aag aag gcc cgc aag cca agc acc aaa ggg ctg gct tgt ggt      6552
Gly Lys Lys Ala Arg Lys Pro Ser Thr Lys Gly Leu Ala Cys Gly
    2145                2150                2155 agc aag gaa gct aag gac ctc aag gca cgg agg aag agt tcc cag      6597
Ser Lys Glu Ala Lys Asp Leu Lys Ala Arg Arg Lys Ser Ser Gln
2160                2165                2170 gat ggc aag ggc tgg ctg ttg gac agc tcg tcg agc atg ctg tcg      6642
Asp Gly Lys Gly Trp Leu Leu Asp Ser Ser Ser Ser Met Leu Ser
    2175                2180                2185 cct gtg gac tcc ctc gag tca ccc cat ggc tac ttg tca gat gtg      6687
Pro Val Asp Ser Leu Glu Ser Pro His Gly Tyr Leu Ser Asp Val
2190                2195                2200 gcc tcg cac ccc ctc ctc ccc tcc cca ttc cag cag tct cca tcc      6732
Ala Ser His Pro Leu Leu Pro Ser Pro Phe Gln Gln Ser Pro Ser
    2205                2210                2215 atg cct ctc agc cac ctg cct ggt atg cct gac acc cac ctg ggc      6777
Met Pro Leu Ser His Leu Pro Gly Met Pro Asp Thr His Leu Gly
2220                2225                2230 atc agc cac ttg aat gtg gca gcc aag cct gag atg gca gca ctg      6822
Ile Ser His Leu Asn Val Ala Ala Lys Pro Glu Met Ala Ala Leu
    2235                2240                2245 gct gga ggt agc cgg ttg gcc ttt gag cac ccc ccg cca cgc ctc      6867
Ala Gly Gly Ser Arg Leu Ala Phe Glu His Pro Pro Pro Arg Leu
2250                2255                2260 tcc cac ctg cct gta gcc tcc agt gcc tgc aca gtg ctg agt acc      6912
Ser His Leu Pro Val Ala Ser Ser Ala Cys Thr Val Leu Ser Thr
    2265                2270                2275 aat ggc acc ggg gct atg aat ttc acc gtg ggt gca ccg gca agc      6957
Asn Gly Thr Gly Ala Met Asn Phe Thr Val Gly Ala Pro Ala Ser
2280                2285                2290 ttg aat ggc cag tgt gag tgg ctt ccc cgg ctc cag aat ggc atg      7002
Leu Asn Gly Gln Cys Glu Trp Leu Pro Arg Leu Gln Asn Gly Met
    2295                2300                2305 gtg ccc agc cag tac aac cca cta cgg ccg ggt gtg acg ccg ggc      7047
Val Pro Ser Gln Tyr Asn Pro Leu Arg Pro Gly Val Thr Pro Gly
2310                2315                2320 aca ctg agc aca cag gca gct ggg ctc cag cat agc atg atg ggg      7092
Thr Leu Ser Thr Gln Ala Ala Gly Leu Gln His Ser Met Met Gly
    2325                2330                2335 cca cta cac agc agc ctc tcc acc aat acc ttg tcc ccg att att      7137
Pro Leu His Ser Ser Leu Ser Thr Asn Thr Leu Ser Pro Ile Ile
2340                2345                2350 tac cag ggc ctg ccc aac aca cgg ctg gca aca cag cct cac ctg      7182
Tyr Gln Gly Leu Pro Asn Thr Arg Leu Ala Thr Gln Pro His Leu
    2355                2360                2365 gtg cag acc cag cag gtg cag cca cag aac tta cca ctc cag cca      7227
Val Gln Thr Gln Gln Val Gln Pro Gln Asn Leu Pro Leu Gln Pro
2370                2375                2380 cag aac tta cag cca cca tca cag cca cac ctc agt gtg agc tcg      7272
Gln Asn Leu Gln Pro Pro Ser Gln Pro His Leu Ser Val Ser Ser
    2385                2390                2395 gca gcc aat ggg cac ctg ggg cgg agc ttc ttg agt ggg gag ccc      7317
Ala Ala Asn Gly His Leu Gly Arg Ser Phe Leu Ser Gly Glu Pro
2400                2405                2410
```

-continued

| | | |
|---|---|---|
| agt cag gca gat gta caa ccg ctg ggc ccc agc agt ctg cct gtg<br>Ser Gln Ala Asp Val Gln Pro Leu Gly Pro Ser Ser Leu Pro Val<br>    2415                    2420                    2425 | 7362 | |
| cac acc att ctg ccc cag gaa agc cag gcc cta cca aca tca ctg<br>His Thr Ile Leu Pro Gln Glu Ser Gln Ala Leu Pro Thr Ser Leu<br>    2430                    2435                    2440 | 7407 | |
| cca tcc tcc atg gtc cca ccc atg acc act acc cag ttc ctg acc<br>Pro Ser Ser Met Val Pro Pro Met Thr Thr Thr Gln Phe Leu Thr<br>    2445                    2450                    2455 | 7452 | |
| cct cca tca cag cac agt tac tcc tcc tcc cct gtg gac aac acc<br>Pro Pro Ser Gln His Ser Tyr Ser Ser Ser Pro Val Asp Asn Thr<br>    2460                    2465                    2470 | 7497 | |
| ccc agc cac cag ctg cag gtg cca gag ccc act ttc ctc acc cca<br>Pro Ser His Gln Leu Gln Val Pro Glu Pro Thr Phe Leu Thr Pro<br>    2475                    2480                    2485 | 7542 | |
| tcc cct gag tcc cct gac cag tgg tcc agc tcc tcc ccg cat tcc<br>Ser Pro Glu Ser Pro Asp Gln Trp Ser Ser Ser Ser Pro His Ser<br>    2490                    2495                    2500 | 7587 | |
| aac atc tct gat tgg tcc gag ggc atc tcc agc ccg ccc acc acc<br>Asn Ile Ser Asp Trp Ser Glu Gly Ile Ser Ser Pro Pro Thr Thr<br>    2505                    2510                    2515 | 7632 | |
| atg ccg tcc cag atc acc cac att cca gag gca ttt aaa taaacagaga<br>Met Pro Ser Gln Ile Thr His Ile Pro Glu Ala Phe Lys<br>    2520                    2525                    2530 | 7681 | |
| tgtgggatgc aggacccccag cttccgttcc caagccctgt tggaagtcct ttccagtgct | 7741 | |
| tcaggatgct ggggcgacca aaggagcttt taaaaaatg tttttataca aaataagagg | 7801 | |
| acaagaattt cattttttt tttagtattt atttatgtac ttttatttc cacagaaaca | 7861 | |
| ctgcctttt atttatatgt attgttttct atggcactag gggaaaaaca tatctgttcc | 7921 | |
| aagaaaataa actagttctc agagccttga ttttcctggt cagggtgaag ttccctgtgt | 7981 | |
| gtctgtaaaa tatgaacaag gattcatgat ttgtaaatgc tgtttattta ttgattgctt | 8041 | |
| ctttccaaaa tcgaaaaaaa aaa | 8064 | |

<210> SEQ ID NO 4
<211> LENGTH: 3641
<212> TYPE: DNA
<213> ORGANISM: Homo sapiens
<220> FEATURE:
<221> NAME/KEY: CDS
<222> LOCATION: (195)..(2504)

<400> SEQUENCE: 4

| | | |
|---|---|---|
| gctgactcgc ctggctctga gccccgccgc cgcgctcggg ctccgtcagt ttcctcggca | 60 | |
| gcggtaggcg agagcacgcg gaggagcgtg cgcgggggcc ccgggagacg gcggcggtgg | 120 | |
| cggcgcgggc agagcaagga cgcggcggat cccactcgca cagcagcgca ctcggtgccc | 180 | |
| cgcgcagggt cgcg atg ctg ccc ggt ttg gca ctg ctc ctg ctg gcc gcc<br>                        Met Leu Pro Gly Leu Ala Leu Leu Leu Leu Ala Ala<br>                          1                  5                        10 | 230 | |
| tgg acg gct cgg gcg ctg gag gta ccc act gat ggt aat gct ggc ctg<br>Trp Thr Ala Arg Ala Leu Glu Val Pro Thr Asp Gly Asn Ala Gly Leu<br>            15                    20                    25 | 278 | |
| ctg gct gaa ccc cag att gcc atg ttc tgt ggc aga ctg aac atg cac<br>Leu Ala Glu Pro Gln Ile Ala Met Phe Cys Gly Arg Leu Asn Met His<br>    30                    35                    40 | 326 | |
| atg aat gtc cag aat ggg aag tgg gat tca gat cca tca ggg acc aaa<br>Met Asn Val Gln Asn Gly Lys Trp Asp Ser Asp Pro Ser Gly Thr Lys<br>45                    50                    55                    60 | 374 | |

| | | |
|---|---|---|
| acc tgc att gat acc aag gaa ggc atc ctg cag tat tgc caa gaa gtc<br>Thr Cys Ile Asp Thr Lys Glu Gly Ile Leu Gln Tyr Cys Gln Glu Val<br>65 70 75 | | 422 |
| tac cct gaa ctg cag atc acc aat gtg gta gaa gcc aac caa cca gtg<br>Tyr Pro Glu Leu Gln Ile Thr Asn Val Val Glu Ala Asn Gln Pro Val<br>80 85 90 | | 470 |
| acc atc cag aac tgg tgc aag cgg ggc cgc aag cag tgc aag acc cat<br>Thr Ile Gln Asn Trp Cys Lys Arg Gly Arg Lys Gln Cys Lys Thr His<br>95 100 105 | | 518 |
| ccc cac ttt gtg att ccc tac cgc tgc tta gtt ggt gag ttt gta agt<br>Pro His Phe Val Ile Pro Tyr Arg Cys Leu Val Gly Glu Phe Val Ser<br>110 115 120 | | 566 |
| gat gcc ctt ctc gtt cct gac aag tgc aaa ttc tta cac cag gag agg<br>Asp Ala Leu Leu Val Pro Asp Lys Cys Lys Phe Leu His Gln Glu Arg<br>125 130 135 140 | | 614 |
| atg gat gtt tgc gaa act cat ctt cac tgg cac acc gtc gcc aaa gag<br>Met Asp Val Cys Glu Thr His Leu His Trp His Thr Val Ala Lys Glu<br>145 150 155 | | 662 |
| aca tgc agt gag aag agt acc aac ttg cat gac tac ggc atg ttg ctg<br>Thr Cys Ser Glu Lys Ser Thr Asn Leu His Asp Tyr Gly Met Leu Leu<br>160 165 170 | | 710 |
| ccc tgc gga att gac aag ttc cga ggg gta gag ttt gtg tgt tgc cca<br>Pro Cys Gly Ile Asp Lys Phe Arg Gly Val Glu Phe Val Cys Cys Pro<br>175 180 185 | | 758 |
| ctg gct gaa gaa agt gac aat gtg gat tct gct gat gcg gag gag gat<br>Leu Ala Glu Glu Ser Asp Asn Val Asp Ser Ala Asp Ala Glu Glu Asp<br>190 195 200 | | 806 |
| gac tcg gat gtc tgg tgg ggc gga gca gac aca gac tat gca gat ggg<br>Asp Ser Asp Val Trp Trp Gly Gly Ala Asp Thr Asp Tyr Ala Asp Gly<br>205 210 215 220 | | 854 |
| agt gaa gac aaa gta gta gaa gta gca gag gag gaa gaa gtg gct gag<br>Ser Glu Asp Lys Val Val Glu Val Ala Glu Glu Glu Glu Val Ala Glu<br>225 230 235 | | 902 |
| gtg gaa gaa gaa gaa gcc gat gat gac gag gac gat gag gat ggt gat<br>Val Glu Glu Glu Glu Ala Asp Asp Asp Glu Asp Asp Glu Asp Gly Asp<br>240 245 250 | | 950 |
| gag gta gag gaa gag gct gag gaa ccc tac gaa gaa gcc aca gag aga<br>Glu Val Glu Glu Glu Ala Glu Glu Pro Tyr Glu Glu Ala Thr Glu Arg<br>255 260 265 | | 998 |
| acc acc agc att gcc acc acc acc acc acc aca gag tct gtg gaa<br>Thr Thr Ser Ile Ala Thr Thr Thr Thr Thr Thr Glu Ser Val Glu<br>270 275 280 | | 1046 |
| gag gtg gtt cga gag gtg tgc tct gaa caa gcc gag acg ggc cgt tgc<br>Glu Val Val Arg Glu Val Cys Ser Glu Gln Ala Glu Thr Gly Pro Cys<br>285 290 295 300 | | 1094 |
| cga gca atg atc tcc cgc tgg tac ttt gat gtg act gaa ggg aag tgt<br>Arg Ala Met Ile Ser Arg Trp Tyr Phe Asp Val Thr Glu Gly Lys Cys<br>305 310 315 | | 1142 |
| gcc cca ttc ttt tac ggc gga tgt ggc ggc aac cgg aac aac ttt gac<br>Ala Pro Phe Phe Tyr Gly Gly Cys Gly Gly Asn Arg Asn Asn Phe Asp<br>320 325 330 | | 1190 |
| aca gaa gag tac tgc atg gcc gtg tgt ggc agc gcc atg tcc caa agt<br>Thr Glu Glu Tyr Cys Met Ala Val Cys Gly Ser Ala Met Ser Gln Ser<br>335 340 345 | | 1238 |
| tta ctc aag act acc cag gaa cct ctt gcc cga gat cct gtt aaa ctt<br>Leu Leu Lys Thr Thr Gln Glu Pro Leu Ala Arg Asp Pro Val Lys Leu<br>350 355 360 | | 1286 |
| cct aca aca gca gcc agt acc cct gat gcc gtt gac aag tat ctc gag<br>Pro Thr Thr Ala Ala Ser Thr Pro Asp Ala Val Asp Lys Tyr Leu Glu<br>365 370 375 380 | | 1334 |

```
aca cct ggg gat gag aat gaa cat gcc cat ttc cag aaa gcc aaa gag    1382
Thr Pro Gly Asp Glu Asn Glu His Ala His Phe Gln Lys Ala Lys Glu
                385                 390                 395 agg ctt gag gcc aag cac cga gag aga atg tcc cag gtc atg aga gaa    1430
Arg Leu Glu Ala Lys His Arg Glu Arg Met Ser Gln Val Met Arg Glu
            400                 405                 410 tgg gaa gag gca gaa cgt caa gca aag aac ttg cct aaa gct gat aag    1478
Trp Glu Glu Ala Glu Arg Gln Ala Lys Asn Leu Pro Lys Ala Asp Lys
        415                 420                 425 aag gca gtt atc cag cat ttc cag gag aaa gtg gaa tct ttg gaa cag    1526
Lys Ala Val Ile Gln His Phe Gln Glu Lys Val Glu Ser Leu Glu Gln
    430                 435                 440 gaa gca gcc aac gag aga cag cag ctg gtg gag aca cac atg gcc aga    1574
Glu Ala Ala Asn Glu Arg Gln Gln Leu Val Glu Thr His Met Ala Arg
445                 450                 455                 460 gtg gaa gcc atg ctc aat gac cgc cgc cgc ctg gcc ctg gag aac tac    1622
Val Glu Ala Met Leu Asn Asp Arg Arg Arg Leu Ala Leu Glu Asn Tyr
                465                 470                 475 atc acc gct ctg cag gct gtt cct cct cgg cct cgt cac gtg ttc aat    1670
Ile Thr Ala Leu Gln Ala Val Pro Pro Arg Pro Arg His Val Phe Asn
            480                 485                 490 atg cta aag aag tat gtc cgc gca gaa cag aag gac aga cag cac acc    1718
Met Leu Lys Lys Tyr Val Arg Ala Glu Gln Lys Asp Arg Gln His Thr
        495                 500                 505 cta aag cat ttc gag cat gtg cgc atg gtg gat ccc aag aaa gcc gct    1766
Leu Lys His Phe Glu His Val Arg Met Val Asp Pro Lys Lys Ala Ala
    510                 515                 520 cag atc cgg tcc cag gtt atg aca cac ctc cgt gtg att tat gag cgc    1814
Gln Ile Arg Ser Gln Val Met Thr His Leu Arg Val Ile Tyr Glu Arg
525                 530                 535                 540 atg aat cag tct ctc tcc ctg ctc tac aac gtg cct gca gtg gcc gag    1862
Met Asn Gln Ser Leu Ser Leu Leu Tyr Asn Val Pro Ala Val Ala Glu
                545                 550                 555 gag att cag gat gaa gtt gat gag ctg ctt cag aaa gag caa aac tat    1910
Glu Ile Gln Asp Glu Val Asp Glu Leu Leu Gln Lys Glu Gln Asn Tyr
            560                 565                 570 tca gat gac gtc ttg gcc aac atg att agt gaa cca agg atc agt tac    1958
Ser Asp Asp Val Leu Ala Asn Met Ile Ser Glu Pro Arg Ile Ser Tyr
        575                 580                 585 gga aac gat gct ctc atg cca tct ttg acc gaa acg aaa acc acc gtg    2006
Gly Asn Asp Ala Leu Met Pro Ser Leu Thr Glu Thr Lys Thr Thr Val
    590                 595                 600 gag ctc ctt ccc gtg aat gga gag ttc agc ctg gac gat ctc cag ccg    2054
Glu Leu Leu Pro Val Asn Gly Glu Phe Ser Leu Asp Asp Leu Gln Pro
605                 610                 615                 620 tgg cat tct ttt ggg gct gac tct gtg cca gcc aac aca gaa aac gaa    2102
Trp His Ser Phe Gly Ala Asp Ser Val Pro Ala Asn Thr Glu Asn Glu
                625                 630                 635 gtt gag cct gtt gat gcc cgc cct gct gcc gac cga gga ctg acc act    2150
Val Glu Pro Val Asp Ala Arg Pro Ala Ala Asp Arg Gly Leu Thr Thr
            640                 645                 650 cga cca ggt tct ggg ttg aca aat atc aag acg gag gag atc tct gaa    2198
Arg Pro Gly Ser Gly Leu Thr Asn Ile Lys Thr Glu Glu Ile Ser Glu
        655                 660                 665 gtg aag atg gat gca gaa ttc cga cat gac tca gga tat gaa gtt cat    2246
Val Lys Met Asp Ala Glu Phe Arg His Asp Ser Gly Tyr Glu Val His
    670                 675                 680 cat caa aaa ttg gtg ttc ttt gca gaa gat gtg ggt tca aac aaa ggt    2294
His Gln Lys Leu Val Phe Phe Ala Glu Asp Val Gly Ser Asn Lys Gly
685                 690                 695                 700
```

```
gca atc att gga ctc atg gtg ggc ggt gtt gtc ata gcg aca gtg atc    2342
Ala Ile Ile Gly Leu Met Val Gly Gly Val Val Ile Ala Thr Val Ile
            705                 710                 715 gtc atc acc ttg gtg atg ctg aag aag aaa cag tac aca tcc att cat    2390
Val Ile Thr Leu Val Met Leu Lys Lys Lys Gln Tyr Thr Ser Ile His
            720                 725                 730 cat ggt gtg gtg gag gtt gac gcc gct gtc acc cca gag gag cgc cac    2438
His Gly Val Val Glu Val Asp Ala Ala Val Thr Pro Glu Glu Arg His
            735                 740                 745 ctg tcc aag atg cag cag aac ggc tac gaa aat cca acc tac aag ttc    2486
Leu Ser Lys Met Gln Gln Asn Gly Tyr Glu Asn Pro Thr Tyr Lys Phe
            750                 755                 760 ttt gag cag atg cag aac tagaccccg ccacagcagc ctctgaagtt             2534
Phe Glu Gln Met Gln Asn
765                 770 ggacagcaaa accattgctt cactacccat cggtgtccat ttatagaata atgtgggaag   2594
aaacaaaccc gttttatgat ttactcatta tcgccttttg acagctgtgc tgtaacacaa   2654
gtagatgcct gaacttgaat taatccacac atcagtaatg tattctatct ctctttacat   2714
tttggtctct atactacatt attaatgggt tttgtgtact gtaaagaatt tagctgtatc   2774
aaactagtgc atgaatagat tctctcctga ttatttatca catagcccct tagccagttg   2834
tatattattc ttgtggtttg tgacccaatt aagtcctact ttacatatgc tttaagaatc   2894 gatggggat gcttcatgtg aacgtgggag ttcagctgct tctcttgcct aagtattcct    2954
ttcctgatca ctatgcattt taaagttaaa cattttaag tatttcagat gctttagaga    3014 gattttttt ccatgactgc attttactgt acagattgct gcttctgcta tatttgtgat    3074
ataggaatta agaggataca cacgtttgtt tcttcgtgcc tgttttatgt gcacacatta   3134
ggcattgaga cttcaagctt ttctttttt gtccacgtat ctttgggtct ttgataaaga    3194
aaagaatccc tgttcattgt aagcactttt acggggcggg tggggagggg tgctctgctg   3254
gtcttcaatt accaagaatt ctccaaaaca attttctgca ggatgattgt acagaatcat   3314
tgcttatgac atgatcgctt tctacactgt attacataaa taaattaaat aaaataaccc   3374
cgggcaagac ttttctttga aggatgacta cagacattaa ataatcgaag taattttggg   3434
tggggagaag aggcagattc aattttcttt aaccagtctg aagtttcatt tatgatacaa   3494
aagaagatga aatgaagt ggcaatataa ggggatgagg aaggcatgcc tggacaaacc     3554
cttcttttaa gatgtgtctt caatttgtat aaaatggtgt tttcatgtaa ataaatacat   3614
tcttggagga gcaaaaaaaa aaaaaaa                                        3641

<210> SEQ ID NO 5
<211> LENGTH: 22
<212> TYPE: PRT
<213> ORGANISM: Mus musculus

<400> SEQUENCE: 5

His Leu Met Tyr Val Ala Ala Ala Phe Val Leu Leu Phe Phe Val
1               5                   10                  15

Gly Cys Gly Val Leu Leu
            20

<210> SEQ ID NO 6
<211> LENGTH: 66
<212> TYPE: DNA
<213> ORGANISM: Mus musculus
<220> FEATURE:
<221> NAME/KEY: CDS
<222> LOCATION: (1)..(66)
```

<400> SEQUENCE: 6

| cac | ctc | atg | tac | gtg | gca | gcg | gcc | gcc | ttc | gtg | ctc | ctg | ttc | ttt | gtg | 48 |
|---|---|---|---|---|---|---|---|---|---|---|---|---|---|---|---|---|
| His | Leu | Met | Tyr | Val | Ala | Ala | Ala | Ala | Phe | Val | Leu | Leu | Phe | Phe | Val | |
| 1 | | | | 5 | | | | | 10 | | | | | 15 | | |

| ggc | tgt | ggg | gtg | ctg | ctg | | | | | | | | | | | 66 |
|---|---|---|---|---|---|---|---|---|---|---|---|---|---|---|---|---|
| Gly | Cys | Gly | Val | Leu | Leu | | | | | | | | | | | |
| | | | 20 | | | | | | | | | | | | | |

<210> SEQ ID NO 7
<211> LENGTH: 24
<212> TYPE: PRT
<213> ORGANISM: Homo sapiens

<400> SEQUENCE: 7

Gly Ala Ile Ile Gly Leu Met Val Gly Gly Val Val Ile Ala Thr Val
1               5                   10                  15

Ile Val Ile Thr Leu Val Met Leu
            20

<210> SEQ ID NO 8
<211> LENGTH: 72
<212> TYPE: DNA
<213> ORGANISM: Homo sapiens
<220> FEATURE:
<221> NAME/KEY: CDS
<222> LOCATION: (1)..(72)

<400> SEQUENCE: 8

| ggt | gca | atc | att | gga | ctc | atg | gtg | ggc | ggt | gtt | gtc | ata | gcg | aca | gtg | 48 |
|---|---|---|---|---|---|---|---|---|---|---|---|---|---|---|---|---|
| Gly | Ala | Ile | Ile | Gly | Leu | Met | Val | Gly | Gly | Val | Val | Ile | Ala | Thr | Val | |
| 1 | | | | 5 | | | | | 10 | | | | | 15 | | |

| atc | gtc | atc | acc | ttg | gtg | atg | ctg | | | | | | | | | 72 |
|---|---|---|---|---|---|---|---|---|---|---|---|---|---|---|---|---|
| Ile | Val | Ile | Thr | Leu | Val | Met | Leu | | | | | | | | | |
| | | | 20 | | | | | | | | | | | | | |

<210> SEQ ID NO 9
<211> LENGTH: 99
<212> TYPE: PRT
<213> ORGANISM: Mus musculus

<400> SEQUENCE: 9

Val Lys Ser Glu Pro Val Glu Pro Pro Leu Pro Ser Gln Leu His Leu
1               5                   10                  15

Val Tyr Val Ala Ala Ala Ala Phe Val Leu Leu Phe Phe Val Gly Cys
                20                  25                  30

Gly Val Leu Leu Ser Arg Lys Arg Arg Arg Gln His Gly Gln Leu Trp
            35                  40                  45

Phe Pro Glu Gly Phe Lys Val Ser Glu Ala Ser Lys Lys Lys Arg Arg
        50                  55                  60

Glu Pro Leu Gly Glu Asp Ser Val Gly Leu Lys Pro Leu Lys Asn Ala
65                  70                  75                  80

Ser Asp Gly Ala Leu Met Asp Asp Asn Gln Asn Glu Trp Gly Asp Glu
                85                  90                  95

Asp Leu Glu

<210> SEQ ID NO 10
<211> LENGTH: 297
<212> TYPE: DNA
<213> ORGANISM: Mus musculus
<220> FEATURE:
<221> NAME/KEY: CDS
<222> LOCATION: (1)..(297)

<400> SEQUENCE: 10

| | | | | | | | | | | | | | | | | |
|---|---|---|---|---|---|---|---|---|---|---|---|---|---|---|---|---|
| gtg | aag | agt | gag | ccg | gtg | gag | cct | ccg | ctg | ccc | tcg | cag | ctg | cac | ctc | 48 |
| Val | Lys | Ser | Glu | Pro | Val | Glu | Pro | Pro | Leu | Pro | Ser | Gln | Leu | His | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | tac | gtg | gca | gcg | gcc | gcc | ttc | gtg | ctg | ttc | ttt | gtg | ggc | tgt | | 96 |
| Val | Tyr | Val | Ala | Ala | Ala | Ala | Phe | Val | Leu | Phe | Phe | Val | Gly | Cys | | |
| | | | 20 | | | | | 25 | | | | | 30 | | | |

| | | | | | | | | | | | | | | | | |
|---|---|---|---|---|---|---|---|---|---|---|---|---|---|---|---|---|
| ggg | gtg | ctg | ctg | tcc | cgc | aag | cgc | cgg | cag | cat | ggc | cag | ctc | tgg | | 144 |
| Gly | Val | Leu | Leu | Ser | Arg | Lys | Arg | Arg | Gln | His | Gly | Gln | Leu | Trp | | |
| | | 35 | | | | | 40 | | | | | 45 | | | | |

| | | | | | | | | | | | | | | | | |
|---|---|---|---|---|---|---|---|---|---|---|---|---|---|---|---|---|
| ttc | cct | gag | ggt | ttc | aaa | gtg | tca | gag | gcc | agc | aag | aag | aag | cgg | aga | 192 |
| Phe | Pro | Glu | Gly | Phe | Lys | Val | Ser | Glu | Ala | Ser | Lys | Lys | Lys | Arg | Arg | |
| 50 | | | | | 55 | | | | | 60 | | | | | | |

| | | | | | | | | | | | | | | | | |
|---|---|---|---|---|---|---|---|---|---|---|---|---|---|---|---|---|
| gag | ccc | ctc | ggc | gag | gac | tca | gtc | ggc | ctc | aag | ccc | ctg | aag | aat | gcc | 240 |
| Glu | Pro | Leu | Gly | Glu | Asp | Ser | Val | Gly | Leu | Lys | Pro | Leu | Lys | Asn | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tca | gat | ggt | gct | ctg | atg | gac | gac | aat | cag | aac | gag | tgg | gga | gac | gaa | 288 |
| Ser | Asp | Gly | Ala | Leu | Met | Asp | Asp | Asn | Gln | Asn | Glu | Trp | Gly | Asp | Glu | |
| | | | | 85 | | | | | 90 | | | | | 95 | | |

| | | | |
|---|---|---|---|
| gac | ctg | gag | 297 |
| Asp | Leu | Glu | |

<210> SEQ ID NO 11
<211> LENGTH: 99
<212> TYPE: PRT
<213> ORGANISM: Homo sapiens

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys Gln Tyr Thr Ser Ile His His Gly Val
    50                  55                  60

Val Glu Val Asp Ala Ala Val Thr Pro Glu Glu Arg His Leu Ser Lys
65                  70                  75                  80

Met Gln Gln Asn Gly Tyr Glu Asn Pro Thr Tyr Lys Phe Phe Glu Gln
                85                  90                  95

Met Gln Asn

<210> SEQ ID NO 12
<211> LENGTH: 297
<212> TYPE: DNA
<213> ORGANISM: Homo sapiens
<220> FEATURE:
<221> NAME/KEY: CDS
<222> LOCATION: (1)..(297)

<400> SEQUENCE: 12

| | | | | | | | | | | | | | | | | |
|---|---|---|---|---|---|---|---|---|---|---|---|---|---|---|---|---|
| gat | gca | gaa | ttc | cga | cat | gac | tca | gga | tat | gaa | gtt | cat | cat | caa | aaa | 48 |
| Asp | Ala | Glu | Phe | Arg | His | Asp | Ser | Gly | Tyr | Glu | Val | His | His | Gln | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | gtg | ttc | ttt | gca | gaa | gat | gtg | ggt | tca | aac | aaa | ggt | gca | atc | att | 96 |
| Leu | Val | Phe | Phe | Ala | Glu | Asp | Val | Gly | Ser | Asn | Lys | Gly | Ala | Ile | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| gga | ctc | atg | gtg | ggc | ggt | gtt | gtc | ata | gcg | aca | gtg | atc | gtc | atc | acc | 144 |
| Gly | Leu | Met | Val | Gly | Gly | Val | Val | Ile | Ala | Thr | Val | Ile | Val | Ile | Thr | |
| | | 35 | | | | | 40 | | | | | 45 | | | | |

```
ttg gtg atg ctg aag aag aaa cag tac aca tcc att cat cat ggt gtg      192
Leu Val Met Leu Lys Lys Lys Gln Tyr Thr Ser Ile His His Gly Val
 50                  55                  60 gtg gag gtt gac gcc gct gtc acc cca gag gag cgc cac ctg tcc aag      240
Val Glu Val Asp Ala Ala Val Thr Pro Glu Glu Arg His Leu Ser Lys
 65                  70                  75                  80 atg cag cag aac ggc tac gaa aat cca acc tac aag ttc ttt gag cag      288
Met Gln Gln Asn Gly Tyr Glu Asn Pro Thr Tyr Lys Phe Phe Glu Gln
                 85                  90                  95 atg cag aac                                                          297
Met Gln Asn <210> SEQ ID NO 13
<211> LENGTH: 351
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(348)

<400> SEQUENCE: 13 atg gtg aag agt gag ccg gtg gag cct ccg ctg ccc tcg cag ctg cac       48
Met Val Lys Ser Glu Pro Val Glu Pro Pro Leu Pro Ser Gln Leu His
  1               5                  10                  15 ctc gtg tac gtg gca gcg gcc gcc ttc gtg ctc ctg ttc ttt gtg ggc       96
Leu Val Tyr Val Ala Ala Ala Ala Phe Val Leu Leu Phe Phe Val Gly
             20                  25                  30 tgt ggg gtg ctg ctg tcc cgc aag cgc cgg cgg cag cat ggc cag ctc      144
Cys Gly Val Leu Leu Ser Arg Lys Arg Arg Arg Gln His Gly Gln Leu
         35                  40                  45 tgg ttc cct gag ggt ttc aaa gtg tca gag gcc agc aag aag aag cgg      192
Trp Phe Pro Glu Gly Phe Lys Val Ser Glu Ala Ser Lys Lys Lys Arg
 50                  55                  60 aga gag ccc ctc ggc gag gac tca gtc ggc ctc aag ccc ctg aag aat      240
Arg Glu Pro Leu Gly Glu Asp Ser Val Gly Leu Lys Pro Leu Lys Asn
 65                  70                  75                  80 gcc tca gat ggt gct ctg atg gac gac aat cag aac gag tgg gga gac      288
Ala Ser Asp Gly Ala Leu Met Asp Asp Asn Gln Asn Glu Trp Gly Asp
                 85                  90                  95 gaa gac ctg gag gac tac aag gac gat gac gat aag gga tcc cat cac      336
Glu Asp Leu Glu Asp Tyr Lys Asp Asp Asp Asp Lys Gly Ser His His
                100                 105                 110 cat cac cat cac tag                                                  351
His His His His
        115

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 14

Met Val Lys Ser Glu Pro Val Glu Pro Pro Leu Pro Ser Gln Leu His
  1               5                  10                  15

Leu Val Tyr Val Ala Ala Ala Ala Phe Val Leu Leu Phe Phe Val Gly
             20                  25                  30

Cys Gly Val Leu Leu Ser Arg Lys Arg Arg Arg Gln His Gly Gln Leu
```

```
                    35                  40                  45
Trp Phe Pro Glu Gly Phe Lys Val Ser Glu Ala Ser Lys Lys Arg
 50                  55                  60

Arg Glu Pro Leu Gly Glu Asp Ser Val Gly Leu Lys Pro Leu Lys Asn
 65                  70                  75                  80

Ala Ser Asp Gly Ala Leu Met Asp Asp Asn Gln Asn Glu Trp Gly Asp
                 85                  90                  95

Glu Asp Leu Glu Asp Tyr Lys Asp Asp Lys Gly Ser His His
            100                 105                 110

His His His His
        115

<210> SEQ ID NO 15
<211> LENGTH: 100
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 15

Met Val Lys Ser Glu Pro Val Glu Pro Pro Leu Pro Ser Gln Leu His
 1               5                  10                  15

Leu Val Tyr Val Ala Ala Ala Ala Phe Val Leu Leu Phe Phe Val Gly
                20                  25                  30

Cys Gly Val Leu Leu Ser Arg Lys Arg Arg Arg Gln His Gly Gln Leu
                35                  40                  45

Trp Phe Pro Glu Gly Phe Lys Val Ser Glu Ala Ser Lys Lys Lys Arg
 50                  55                  60

Arg Glu Pro Leu Gly Glu Asp Ser Val Gly Leu Lys Pro Leu Lys Asn
 65                  70                  75                  80

Ala Ser Asp Gly Ala Leu Met Asp Asp Asn Gln Asn Glu Trp Gly Asp
                 85                  90                  95

Glu Asp Leu Glu
            100

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 16

Asp Tyr Lys Asp Asp Asp Lys Gly Ser His His His His His His
 1               5                  10                  15

<210> SEQ ID NO 17
<211> LENGTH: 2531
<212> TYPE: PRT
<213> ORGANISM: Mus musculus

<400> SEQUENCE: 17

Met Pro Arg Leu Leu Thr Pro Leu Leu Cys Leu Thr Leu Leu Pro Ala
 1               5                  10                  15

Arg Ala Ala Arg Gly Leu Arg Cys Ser Gln Pro Ser Gly Thr Cys Leu
                20                  25                  30

Asn Gly Gly Arg Cys Glu Val Ala Ser Gly Thr Glu Ala Cys Val Ala
                35                  40                  45
```

```
Ser Gly Ser Phe Val Gly Gln Arg Cys Gln Asp Pro Asn Pro Cys Leu
 50                  55                  60
Ser Thr Arg Cys Lys Asn Ala Gly Thr Cys Tyr Val Val Asp His Gly
 65                  70                  75                  80
Gly Ile Val Asp Tyr Ala Cys Ser Cys Pro Leu Gly Phe Ser Gly Pro
                 85                  90                  95
Leu Cys Leu Thr Pro Leu Asp Lys Pro Cys Leu Ala Asn Pro Cys Arg
            100                 105                 110
Asn Gly Gly Thr Cys Asp Leu Leu Thr Leu Thr Glu Tyr Lys Cys Arg
            115                 120                 125
Cys Ser Pro Gly Trp Ser Gly Lys Ser Cys Gln Gln Ala Asp Pro Cys
130                 135                 140
Ala Ser Asn Pro Cys Ala Asn Gly Gly Gln Cys Leu Pro Phe Glu Ser
145                 150                 155                 160
Ser Tyr Ile Cys Arg Cys Pro Pro Gly Phe His Gly Pro Thr Cys Arg
                165                 170                 175
Gln Asp Val Asn Glu Cys Ser Gln Asn Pro Gly Leu Cys Arg His Gly
            180                 185                 190
Gly His Cys His Asn Glu Ile Gly Ser Tyr Arg Cys Ala Cys Cys Ala
            195                 200                 205
Thr His Thr Gly Pro His Cys Glu Leu Pro Tyr Val Pro Cys Ser Pro
210                 215                 220
Ser Pro Cys Gln Asn Gly Ala Thr Cys Arg Pro Thr Gly Asp Thr Thr
225                 230                 235                 240
His Glu Cys Ala Cys Leu Pro Gly Phe Ala Gly Gln Asn Cys Glu Glu
                245                 250                 255
Asn Val Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Val Thr
            275                 280                 285
Gly Gln Tyr Cys Thr Glu Asp Val Asp Glu Cys Gln Leu Met Pro Asn
            290                 295                 300
Ala Cys Gln Asn Ala Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe Gln Gly Ala Thr Cys His Asp
            340                 345                 350
Arg Val Ala Ser Phe Tyr Cys Glu Cys Pro His Gly Arg Thr Gly Leu
            355                 360                 365
Leu Cys His Leu Lys His Ala Cys Ile Ser Asn Pro Cys Asn Glu Gly
            370                 375                 380
Ser Asn Cys Asp Thr Asn Pro Val Asn Gly Lys Arg Ile Cys Thr Cys
385                 390                 395                 400
Pro Ser Gly Tyr Thr Gly Pro Ala Cys Ser Gln Asp Val Asp Glu Cys
                405                 410                 415
Asp Leu Gly Ala Asn Arg Cys Glu His Ala Gly Lys Cys Leu Asn Thr
            420                 425                 430
Leu Gly Ser Phe Glu Cys Gln Cys Leu Gln Gly Tyr Thr Gly Pro Gly
            435                 440                 445
Cys Glu Ile Asp Val Asn Glu Cys Ile Ser Asn Pro Cys Gln Asn Asp
450                 455                 460
Ala Thr Cys Leu Asp Gln Ile Gly Glu Phe Gln Cys Ile Cys Met Pro
465                 470                 475                 480
```

```
Gly Tyr Glu Gly Val Tyr Cys Glu Ile Asn Thr Asp Glu Cys Ala Ser
                485                 490                 495
Ser Pro Cys Leu His Asn Gly His Cys Met Asp Lys Ile His Glu Phe
            500                 505                 510
Gln Cys Gln Cys Pro Lys Gly Phe Asn Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
            565                 570                 575
Tyr Gly Ser Cys Lys Asp Gly Val Ala Thr Phe Thr Cys Leu Cys Gln
        580                 585                 590
Pro Gly Tyr Thr Gly His His Cys Glu Thr Asn Ile Asn Glu Cys His
    595                 600                 605
Ser Gln Pro Cys Arg His Gly Gly Thr Cys Gln Asp Arg Asp Asn Ser
610                 615                 620
Tyr Leu Cys Leu Cys Leu Lys Gly Thr Thr Gly Pro Asn Cys Glu Ile
625                 630                 635                 640
Asn Leu Asp Asp Cys Ala Ser Asn Pro Cys Asp Ser Gly Thr Cys Leu
            645                 650                 655
Asp Lys Ile Asp Gly Tyr Glu Cys Ala Cys Glu Pro Gly Tyr Thr Gly
        660                 665                 670
Ser Met Cys Asn Val Asn Ile Asp Glu Cys Ala Gly Ser Pro Cys His
    675                 680                 685
Asn Gly Gly Thr Cys Glu Asp Gly Ile Ala Gly Phe Thr Cys Arg Cys
    690                 695                 700
Pro Glu Gly Tyr His Asp Pro Thr Cys Leu Ser Glu Val Asn Glu Cys
705                 710                 715                 720
Asn Ser Asn Pro Cys Ile His Gly Ala Cys Arg Asp Gly Leu Asn Gly
            725                 730                 735
Tyr Lys Cys Asp Cys Ala Pro Gly Trp Ser Gly Thr Asn Cys Asp Ile
        740                 745                 750
Asn Asn Asn Glu Cys Glu Ser Asn Pro Cys Val Asn Gly Gly Thr Cys
    755                 760                 765
Lys Asp Met Thr Ser Gly Tyr Val Cys Thr Cys Arg Glu Gly Phe Ser
770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
            805                 810                 815
Cys Pro Leu Pro Tyr Thr Gly Ala Thr Cys Glu Val Val Leu Ala Pro
        820                 825                 830
Cys Ala Thr Ser Pro Cys Lys Asn Ser Gly Val Cys Lys Glu Ser Glu
    835                 840                 845
Asp Tyr Glu Ser Phe Ser Cys Val Cys Pro Thr Gly Trp Gln Gly Gln
    850                 855                 860
Thr Cys Glu Val Asp Ile Asn Glu Cys Val Lys Ser Pro Cys Arg His
865                 870                 875                 880
Gly Ala Ser Cys Gln Asn Thr Asn Gly Ser Tyr Arg Cys Leu Cys Gln
            885                 890                 895
Ala Gly Tyr Thr Gly Arg Asn Cys Glu Ser Asp Ile Asp Asp Cys Arg
```

```
                900             905             910
Pro Asn Pro Cys His Asn Gly Gly Ser Cys Thr Asp Gly Ile Asn Thr
            915             920             925
Ala Phe Cys Asp Cys Leu Pro Gly Phe Gln Gly Ala Phe Cys Glu Glu
            930             935             940
Asp Ile Asn Glu Cys Ala Ser Asn Pro Cys Gln Asn Gly Ala Asn Cys
945             950             955             960
Thr Asp Cys Val Asp Ser Tyr Thr Cys Thr Cys Pro Val Gly Phe Asn
                965             970             975
Gly Ile His Cys Glu Asn Asn Thr Pro Asp Cys Thr Glu Ser Ser Cys
            980             985             990
Phe Asn Gly Gly Thr Cys Val Asp Gly Ile Asn Ser Phe Thr Cys Leu
            995             1000            1005
Cys Pro Pro Gly Phe Thr Gly Ser Tyr Cys Gln Tyr Asp Val Asn
        1010            1015            1020
Glu Cys Asp Ser Arg Pro Cys Leu His Gly Gly Thr Cys Gln Asp
        1025            1030            1035
Ser Tyr Gly Thr Tyr Lys Cys Thr Cys Pro Gln Gly Tyr Thr Gly
        1040            1045            1050
Leu Asn Cys Gln Asn Leu Val Arg Trp Cys Asp Ser Ala Pro Cys
        1055            1060            1065
Lys Asn Gly Gly Arg Cys Trp Gln Thr Asn Thr Gln Tyr His Cys
        1070            1075            1080
Glu Cys Arg Ser Gly Trp Thr Gly Val Asn Cys Asp Val Leu Ser
        1085            1090            1095
Val Ser Cys Glu Val Ala Ala Gln Lys Arg Gly Ile Asp Val Thr
        1100            1105            1110
Leu Leu Cys Gln His Gly Gly Leu Cys Val Asp Glu Gly Asp Lys
        1115            1120            1125
His Tyr Cys His Cys Gln Ala Gly Tyr Thr Gly Ser Tyr Cys Glu
        1130            1135            1140
Asp Glu Val Asp Glu Cys Ser Pro Asn Pro Cys Gln Asn Gly Ala
        1145            1150            1155
Thr Cys Thr Asp Tyr Leu Gly Gly Phe Ser Cys Lys Cys Val Ala
        1160            1165            1170
Gly Tyr His Gly Ser Asn Cys Ser Glu Glu Ile Asn Glu Cys Leu
        1175            1180            1185
Ser Gln Pro Cys Gln Asn Gly Gly Thr Cys Ile Asp Leu Thr Asn
        1190            1195            1200
Ser Tyr Lys Cys Ser Cys Pro Arg Gly Thr Gln Gly Val His Cys
        1205            1210            1215
Glu Ile Asn Val Asp Asp Cys His Pro Pro Leu Asp Pro Ala Ser
        1220            1225            1230
Arg Ser Pro Lys Cys Phe Asn Asn Gly Thr Cys Val Asp Gln Val
        1235            1240            1245
Gly Gly Tyr Thr Cys Thr Cys Pro Pro Gly Phe Val Gly Glu Arg
        1250            1255            1260
Cys Glu Gly Asp Val Asn Glu Cys Leu Ser Asn Pro Cys Asp Pro
        1265            1270            1275
Arg Gly Thr Gln Asn Cys Val Gln Arg Val Asn Asp Phe His Cys
        1280            1285            1290
Glu Cys Arg Ala Gly His Thr Gly Arg Arg Cys Glu Ser Val Ile
        1295            1300            1305
```

-continued

Asn Gly Cys Arg Gly Lys Pro Cys Lys Asn Gly Gly Val Cys Ala
1310              1315                1320

Val Ala Ser Asn Thr Ala Arg Gly Phe Ile Cys Arg Cys Pro Ala
1325              1330                1335

Gly Phe Glu Gly Ala Thr Cys Glu Asn Asp Ala Arg Thr Cys Gly
1340              1345                1350

Ser Leu Arg Cys Leu Asn Gly Gly Thr Cys Ile Ser Gly Pro Arg
1355              1360                1365

Ser Pro Thr Cys Leu Cys Leu Gly Ser Phe Thr Gly Pro Glu Cys
1370              1375                1380

Gln Phe Pro Ala Ser Ser Pro Cys Val Gly Ser Asn Pro Cys Tyr
1385              1390                1395

Asn Gln Gly Thr Cys Glu Pro Thr Ser Glu Asn Pro Phe Tyr Arg
1400              1405                1410

Cys Leu Cys Pro Ala Lys Phe Asn Gly Leu Leu Cys His Ile Leu
1415              1420                1425

Asp Tyr Ser Phe Thr Gly Gly Ala Gly Pro Asp Ile Pro Pro Pro
1430              1435                1440

Gln Ile Glu Glu Ala Cys Glu Leu Pro Glu Cys Gln Val Asp Ala
1445              1450                1455

Gly Asn Lys Val Cys Asn Leu Gln Cys Asn Asn His Ala Cys Gly
1460              1465                1470

Trp Asp Gly Gly Asp Cys Ser Leu Asn Phe Asn Asp Pro Trp Lys
1475              1480                1485

Asn Cys Thr Gln Ser Leu Gln Cys Trp Lys Tyr Phe Ser Asp Gly
1490              1495                1500

His Cys Asp Ser Gln Cys Asn Ser Ala Gly Cys Leu Phe Asp Gly
1505              1510                1515

Phe Asp Cys Gln Leu Thr Glu Gly Gln Cys Asn Pro Leu Tyr Asp
1520              1525                1530

Gln Tyr Cys Lys Asp His Phe Ser Asp Gly His Cys Asp Gln Gly
1535              1540                1545

Cys Asn Ser Ala Glu Cys Glu Trp Asp Gly Leu Asp Cys Ala Glu
1550              1555                1560

His Val Pro Glu Arg Leu Ala Ala Gly Thr Leu Val Leu Val Val
1565              1570                1575

Leu Leu Pro Pro Asp Gln Leu Arg Asn Asn Ser Phe His Phe Leu
1580              1585                1590

Arg Glu Leu Ser His Val Leu His Thr Asn Val Val Phe Lys Arg
1595              1600                1605

Asp Ala Gln Gly Gln Gln Met Ile Phe Pro Tyr Tyr Gly His Glu
1610              1615                1620

Glu Glu Leu Arg Lys His Pro Ile Lys Arg Ser Thr Val Gly Trp
1625              1630                1635

Ala Thr Ser Ser Leu Leu Pro Gly Thr Ser Gly Gly Arg Gln Arg
1640              1645                1650

Arg Glu Leu Asp Pro Met Asp Ile Arg Gly Ser Ile Val Tyr Leu
1655              1660                1665

Glu Ile Asp Asn Arg Gln Cys Val Gln Ser Ser Gln Cys Phe
1670              1675                1680

Gln Ser Ala Thr Asp Val Ala Ala Phe Leu Gly Ala Leu Ala Ser
1685              1690                1695

Leu Gly Ser Leu Asn Ile Pro Tyr Lys Ile Glu Ala Val Lys Ser
1700              1705                1710

-continued

```
Glu Pro Val Glu Pro Pro Leu Pro Ser Gln Leu His Leu Met Tyr
    1715                1720                1725

Val Ala Ala Ala Ala Phe Val Leu Leu Phe Val Gly Cys Gly
    1730                1735                1740

Val Leu Leu Ser Arg Lys Arg Arg Arg Gln His Gly Gln Leu Trp
    1745                1750                1755

Phe Pro Glu Gly Phe Lys Val Ser Glu Ala Ser Lys Lys Lys Arg
    1760                1765                1770

Arg Glu Pro Leu Gly Glu Asp Ser Val Gly Leu Lys Pro Leu Lys
    1775                1780                1785

Asn Ala Ser Asp Gly Ala Leu Met Asp Asp Asn Gln Asn Glu Trp
    1790                1795                1800

Gly Asp Glu Asp Leu Glu Thr Lys Lys Phe Arg Phe Glu Glu Pro
    1805                1810                1815

Val Val Leu Pro Asp Leu Ser Asp Gln Thr Asp His Arg Gln Trp
    1820                1825                1830

Thr Gln Gln His Leu Asp Ala Ala Asp Leu Arg Met Ser Ala Met
    1835                1840                1845

Ala Pro Thr Pro Pro Gln Gly Glu Val Asp Ala Asp Cys Met Asp
    1850                1855                1860

Val Asn Val Arg Gly Pro Asp Gly Phe Thr Pro Leu Met Ile Ala
    1865                1870                1875

Ser Cys Ser Gly Gly Gly Leu Glu Thr Gly Asn Ser Glu Glu Glu
    1880                1885                1890

Glu Asp Ala Pro Ala Val Ile Ser Asp Phe Ile Tyr Gln Gly Ala
    1895                1900                1905

Ser Leu His Asn Gln Thr Asp Arg Thr Gly Glu Thr Ala Leu His
    1910                1915                1920

Leu Ala Ala Arg Tyr Ser Arg Ser Asp Arg Arg Lys Arg Leu Glu
    1925                1930                1935

Ala Ser Ala Asp Ala Asn Ile Gln Asp Asn Met Gly Arg Thr Pro
    1940                1945                1950

Leu His Ala Ala Val Ser Ala Asp Ala Gln Gly Val Phe Gln Ile
    1955                1960                1965

Leu Leu Arg Asn Arg Ala Thr Asp Leu Asp Ala Arg Met His Asp
    1970                1975                1980

Gly Thr Thr Pro Leu Ile Leu Ala Ala Arg Leu Ala Val Glu Gly
    1985                1990                1995

Met Leu Glu Asp Leu Ile Asn Ser His Ala Asp Val Asn Ala Val
    2000                2005                2010

Asp Asp Leu Gly Lys Ser Ala Leu His Trp Ala Ala Ala Val Asn
    2015                2020                2025

Asn Val Asp Ala Ala Val Val Leu Leu Lys Asn Gly Ala Asn Lys
    2030                2035                2040

Asp Ile Glu Asn Asn Lys Glu Glu Thr Ser Leu Phe Leu Ser Ile
    2045                2050                2055

Arg Arg Glu Ser Tyr Glu Thr Ala Lys Val Leu Leu Asp His Phe
    2060                2065                2070

Ala Asn Arg Asp Ile Thr Asp His Met Asp Arg Leu Pro Arg Asp
    2075                2080                2085

Ile Ala Gln Glu Arg Met His His Asp Ile Val Arg Leu Leu Asp
    2090                2095                2100

Glu Tyr Asn Leu Val Arg Ser Pro Gln Leu His Gly Thr Ala Leu
```

-continued

```
            2105                2110                2115

Gly Gly Thr Pro Thr Leu Ser Pro Thr Leu Cys Ser Pro Asn Gly
    2120                2125                2130

Tyr Pro Gly Asn Leu Lys Ser Ala Thr Gln Gly Lys Lys Ala Arg
    2135                2140                2145

Lys Pro Ser Thr Lys Gly Leu Ala Cys Gly Ser Lys Glu Ala Lys
    2150                2155                2160

Asp Leu Lys Ala Arg Arg Lys Ser Ser Gln Asp Gly Lys Gly Trp
    2165                2170                2175

Leu Leu Asp Ser Ser Ser Ser Met Leu Ser Pro Val Asp Ser Leu
    2180                2185                2190

Glu Ser Pro His Gly Tyr Leu Ser Asp Val Ala Ser His Pro Leu
    2195                2200                2205

Leu Pro Ser Pro Phe Gln Gln Ser Pro Ser Met Pro Leu Ser His
    2210                2215                2220

Leu Pro Gly Met Pro Asp Thr His Leu Gly Ile Ser His Leu Asn
    2225                2230                2235

Val Ala Ala Lys Pro Glu Met Ala Ala Leu Ala Gly Gly Ser Arg
    2240                2245                2250

Leu Ala Phe Glu His Pro Pro Arg Leu Ser His Leu Pro Val
    2255                2260                2265

Ala Ser Ser Ala Cys Thr Val Leu Ser Thr Asn Gly Thr Gly Ala
    2270                2275                2280

Met Asn Phe Thr Val Gly Ala Pro Ala Ser Leu Asn Gly Gln Cys
    2285                2290                2295

Glu Trp Leu Pro Arg Leu Gln Asn Gly Met Val Pro Ser Gln Tyr
    2300                2305                2310

Asn Pro Leu Arg Pro Gly Val Thr Pro Gly Thr Leu Ser Thr Gln
    2315                2320                2325

Ala Ala Gly Leu Gln His Ser Met Met Gly Pro Leu His Ser Ser
    2330                2335                2340

Leu Ser Thr Asn Thr Leu Ser Pro Ile Ile Tyr Gln Gly Leu Pro
    2345                2350                2355

Asn Thr Arg Leu Ala Thr Gln Pro His Leu Val Gln Thr Gln Gln
    2360                2365                2370

Val Gln Pro Gln Asn Leu Pro Leu Gln Pro Gln Asn Leu Gln Pro
    2375                2380                2385

Pro Ser Gln Pro His Leu Ser Val Ser Ser Ala Ala Asn Gly His
    2390                2395                2400

Leu Gly Arg Ser Phe Leu Ser Gly Glu Pro Ser Gln Ala Asp Val
    2405                2410                2415

Gln Pro Leu Gly Pro Ser Ser Leu Pro Val His Thr Ile Leu Pro
    2420                2425                2430

Gln Glu Ser Gln Ala Leu Pro Thr Ser Leu Pro Ser Ser Met Val
    2435                2440                2445

Pro Pro Met Thr Thr Thr Gln Phe Leu Thr Pro Ser Gln His
    2450                2455                2460

Ser Tyr Ser Ser Ser Pro Val Asp Asn Thr Pro Ser His Gln Leu
    2465                2470                2475

Gln Val Pro Glu Pro Thr Phe Leu Thr Pro Ser Pro Glu Ser Pro
    2480                2485                2490

Asp Gln Trp Ser Ser Ser Ser Pro His Ser Asn Ile Ser Asp Trp
    2495                2500                2505
```

```
Ser Glu Gly Ile Ser Ser Pro Pro Thr Thr Met Pro Ser Gln Ile
    2510            2515                2520

Thr His Ile Pro Glu Ala Phe Lys
    2525            2530

<210> SEQ ID NO 18
<211> LENGTH: 770
<212> TYPE: PRT
<213> ORGANISM: Homo sapiens

<400> SEQUENCE: 18

Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
             35                  40                  45

Asn Gly Lys Trp Asp Ser Asp Pro Ser Gly Thr Lys Thr Cys Ile Asp
         50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350
```

```
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Gln Glu Ala Ala Asn
        435                 440                 445
Glu Arg Gln Gln Leu Val Glu Thr His Met Ala Arg Val Glu Ala Met
    450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
    610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
            660                 665                 670
Ala Glu Phe Arg His Asp Ser Gly Tyr Glu Val His His Gln Lys Leu
        675                 680                 685
Val Phe Phe Ala Glu Asp Val Gly Ser Asn Lys Gly Ala Ile Ile Gly
    690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
            740                 745                 750
Gln Gln Asn Gly Tyr Glu Asn Pro Thr Tyr Lys Phe Phe Glu Gln Met
        755                 760                 765
Gln Asn
    770
```

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Tyr Ile Gly Ser
1               5
```